United States Patent
Ashwell et al.

(10) Patent No.: US 11,013,733 B2
(45) Date of Patent: *May 25, 2021

(54) INHIBITING MUTANT ISOCITRATE DEHYDROGENASE 1 (MLDH-1)

(71) Applicant: FORMA Therapeutics, Inc., Watertown, MA (US)

(72) Inventors: Susan Ashwell, Carlisle, MA (US); Blythe Thomson, Cincinnati, OH (US); Patrick F. Kelly, Concord, MA (US); Alan Collis, Lexington, MA (US); Jeff Davis, Hingham, MA (US); Duncan Walker, Boulder, CO (US); Wei Lu, Newton, MA (US)

(73) Assignee: FORMA Therapeutics, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/431,588

(22) Filed: Jun. 4, 2019

(65) Prior Publication Data
US 2019/0350921 A1    Nov. 21, 2019

Related U.S. Application Data

(63) Continuation-in-part of application No. PCT/US2019/032742, filed on May 16, 2019, and a continuation-in-part of application No. PCT/US2019/032747, filed on May 16, 2019, application No. 16/431,588, which is a continuation-in-part of application No. 16/414,505, filed on May 16, 2019, and a continuation-in-part of application No. 16/414,716, filed on May 16, 2019, now Pat. No. 10,532,047.

(60) Provisional application No. 62/692,591, filed on Jun. 29, 2018, provisional application No. 62/672,462, filed on May 16, 2018, provisional application No. 62/672,461, filed on May 16, 2018, provisional application No. 62/812,367, filed on Mar. 1, 2019, provisional application No. 62/798,677, filed on Jan. 30, 2019, provisional application No. 62/798,681, filed on Jan. 30, 2019, provisional application No. 62/798,684, filed on Jan. 30, 2019, provisional application No. 62/798,687, filed on Jan. 30, 2019, provisional application No. 62/798,690, filed on Jan. 30, 2019, provisional application No. 62/773,562, filed on Nov. 30, 2018, provisional application No. 62/692,598, filed on Jun. 29, 2018, provisional application No. 62/692,601, filed on Jun. 29, 2018, provisional application No. 62/692,604, filed on Jun. 29, 2018, provisional application No. 62/692,605, filed on Jun. 29, 2018, provisional application No. 62/680,566, filed on Jun. 4, 2018, provisional application No. 62/680,571, filed on Jun. 4, 2018, provisional application No. 62/680,560, filed on Jun. 4, 2018, provisional application No. 62/680,562, filed on Jun. 4, 2018, provisional application No. 62/692,591, filed on Jun. 29, 2018, provisional application No. 62/712,160, filed on Jul. 30, 2018, provisional application No. 62/701,487, filed on Jul. 20, 2018.

(51) Int. Cl.
A61K 31/4709 (2006.01)
A61K 31/706 (2006.01)
A61P 35/02 (2006.01)
A61P 35/00 (2006.01)

(52) U.S. Cl.
CPC ........ *A61K 31/4709* (2013.01); *A61K 31/706* (2013.01); *A61P 35/00* (2018.01); *A61P 35/02* (2018.01)

(58) Field of Classification Search
CPC ... A61K 31/4709; A61K 31/706; A61P 35/02; A61P 35/00
USPC .......................................................... 514/43
See application file for complete search history.

(56) References Cited

U.S. PATENT DOCUMENTS

| | | |
|---|---|---|
| 5,262,564 A | 11/1993 | Kun et al. |
| 5,984,882 A | 11/1999 | Rosenschein et al. |
| 6,410,516 B1 | 6/2002 | Baltimore et al. |
| 6,914,128 B1 | 7/2005 | Salfeld et al. |
| 6,979,675 B2 | 12/2005 | Tidmarsh |
| 7,217,286 B2 | 5/2007 | Falotico et al. |
| 8,367,347 B2 | 2/2013 | Hartmann et al. |
| 8,469,749 B2 | 6/2013 | Ladouceur et al. |
| 8,685,660 B2 | 4/2014 | Vogelstein et al. |
| 8,876,991 B2 | 11/2014 | Luebke |

(Continued)

FOREIGN PATENT DOCUMENTS

| | | |
|---|---|---|
| CN | 102558049 A | 7/2012 |
| CN | 103814020 A | 5/2014 |

(Continued)

OTHER PUBLICATIONS

Wang et al. (Hindawi Publishing Corporation Stem Cells International vol. 2017, Article ID 6962379, 11 pages).*

(Continued)

*Primary Examiner* — Shaojia A Jiang
*Assistant Examiner* — Michael C Henry
(74) *Attorney, Agent, or Firm* — Barnes & Thornburg LLP

(57) ABSTRACT

Patients diagnosed with a cancer harboring an IDH-1 mutation can be treated by the administration of a therapeutically effective amount of a pharmaceutical composition comprising Compound 1, a selective inhibitor of 2-HG production from mIDH-1 enzymes including the R132 mutations R132C, R132H, R132L, R132G, and R132S.

21 Claims, 13 Drawing Sheets

(56) References Cited

U.S. PATENT DOCUMENTS

| | | |
|---|---|---|
| 8,882,892 B2 | 11/2014 | Hoversten et al. |
| 8,883,438 B2 | 11/2014 | Cantley et al. |
| 8,933,395 B2 | 1/2015 | Mueth et al. |
| 9,073,941 B2 | 7/2015 | Wong et al. |
| 9,335,332 B2 | 5/2016 | Kumaravel et al. |
| 9,353,418 B2 | 5/2016 | Vogelstein et al. |
| 9,624,175 B2 | 4/2017 | Lin et al. |
| 9,624,216 B2 | 4/2017 | Lin et al. |
| 9,771,349 B2 | 9/2017 | Lin et al. |
| 9,815,817 B2 | 11/2017 | Lin et al. |
| 9,834,539 B2 | 12/2017 | Lin et al. |
| 10,005,734 B2 | 6/2018 | Lin et al. |
| 10,253,015 B2 | 4/2019 | Lin et al. |
| 10,266,495 B2 | 4/2019 | Lin et al. |
| 10,280,150 B2 | 5/2019 | Lin et al. |
| 10,414,752 B2 | 9/2019 | Lin et al. |
| 10,532,047 B2 | 1/2020 | Luke |
| 10,550,098 B2 | 2/2020 | Lin et al. |
| 10,610,125 B2 | 4/2020 | Dang et al. |
| 10,704,108 B2 | 7/2020 | Vogelstein et al. |
| 10,837,064 B2 | 11/2020 | Vogelstein et al. |
| 2003/0105124 A1 | 6/2003 | Sobolov-Jaynes |
| 2004/0106645 A1 | 6/2004 | Blackburn et al. |
| 2006/0281122 A1 | 12/2006 | Bryant et al. |
| 2008/0300208 A1 | 12/2008 | Einat et al. |
| 2012/0184548 A1 | 7/2012 | Dominique et al. |
| 2012/0184562 A1 | 7/2012 | Luk |
| 2014/0235620 A1 | 8/2014 | Caferro et al. |
| 2016/0083349 A1 | 3/2016 | Lin et al. |
| 2016/0083365 A1 | 3/2016 | Lin et al. |
| 2016/0083366 A1 | 3/2016 | Lin et al. |
| 2016/0083367 A1 | 3/2016 | Lin et al. |
| 2016/0311774 A1 | 10/2016 | Lin et al. |
| 2016/0311818 A1 | 10/2016 | Lin et al. |
| 2017/0081730 A1 | 3/2017 | Vogelstein et al. |
| 2017/0157132 A1* | 6/2017 | Wu .................. A61P 17/00 |
| 2017/0174658 A1 | 6/2017 | Lin et al. |
| 2018/0086733 A1 | 3/2018 | Lin et al. |
| 2018/0118732 A1 | 5/2018 | Lin et al. |
| 2018/0134682 A1 | 5/2018 | Lin et al. |
| 2018/0141910 A1 | 5/2018 | Lin et al. |
| 2018/0312487 A1 | 11/2018 | Lin et al. |
| 2018/0327361 A1 | 11/2018 | Lin et al. |
| 2018/0327382 A1 | 11/2018 | Lin et al. |
| 2019/0135781 A1 | 5/2019 | Lin et al. |
| 2019/0263778 A1 | 8/2019 | Lin et al. |
| 2019/0350919 A1 | 11/2019 | Kelly et al. |
| 2019/0350920 A1 | 11/2019 | Luke et al. |
| 2019/0350922 A1 | 11/2019 | Kelly et al. |
| 2020/0085815 A1 | 3/2020 | Luke et al. |
| 2020/0108060 A1 | 4/2020 | Kelly et al. |
| 2020/0223822 A1 | 7/2020 | Lin et al. |

FOREIGN PATENT DOCUMENTS

| | | |
|---|---|---|
| EP | 0481802 A1 | 4/1992 |
| RU | 2284325 C2 | 9/2006 |
| WO | WO-00/40749 A2 | 7/2000 |
| WO | WO-2006/054912 A1 | 5/2006 |
| WO | WO-2007/117778 A2 | 10/2007 |
| WO | WO-2008/010964 A1 | 1/2008 |
| WO | WO-2008/069242 A1 | 6/2008 |
| WO | WO-2010/028099 A1 | 3/2010 |
| WO | WO-2010/105243 A1 | 9/2010 |
| WO | WO-2011/050210 A1 | 4/2011 |
| WO | WO-2011/050211 A2 | 4/2011 |
| WO | WO-2011/072174 A1 | 6/2011 |
| WO | WO-2012/040332 A2 | 3/2012 |
| WO | WO-2012/054915 A2 | 4/2012 |
| WO | WO-2012/079532 A1 | 6/2012 |
| WO | WO-2012/129562 A2 | 9/2012 |
| WO | WO-2012/171337 A1 | 12/2012 |
| WO | WO-2012/171506 A1 | 12/2012 |
| WO | WO-2012/173682 A2 | 12/2012 |
| WO | WO-2013/046136 A1 | 4/2013 |
| WO | WO-2013/096820 A1 | 6/2013 |
| WO | WO-2013/102431 A1 | 7/2013 |
| WO | WO-2013/107291 A1 | 7/2013 |
| WO | WO-2013/107405 A1 | 7/2013 |
| WO | WO-2013/127997 A1 | 9/2013 |
| WO | WO-2014/141153 A1 | 9/2014 |
| WO | WO-2014/147586 A1 | 9/2014 |
| WO | WO-2014/184272 A2 | 11/2014 |
| WO | WO-2015/003146 A1 | 1/2015 |
| WO | WO-2015/121210 A1 | 8/2015 |
| WO | WO-2016/044781 A1 | 3/2016 |
| WO | WO-2016/044782 A1 | 3/2016 |
| WO | WO-2016/044787 A1 | 3/2016 |
| WO | WO-2016/044789 A1 | 3/2016 |
| WO | WO-2016/106331 A1 | 6/2016 |
| WO | WO-2016/108045 A2 | 7/2016 |
| WO | WO-2016/171755 A1 | 10/2016 |
| WO | WO-2016/171756 A1 | 10/2016 |
| WO | WO-2017/019429 A1 | 2/2017 |
| WO | WO-2017/146795 A1 | 8/2017 |
| WO | WO-2017/213910 A1 | 12/2017 |
| WO | WO-2017/223202 A1 | 12/2017 |
| WO | WO-2018/111707 A1 | 6/2018 |
| WO | PCT/US19/32742 | 5/2019 |
| WO | PCT/US19/32747 | 5/2019 |
| WO | WO-2019/222551 A1 | 11/2019 |
| WO | WO-2019/222553 A1 | 11/2019 |
| WO | WO-2020/232381 A1 | 11/2020 |

OTHER PUBLICATIONS

Pleyer et al. (Int. J. Mol. Sci. 2017, 18, 415, 1-18).*
Pharmion Corporation et al.; Jan. 9, 2007.*
Panknin et al. (Cancer Research; Experimental and Molecular Therapeutics; Proceedings: AACR 107th Annual Meeting 2016; Apr. 16-20, 2016; New Orleans, LA; Published Jul. 2016).*
Mellai et al. (The Distribution and Significance of IDH Mutations in Gliomas, Evolution of the Molecular Biology of Brain Tumors and the Therapeutic Implications, Terry Lichtor, IntechOpen, DOI: 10.5772/52357; Submitted: May 2, 2012 Reviewed: Aug. 14, 2012 Published: Feb. 27, 2013).*
U.S. Appl. No. 16/290,240, filed Mar. 1, 2019, Lin et al.
U.S. Appl. No. 16/414,505, filed May 16, 2019, Kelly et al.
U.S. Appl. No. 16/414,716, filed May 16, 2019, Luke et al.
Abbas, S. et al., Acquired mutations in the genes encoding IDH1 and IDH2 both are recurrent aberrations in acute myeloid leukemia: prevalence and prognostic value, Blood, 116(12): 2122-2126 (2010).
Aghili, M. et al., Hydroxyglutaric aciduria and malignant brain tumor: a case report and literature review, J. Neurooncol., 91: 233-236 (2009).
Amary, M.F. et al., IDH1 and IDH2 mutations are frequent events in central chondrosarcoma and central and periosteal chondromas but not in other mesenchymal tumours, J Pathol, 224: 334-343 (2011).
Amary, M.F. et al., Ollier disease and Maffucci syndrome are caused by somatic mosaic mutations of IDH1 and IDH2, Nature Genetics, 43(12): 1262-1265 (2011).
Amidon, G.L. et al., A Theoretical Basis for a Biopharmaceutical Drug Classification: The Correlation of in Vitro Drug Product Dissolution and in Vivo Bioavailability, Pharmaceutical Research, 12(3): 413-420 (1995).
Andrones, O.C. et al., Pharmacodynamics of mutant-IDH1 inhibitors in glioma patients probed by in vivo 3D MRS imaging of 2-hydroxyglutarate, Nature Communications, 9: 1474, 9 pages (2018).
Asteian, A. et al., Design, Synthesis, and Biological Evaluation of Indole Biphenylcarboxylic Acids as PPAR? Antagonists, ACS Med. Chem. Lett., 6: 998-1003 (2015).
Badr, M.Z.A. et al., Reaction of Quinoxaline Derivatives with Nucleophilic Reagents, , Bull Chem Soc Jpn, 56(1): 326-330 (1983).
Baer, M.R. et al., A Phase 1 Dose Escalation Study of the IDH1m Inhibitor, FT-2102, in Patients with Acute Myeloid Leukemia (AML) or Myelodysplastic Syndrome (MDS), Abstract for Congress of EHA, EHA-1757:1 page (Jun. 2018).

(56) References Cited

OTHER PUBLICATIONS

Baer, M.R. et al., A Phase 1 Dose Escalation Study of the IDH1m Inhibitor, FT-2102, in Patients with Acute Myeloid Leukemia (AML) or Myelodysplastic Syndrome (MDS), Presented at the 2018 Congress of EHA, Poster PF236, Stockholm (Jun. 15, 2018).
Bai, H. et al., Integrated genomic characterization of IDH1-mutant glioma malignant progression, Nature Genetics, 48(1): 59-66 (2016).
Balss, J. et al., Analysis of the IDH1 codon 132 mutation in brain tumors, Acta Neuropathol, 116: 597-602 (2008).
Bertus, P. and Szymoniak, J., A direct synthesis of 1-aryl- and 1-alkenylcyclopropylamines from aryl and alkenyl Nitriles Journal of Organic Chemistry, 68(18): 7133-7136 (2003).
Bleeker, F.E. et al., Recent advances in the molecular understanding of glioblastoma, J. Neurooncol, 108: 11-27 (2012).
Boddu, P. and Borthakur, G., Therapeutic targeting of isocitrate dehydrogenase mutant AML, Expert Opinion on Investigational Drugs, 26(5): 525-529 (2017).
Borg, G. et al., One-pot asymmetric synthesis of tert-butanesulfinyl-protected amines from ketones by the in situ reduction of tert-butanesulfinyl ketimines, Tetrahedron Letters, 40: 6709-6712 (1999).
Borger, D.R. et al., Circulating Oncometabolite 2-Hydroxyglutarate Is a Potential Surrogate Biomarker in Patients with Isocitrate Dehydrogenase-Mutant Intrahepatic Cholangiocarcinoma, Clin Cancer Res, 20(7): 1884-1890 (2014).
Borger, D.R., et al., Frequent mutation of isocitrate dehydrogenase (IDH)1 and IDH2 in cholangiocarcinoma identified through broad-based tumor genotyping, the Oncologist 17, 72-79 (2012).
Borodovsky, A. et al., 5-azacytidine reduces methylation, promotes differentiation and induces tumor regression in a patient-derived IDH1 mutant glioma xenograft, Oncotarget, 4(10): 1737-1747 (2013).
Brooks, E. et al., Identification and Characterization of Small-Molecule Inhibitors of the R132H/R132H Mutant Isocitrate Dehydrogenase 1 Homodimer and R132H/Wild-Type Heterodimer, Journal of Biomolecular Screening, 19(8): 1193-1200 (2014).
Bunse, L. et al., Suppression of antitumor T cell immunity by the oncometabolite (R)-2-hydroxyglutarate, Nature Medicine, 25 pages (2018).
Cairns, R.A. and Mak, T.W., Oncogenic Isocitrate Dehydrogenase Mutations: Mechanisms, Models, and Clinical Opportunities, Cancer Discover, 730-741 (2013).
Chaturvedi, A. et al., Mutant IDH1 promotes leukemogenesis in vivo and can be specifically targeted in human AML, Blood, 122(16): 2877-2887 (2013).
Chaturvedi, A. et al., Pan-mutant-IDH1 inhibitor BAY1436032 is highly effective against human IDH1 mutant acute myeloid leukemia in vivo, Leukemia, 31: 2020-2028 (2017).
Chiou, W.L., and Barve, A., Linear Correlation of the Fraction of Oral Dose Absorbed of 64 Drugs Between Humans and Rats, Pharmaceutical Research, 15(11): 1792-1795 (1998).
Cho, Y.S. et al., Discovery and Evaluation of Clinical Candidate IDH305, a Brain Penetrant Mutant IDH1 Inhibitor, ACS Med Chem Lett., 8(10): 1116-1121 (2017). Supporting Information, 31 pages.
Chowdhury, R. et al., The oncometabolite 2-hydroxyglutarate inhibits histone lysine demethylases, EMBO Reports, 12(5): 463-469 (2011).
Claus, E.B. et al., Survival and low grade glioma: the emergence of genetic Information, Neurosurg Focus, 38(1): E6, 19 pages (2015).
ClinicalTrials.gov Identifier: NCT02719574, "Open-label Study of FT-2102 With or Without Azacitidine or Cytarabine in Patients With AML or MDS With an IDH1 Mutation," (v1 dated Mar. 21, 2016, published Mar. 24, 2016, and first posted Mar. 25, 2016 at https://clinicaltrials.gov/ct2/history/NCT02719574?V_1=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v10 dated Nov. 6, 2017, published Nov. 7, 2017, and update posted Nov. 8, 2017 at https://clinicaltrials.gov/ct2/history/NCT02719574?V_10=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v11 dated Dec. 6, 2017, published Dec. 7, 2017, and update posted Dec. 8, 2017 at https://clinicaltrials.gov/ct2/history/NCT02719574?V_11=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v12 dated May 17, 2018, Published May 18, 2018, and update posted May 21, 2018 at https://clinicaltrials.gov/ct2/history/NCT02719574?V_12=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v13 dated Nov. 27, 2018, published Nov. 28, 2018, and update posted Nov. 29, 2018 at https://clinicaltrials.gov/ct2/history/NCT02719574?V_13=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v2 dated Apr. 21, 2016 published Apr. 21, 2016, and update posted Apr. 22, 2016 at https://clinicaltrials.gov/ct2/history/NCT02719574?V_2=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v3 dated Jun. 8, 2016, published Jun. 8, 2016, and update posted Jun. 9, 2016 at https://clinicaltrials.gov/ct2/history/NCT02719574?V_3=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v4 dated Jul. 1, 2016, published Jul. 1, 2016, and update posted Jul. 4, 2016 at https://clinicaltrials.gov/ct2/history/NCT02719574?V_4=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v5 dated Jul. 12, 2016, published Jul. 12, 2016, and update posted Jul. 13, 2016 at https://clinicaltrials.gov/ct2/history/NCT02719574?V_5=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v6 dated Aug. 17, 2016, published Aug. 18, 2016, and update posted Aug. 19, 2016 at https://clinicaltrials.gov/ct2/history/NCT02719574?V_6=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v7 dated Dec. 8, 2016, published Dec. 8, 2016, and update posted Dec. 9, 2016 at https://clinicaltrials.gov/ct2/history/NCT02719574?V_7=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v8 dated Feb. 15, 2017, published Feb. 16, 2017, and update posted Feb. 16, 2017 at https://clinicaltrials.gov/ct2/history/NCT02719574?V_8=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v9 dated May 5, 2017, published May 5, 2017, and update posted May 8, 2017 at https://clinicaltrials.gov/ct2/history/NCT02719574?V_9=View#StudyPageTop).
ClinicalTrials.gov Identifier: NCT02719574, "Open-label Study of FT-2102 With or Without Azacitidine or Cytarabine in Patients With AML or MDS With an IDH1 Mutation," Study Details, (First Posted May 18, 2018, Last Update Posted Nov. 29, 2018).
ClinicalTrials.gov Identifier: NCT03684811, "A Study of FT-2102 in Participants with Advanced Solid Tumors and Gliomas With an IDH1 Mutation," (v1 dated Sep. 24, 2018; update published on Sep.

(56) References Cited

OTHER PUBLICATIONS 25, 2018, and posted on Sep. 26, 2018 https://clinicaltrials.gov/ct2/history/NCT03684811?V_1=View#StudyPageTop.
ClinicalTrials.gov Identifier: NCT03684811, "A Study of FT-2102 in Participants with Advanced Solid Tumors and Gliomas With an IDH1 Mutation," (v2 dated Nov. 12, 2018; update published on Nov. 13, 2018, and posted on Nov. 14, 2018 https://clinicaltrials.gov/ct2/history/NCT03684811?V_2=View#StudyPageTop.
ClinicalTrials.gov Identifier: NCT03684811, "A Study of FT-2102 in Participants with Advanced Solid Tumors and Gliomas With an IDH1 Mutation," (v3 dated Feb. 12, 2019; update published on Feb. 12, 2019 and posted on Feb. 15, 2019 https://clinicaltrials.gov/ct2/history/NCT03684811?V_3=View#StudyPageTop.
ClinicalTrials.gov Identifier: NCT03684811, "A Study of FT-2102 in Participants with Advanced Solid Tumors and Gliomas With an IDH1 Mutation," (v4 dated Feb. 15, 2019; update published on Feb. 18, 2019, and posted on Feb. 19, 2019 https://clinicaltrials.gov/ct2/history/NCT03684811?V 4=View#StudyPageTop.
ClinicalTrials.gov Identifier: NCT03684811, "A Study of FT-2102 in Participants with Advanced Solid Tumors and Gliomas With an IDH1 Mutation," (v5 dated Mar. 13, 2019; update published on Mar. 13, 2019, and posted on Mar. 14, 2019 https://clinicaltrials.gov/ct2/history/NCT03684811?V_5=View#StudyPageTop.
ClinicalTrials.gov Identifier: NCT03684811, "A Study of FT-2102 in Participants with Advanced Solid Tumors and Gliomas With an IDH1 Mutation," Study Details (First Posted Sep. 26, 2018, Last Update Posted May 1, 2019).
Cohen, A. et al., IDH1 and IDH2 Mutations in Gliomas, Curr Neurol Neurosci Rep., 13(5): 345, 13 pages (2013).
Cortes, J.E. et al., FT-2102, an IDH1m Inhibitor, Combined with Azacitidine in Patients with Acute Myeloid Leukemia (AML) or Myelodysplastic Syndrome (MDS): Results from a Phase 1 Study, Congress of EHA 2019 Abstract Submission, 4. Acute myeloid leukemia—Clinical, EHA-3328, 2 pages (submitted Mar. 1, 2019).
Cortes, J.E. et al., FT-2102, an IDH1m Inhibitor, in Combination with Azacitidine in Patients with Acute Myeloid Leukemia (AML) or Myelodysplastic Syndrome (MDS): Results from a Phase 1 Study, ASH abstract available on online meeting program, 9 pages (submitted Jul. 31, 2018, published Nov. 1, 2018).
Cortes, J.E. et al., FT-2102, an IDH1m Inhibitor, in Combination with Azacitidine in Patients with Acute Myeloid Leukemia (AML) or Myelodysplastic Syndrome (MDS): Results from a Phase 1 Study, Poster 1452, Presented at the 60th Annual Meeting of the American Society of Hematology, San Diego, CA (Dec. 1, 2018).
Cui, Z. et al., Structure and properties of N-heterocycle-containing benzotriazoles as UV absorbers, Journal of Molecular Structure, 1054: 94-99 (2013).
Cytosar-U, Sterile Cytarabine, USP; Drug Description, Pharmacia & Upjohn Company, Revised Sep. 1997, 6 pages (Approved Oct. 15, 1998).
Dai, D. et al., Clinical pharmacokinetics/pharmacodynamics (PK/PD) of ivosidenib in patients with IDH1-mutant advanced hematologic malignancies from a phase 1 study, 2018 ASCO Annual Meeting, J Clin Oncol., 36 (Abstract 2581), 1 page (Jun. 4, 2018). URL: https://meetinglibrary.asco.org/record/158639/abstract [Retrieved Jun. 7, 2018].
Damato, S. et al., IDH1 mutations are not found in cartilaginous tumours other than central and periosteal chondrosarcomas and enchondromas, Histopathology, 60: 357-376 (2011).
Dang, L. et al., Cancer-associated IDH1 mutations produce 2-hydroxyglutarate, Nature, 462: 739-744 (2009).
Dang, L. et al., IDH mutations in cancer and progress toward development of targeted therapeutics, Annals of Oncology, 27: 599-608 (2016).
Dang, L. et al., IDH mutations in glioma and acute myeloid leukemia, Trends Mol. Med., 16(9): 387-397 (2010).
Database Caplus (Online) Chemical Abstracts Service, Columbus, Ohio, US; retrieved from STN Database accession No. 1987:

407040 abstract, Prostakov, N.S. et al., Synthesis of substituted 2-pyridones and 4-aza-3-fluorenones, Khimiya Geterotsiklicheskikh Soedinenii, 7: 939-942 (1986).
Database Registry (Online) Chemical Abstracts Service, Columbus, Ohio, US; Database accession No. 1434379-53-9 (Jun. 5, 2013).
Database Registry (Online) Chemical Abstracts Service, Columbus, Ohio, US; Database accession No. 1497653-96-9 (Dec. 18, 2013).
Database Registry (Online) Chemical Abstracts Service, Columbus, Ohio, US; Database accession No. 1567357-55-4 (Mar. 12, 2014).
Database Registry (Online) Chemical Abstracts Service, Columbus, Ohio, US; Database accession No. 1567456-94-3 (Mar. 12, 2014).
De Botton, S. et al., FT-2102, an IDH1m Inhibitor, Induces Mutation Clearance in Patients With Acute Myeloid Leukemia (AML) or Myelodysplastic Syndrome (MDS) Treated in Phase 1 Dose Escalation and Expansion Study, Abstract Submission, 4. Acute myeloid leukemia Clinical, EHA-3251, 2 pages (submitted Mar. 1, 2019).
Deng, G. et al., Selective Inhibition of Mutant Isocitrate Dehydrogenase 1 (IDH1) via Disruption of a Metal Binding Network by an Allosteric Small Molecule, the Journal of Biological Chemistry, 290: 762-774 (2014).
Derissen, E.J.B. et al., ConciseDrug Review:Azacitidine and-Decitabine, the Oncologist; 18: 619-624 (2013).
Diao, L. and Meibohm, B., Pharmacometric Applications and Challenges in the Development of Therapeutic Antibodies in Immuno-Oncology, Current Pharmacology Reports, 4: 285-291 (2018).
Dohner, H., Diagnosis and management of AML in adults: 2017 ELN recommendations from an international expert panel, Blood, 129: 424-447 (2017).
Eckmann, K.R. et al., Chemotherapy Outcomes for the Treatment of Unresectable Intrahepatic and Hilar Cholangiocarcinoma: A Retrospective Analysis, Gastrointest Cancer Res 4: 155-160 (2011).
El-Khoueiry, A.B. et al., Nivolumab in patients with advanced hepatocellular carcinoma (CheckMate 040): results of phase 1/2 dose escalation and expansion, USC Norris Comprehensive Cancer Center, 36 pages (2017).
Estekizadeh, A. et al., Increased cytomegalovirus replication by 5-Azacytidine and viral-induced cytoplasmic expression of DNMT-1 in medulloblastoma and endothelial cells, International Journal of Oncology, 52: 1317-1327 (2018).
Estey E., Acute myeloid leukemia and myelodysplastic syndromes in older patients, JCO, 25: 1908-1915 (2007).
Faderl, S. et al., Clofarabine plus cytarabine compared with cytarabine alone in older patients with relapsed or refractory acute myelogenous leukemia: results from the Classic I trial, J Clin Oncol., 30: 2492-2499 (2012).
Fatima, S., Molecular docking and 3D-QSAR studies on inhibitors of DNA damage signaling enzyme human PARP-1, J Receptors and Signal Transduction, 32(4) 214-224 (2012).
Fernandez, H.F. et al., Anthracycline dose intensification in acute myeloid leukemia, NEJM, 361: 1249-1259 (2009).
Figueroa, M.E. et al., Leukemic IDH1 and IDH2 mutations result in a hypermethylation phenotype, disrupt TET2 function, and impair hematopoietic differentiation, Cancer Cell, 18:553-567 (2010).
Flavahan, W.A. et al., Insulator dysfunction and oncogene activation in IDH mutant gliomas, Nature, 1-16 (2015).
Forma Therapeutics, Best-in-Class mIDH1 Inhibitor FT-2102, Presentation, 24 slides (Jan. 8-11, 2018).
Forma Therapeutics, Discovery and Optimization of a Novel Series of Inhibitors of mt-IDH1, 7th Annual Advances in Chemical Sciences Symposium, Presentation, 21 slides (May 4, 2018).
Forma Therapeutics, Forma Therapeutics and the University of Oxford Announce Multi-Year Collaboration to Advance the Development of Deubiquitinating Enzyme (DUB) Inhibitors for the Treatment of Neurodegenerative Diseases, Press Release, 2 pages (May 9, 2018).
Forma Therapeutics, Forma Therapeutics Announces Presentation at the 2018 American Society of Clinical Oncology (ASCO) Annual Meeting, FT-2102 IDH1m Inhibitor Clinical Data Selected for Oral Presentation, Abstract 7009:1 page (May 10, 2018).
Frankel, S.R. et al., The "retinoic acid syndrome" in acute promyelocytic leukemia, Ann Intern Med., 117(4): 292-296 (1992).

(56) References Cited

OTHER PUBLICATIONS

Gaal, J. et al., Isocitrate Dehydrogenase Mutations are Rare in Pheochromocytomas and Paragangliomas, J. Clin. Endocrinol. Metab., 95(3): 1274-1278 (2010).
Ghiam, A.F. et al., IDH mutation status in prostate cancer, Oncogene, 31: 3826 (2012).
Goyal, L. et al., Prognosis and Clinicopathologic Features of Patients With Advanced Stage Isocitrate Dehydrogenase (IDH)Mutant and IDHWild-Type Intrahepatic Cholangiocarcinoma, the Oncologist, 20: 1019-1027 (2015).
Gross, S. et al., Cancer-associated metabolite 2-hydroxyglutarate accumulates in acute myelogenous leukemia with isocitrate dehydrogenase 1 and 2 mutations, J. Exp. Med., 207(2): 339-344 (2010).
Hayden, J.T. et al., Frequent IDH1 mutations in supratentorial primitive neuroectodermal tumors (sPNET) of adults but not children, Cell Cycle, 8(11): 1806-1807 (2009).
He, Y. et al., Asperspiropene A, a novel fungal metabolite as an inhibitor of cancer-associated mutant isocitrate dehydrogenase 1, Org. Chem. Front., 1-8 (2017).
Hindson, B. J. et al., High-Throughput Droplet Digital PCR System for Absolute Quantitation of DNA Copy Number, Anal. Chem., 83(22): 8604-8610 (2011).
Hondeghem, L.M. et al., Blinded Test in Isolated Female Rabbit Heart Reliably Identifies Action Potential Duration Prolongation and Proarrhythmic Drugs: Importance of Triangulation, Reverse Use Dependence, and Instability, Journal of Cardiovascular Pharmacology, 41: 14-24 (2003).
Hondeghem, L.M. et al., Instability and Triangulation of the Action Potential Predict Serious Proarrhythmia, but Action Potential Duration Prolongation is Antiarrhythmic, Circulation, 103: 2004-2013 (2001).
ICH Harmonised Tripartite Guideline, Good Manufacturing Practice Guide for Active Pharmaceutical Ingredients Q7, Current Step 4 version, 49 pages (Nov. 10, 2000).
International Search Report for PCT/US2015/051044, 4 pages (dated Nov. 23, 2015).
International Search Report for PCT/US2015/051046, 3 pages (dated Oct. 30, 2015).
International Search Report for PCT/US2015/051053, 4 pages (dated Oct. 28, 2015).
International Search Report for PCT/US2015/051055, 3 pages (dated Nov. 13, 2015).
International Search Report for PCT/US2015/051056, 4 pages (dated Nov. 20, 2015).
International Search Report for PCT/US2015/051059, 3 pages (dated Oct. 30, 2015).
Janin, M. et al., Serum 2-Hydroxyglutarate Production in IDH1- and IDH2-Mutated De Novo Acute Myeloid Leukemia: A Study by the Acute Leukemia French Association Group, Journal of Clinical Oncology, 32(4): 297-305 (2014).
Jiang, K. et al., Primary Liver Cancers, Part 2: Progression Pathways and Carcinogenesis, Cancer Control, 25(1): 1-9 (2018).
Jones, S.; et al., Discovery and Optimization of Allosteric Inhibitors of Mutant Isocitrate Dehydrogenase 1 (R132H IDH1) Displaying Activity in Human Acute Myeloid Leukemia Cells, J. Med. Chem., 59(24): 11120-11137 (2016).
Kang, M.R. et al., Mutational analysis of IDH1 codon 132 in glioblastomas and other common cancers, Int. J. Cancer, 125: 353-355 (2009).
Kats, L.M., et al., Proto-oncogenic role of mutant IDH2 in leukemia initiation and maintenance, Cell Stem Cell, 14:329-341 (2014).
Koivunen, P. et al., Transformation by the R Enantiomer of 2-Hydroxyglutarate Linked to EgIN Activation, Nature, 483(7390): 484-488 (2013).
Kombarov, R.V. et al., CA Accession No. 138:368869, abstract only of Chem of Het Compounds, 38(9): 1154-1155 (2002).
Kopinja, J. et al., A Brain Penetrant Mutant IDH1 Inhibitor Provides in Vivo Survival Benefit, Scientific Reports, 7: 13853, 14 pages (2017).
Kurz, S.C. and Wen, P.Y., Quo Vadis—Do Immunotherapies Have a Role in Glioblastoma?, Curr Treat Options Neurol, 20: 14, 1-23 (2018).
Labussiere, M. et al., IDH1 Gene Mutations: A New Paradigm in Glioma Prognosis and Therapy?, the Oncologist, 15: 196-199 (2010).
Law, J. M.; et al., Discovery of 8-Membered Ring Sulfonamides as Inhibitors of Oncogenic Mutant Isocitrate Dehydrogenase 1. ACS Medicinal Chemistry Letters, 7(10): 944-949 (2016).
Lee, J.H. et al., IDH1 R132C mutation is detected in clear cell hepatocellular carcinoma by pyrosequencing, World Journal of Surgical Oncology, 15: 82, 8 pages (2017).
Levell, J. R. et al., Optimization of 3-pyrimidin-4-yl-oxazolidin-2-ones as allosteric and mutant specific inhibitors of IDH1, ACS Med. Chem. Lett., 8: 151-156 (2017).
Liu, G. et al., Catalytic Asymmetric Synthesis of tert-Butanesulfinamide. Application to the Asymmetric Synthesis of Amines, J. Am. Chem. Soc., 119: 9913-9914 (1997).
Liu, G. et al., Synthesis of enantiomerically pure N-tert-butanesulfinyl imines (tertbutanesulfinimines) by the direct condensation of tert-butanesulfinamide with aldehydes and ketones. J. Org. Chem., 64(6): 1278-1284 (1999).
Liu, Z. et al., Inhibition of cancerassociated mutant isocitrate dehydrogenases: synthesis, structureactivity relationship, and selective antitumor activity. J. Med. Chem., 57: 8307-8318 (2014).
Lopez, G.Y. et al., IDH1 mutation identified in human melanoma, Biochem Biophys Res Commun., 398(3): 585-587 (2010).
Losman, J-A. et al., (R)-2-Hydroxyglutarate is Sufficient to Promote Leukemogenesis and its Effects are Reversible, Science, 339(6127): 9 pages (2013).
Lu, C. et al., IDH mutation impairs histone demethylation and results in a block to cell differentiation, Nature, 483(7390): 474-478 (2012).
Lu, C. et al., Induction of sarcomas by mutant IDH2, Genes & Development, 27: 1986-1998 (2013).
Mahmood, I., Prediction of Clearance, Volume of Distribution and Half-life by Allometric Scaling and by use of Plasma Concentrations Predicted from Pharmacokinetic Constants: a Comparative Study, J. Pharm. Pharmacol., 51: 905-910 (1999).
Mantica, M. et al., Retrospective study of nivolumab for patients with recurrent high grade gliomas, Journal of Neuro-Oncology, 139: 625-631 (2018).
Mardis, E.R. et al., Recurring Mutations Found by Sequencing an Acute Myeloid Leukemia Genome, N Engl J Med, 361(11): 1058-1066 (2009).
McBrayer, S.K. et al., Transaminase Inhibition by 2-Hydroxyglutarate Impairs Glutamate Biosynthesis and Redox Homeostasis in Glioma, Cell, 175: 101-116 (2018).
Medeiros, B.C. et al., Isocitrate dehydrogenase mutations in myeloid malignancies, Leukemia, 31: 272-281 (2017).
Meijer, D. et al., Genetic Characterization of Mesenchymal, Clear Cell, and Dedifferentiated Chondrosarcoma, Genes, Chromosomes & Cancer, 51:899-909 (2012).
Metallo, C.M. et al, Reductive glutamine metabolism by IDH1 mediates lipogenesis under hypoxia, Nature, 481(7381):380-384 (2011).
Meth-Cohn, O. and Stanforth, S. P. The Vilsmeier-Haack reaction (Review), Compr. Org. Synth., 2: 777-779 (1991).
Mohamed, E.A. et al., CA Accession No. 122:160601, abstract only of Indian J Chem, Sect B: Org Chem Inc Med Chem, 34B(1): 21-26 (1995).
Molenaar, R.J. et al., Wild-type and mutated IDH1/2 enzymes and therapy responses, Oncogene, 37: 1949-1960 (2018).
Morshed, M.N. et al., Computational approach to the identification of novel Aurora-A inhibitors, Bioorg & Med Chem, 19: 907-916 (2011).
National Comprehensive Cancer Network, Inc., NCCN Clinical Practice Guidelines in Oncology (NCCN Guidelines®), Acute Myeloid Leukemia, Version 2.2018 (Aug. 1, 2018).
Okoye-Okafor, U.C. et al., New IDH1 mutant inhibitors for treatment of acute myeloid leukemia, Nat. Chem. Biol., 11: 878-886 (2015).

(56) References Cited

OTHER PUBLICATIONS

Oran, B. and Weisdorf, D. Survival for older patients with acute myeloid leukemia: a population-based study, Haematologica, 97: 1916-1924 (2012).

Pansuriya, T.C. et al., Somatic mosaic IDH1 and IDH2 mutations are associated with enchondroma and spindle cell hemangioma in Ollier disease and Maffucci syndrome, Nature Genetics, 43(12): 1256-1261 (2011).

Parsons, D.W. et al., An Integrated Genomic Analysis of Human Glioblastoma Multiforme, Science, 321(5897): 1807, 15 pages (2008).

Paschka, P. et al., IDH1 and IDH2 mutations are frequent genetic alterations in acute myeloid leukemia and confer adverse prognosis in cytogenetically normal acute myeloid leukemia with NPM1 mutation without FLT3 internal tandem duplication, J Clin Oncol., 22: 3636-3643 (2010).

Pelosi, E. et al., Isocitrate dehydrogenase mutations in human cancers: physiopathologic mechanisms and therapeutic Targeting. Journal of Exploratory Research in Pharmacology, 1: 20-34 (2016).

Penard-Lacronique, V. and, Bernard, O.A., IDH1, Histone Methylation, and So Forth, Cancer Cell, 30: 192-194 (2016).

Peng, D. et al., Epigenetic silencing of Th1 type chemokines shapes tumor immunity and immunotherapy, Nature, 527(7577): 249-253 (2015).

Pollyea, D.A. et al., Ivosidenib (AG-120) in Mutant IDH1 Relapsed/Refractory Acute Myeloid Leukemia: Results of a Phase 1 Study, European Hematology Association, Abstract S1560, 2(S1): 718 (2018).

Popovici-Muller, J. et al., Discovery of the First Potent Inhibitors of Mutant IDH1 That Lower Tumor 2-HG in Vivo, ACS Med. Chem. Lett., 3(10): 850-855 (2012).

Prensner, J.R. and Chinnaiyan, A.M., Metabolism unhinged: IDH mutations in cancer, Nature Medicine, 17(3): 291-293 (2011).

Prostakov, N.S. et al., Chemistry of Heterocyclic Compounds, CHCCAL, 22(7): 685-810 (1986).

Pusch, S. et al., Pan-mutant IDH1 inhibitor BAY 1436032 for effective treatment of IDH1 mutant astrocytoma in vivo. Acta Neuropathologica, 133(4): 629-644 (2017).

Ravandi, F. et al., Vosaroxin plus cytarabine versus placebo plus cytarabine in patients with first relapsed or refractory acute myeloid leukemia (VALOR): a randomized, controlled, double-blind, multinational, phase 3 study, Lancet Oncol., 16: 1025-1036 (2015).

Roboz, G.J. et al., International randomized Phase 21 study of elacytarabine versus investigator choice in patients with relapsed/refractory acute myeloid leukemia, J Clin Oncol., 20: 1919-1926 (2014).

Rohle, D. et al., An Inhibitor of Mutant IDH1 Delays Growth and Promotes Differentiation of Glioma Cells, Science, 340(6132): 626-630 (2013). Supplementary Materials, 32 pages.

Rowe, J.M., AML in 2017: Advances in clinical practice, Best Practice & Research Clinical Haematology, 30: 283-286 (2017).

Saha, S.K. et al., IDH mutations in liver cell plasticity and biliary cancer, Cell Cycle, 13(20): 3176-3182 (2014).

Saha, S.K. et al., Mutant IDH inhibits HNF-4a to block hepatocyte differentiation and promote biliary cancer, Nature, 19 pages (2014).

Sasaki, M. et al., D-2-hydroxyglutarate produced by mutant IDH1 perturbs collagen maturation and basement membrane function, Genes & Development, 26: 2038-2049 (2012).

Sasaki, M. et al., IDH1(R132H) mutation increases murine haematopoietic progenitors and alters epigenetics, Nature, 488(7413): 656-659 (2012).

Schnittger, S. et al., IDH1 mutations are detected in 6.6% of 1414 AML patients and are associated with intermediate risk karyotype and unfavorable prognosis in adults younger than 60 years and unmutated NPM1 status, Blood, 116(25): 5486-5496 (2010).

Schrader, F.C. et al., Novel Type II Fatty Acid Biosynthesis (FAS II) Inhibitors as Multistage Antimalarial Agents, Chem Med Chem, 8: 442-461 (2013).

Segall, M., Multi-parameter Optimisation in Drug Discovery: Quickly targeting compounds with a good balance of properties, Optibrium Ltd, ELRIG Drug Discovery 2011, 32 pages (Sep. 7, 2011).

Sellner, L. et al. Increased levels of 2-hydroxyglutarate in Aml patients with IDH1-R132H and IDH2-R140Q mutations, Eur. J. Haematol., 85: 457-459 (2010).

Shibata, T. et al., Mutant IDH1 Confers an in Vivo Growth in a Melanoma Cell Line with BRAF Mutation, Am. J. Pathol., 178(3): 1395-1402 (2011).

Skrzypiec-Spring, M. et al., Isolated heart perfusion according to Langendorff—Still viable in the new millennium, Journal of Pharmacological and Toxicological Methods, 55: 113-126 (2007).

Sri Ramya, P.V. et al., Curcumin inspired 2-chloro/phenoxy quinoline analogues: Synthesis and biological evaluation as potential anticancer agents, Bioorganic & Medicinal Chemistry Letters 28: 892-898 (2018).

Stein, E.M. et al., Molecular remission and response patterns in patients with mutant-IDH2 acute myeloid leukemia treated with enasidenib, Blood, 133(7): 676-0867 (2019).

Struys, E.A. et al., Investigations by mass isotopomer analysis of the formation of D-2-hydroxyglutarate by cultures lymphoblasts from two patients with D-2-hydroxyglytaric aciduria, FEBS Letters, 557: 115-120 (2004).

Suman, P. et al., Synthesis and evaluation of functionalized aminobenzoboroxoles as potential anti-cancer agents, Journal of Organometallic Chemistry, 798(1): 125-131 (2015).

Talati, C. and Sweet, K., Recently approved therapies in acute myeloid leukemia: A complex treatment landscape, Leukemia Research, 73: 58-66 (2018).

Thomson, B. and Lipford, K., A Phase 1 b/2 Study of FT-2102 in Patients with Advanced Solid Tumors and Gliomas with an IDH1 Mutation, NCT: 03684811, 2102-ONC-102, 11 pages, Forma Therapeutics (Jan. 31, 2019).

Thomson, B. and Lipford, K., A Phase 1 b/2 Study of FT-2102 in Patients with Advanced Solid Tumors and Gliomas with an IDH1 Mutation, Poster Presented at the Cholangiocarcinoma Foundation Annual Conference, Salt Lake City, UT (Jan. 30, 2019).

Tintori, C. et al., Identification of Hck Inhibitors as Hits for the Development of Antileukemia and Anti-HIV Agents, Chem Med Chem, 8: 1353-1360 (2013).

Turcan, S. et al., Efficient induction of differentiation and growth inhibition in IDH1 mutant glioma cells by the DNMT Inhibitor Decitabine, Oncotarget, 4(10): 1729-1736 (2013).

Urban, D. J. et al., Assessing inhibitors of mutant isocitrate dehydrogenase using a suite of pre-clinical discovery assays, Scientific Reports 7(1): 12758 (2017).

Valle, J. et al., Cisplatin plus Gemcitabine versus Gemcitabine for Biliary Tract Cancer, N Engl J Med, 362: 1273-1281 (2010).

Venkanna, P. et al., 2,4,6-Trichloro-1,3,5-triazine and N,N'-dimethylformamide as an effective Vilsmeier-Haack reagent for the synthesis of 2-chloro-3-formyl quinolines from acetanilides, Tetrahedron Letters, 56(37): 5164-5167 (2015).

Vidaza, Azacitidine for injection; Drug Description, Manufactured for Pharmion Corporation, Manufactured by Ben Venue Laboratories, Inc., 19 pages (Edition Date: Jan. 9, 2007).

Vogelstein, B. and Kinzler, K.W., Digital PCR, Proc. Natl. Acad. Sci. USA, 96: 9236-9241 (1999).

Wager, T.T. et al., Defining Desirable Central Nervous System Drug Space through the Alignment of Molecular Properties, in Vitro ADME, and Safety Attributes, ACS Chem. Neurosci., 1:420-434 (2010).

Wager, T.T. et al., Moving beyond Rules: The Development of a Central Nervous System Multiparameter Optimization (CNS MPO) Approach to Enable Alignment of Druglike Properties. ACS Chem. Neurosci., 1(6): 435-449 (2010).

Wahl, D.R. et al., Glioblastoma Therapy Can be Augmented by Targeting IDH1-mediated NADPH Biosynthesis, Cancer Res, 77(4): 960-970 (2017).

Wakayama, M. and Ellman, J.A., Recycling the tert-Butanesulfinyl Group in the Synthesis of Amines Using tert-Butanesulfinamide, J. Org. Chem., 74: 2646-2650 (2009).

(56) References Cited

OTHER PUBLICATIONS

Wakimoto, H. et al., Targetable Signaling Pathway Mutations are Associated with Malignant Phenotype in IDH-Mutant Gliomas, Clin Cancer Res, 20(11): 2898-2909 (2014).
Wang, F. et al., Targeted Inhibition of Mutant IDH2 in Leukemia Cells Induces Cellular Differentiation, Science, 340: 622-626 (2013).
Wang, P. et al., Mutations in Isocitrate Dehydrogenase 1 and 2 Occur Frequently in Intrahepatic Cholangiocarcinomas and Share Hypermethylation Targets with Glioblastomas, Oncogene, 32(25): 3091-3100 (2013).
Wang, R. et al., Rapid Ti(OiPr)4 facilitated synthesis of a,a,a-trisubstituted primary amines by the addition of Grignard reagents to nitriles under microwave heating conditions. Tetrahedron Letters, 50(50): 7070-7073 (2009).
Ward, P.S. et al., The common feature of leukemia-associated IDH1 and IDH2 mutations is a neomorphic enzymatic activity that converts α-ketoglutarate to 2-hydroxyglutarate, Cancer Cell, 17(3): 225-234 (2010).
Ward, P.S. et al., The Potential for Isocitrate Dehydrogenase Mutations to Produce 2-Hydroxyglutarate Depends on Allele Specificity and Subcellular Compartmentalization, the Journal of Biological Chemistry, 288(6): 3804-3815 (2013).
Waters, N.J. et al., Validation of a rapid equilibrium dialysis approach for the measurement of plasma protein binding, J Pharm Sci., 97(10): 4586-4595 (2008).
Watts, J.M. et al., A Phase 1 Dose Escalation Study of the IDH1m Inhibitor, FT-2102, in Patients with Acute Myeloid Leukemia or Myelodysplastic Syndrome, ASCO Abstract public release May 16, 2018, Presented Jun. 4, 2018, Clin Oncol 36, 2018 (suppl; abstr 7009).
Watts, J.M. et al., A Phase 1 Dose Escalation Study of the IDH1m Inhibitor, FT-2102, in Patients with Acute Myeloid Leukemia or Myelodysplastic Syndrome, Presented at the 2018 ASCO Annual Meetings, 19 pages (Jun. 4, 2018).
Watts, J.M. et al., Phase 1 Study of the IDH1 m Inhibitor FT-2102 as a Single Agent in Patients with IDH1m Acute Myeloid Leukemia (AML) or Myelodysplastic Syndrome (MDS), ASH abstract available in online meeting program, 8 pages (submitted Jul. 31, 2018, published Nov. 1, 2018).
Watts, J.M. et al., Phase 1 Study of the IDH1m Inhibitor FT-2102 as a Single Agent in Patients with IDH1m Acute Myeloid Leukemia (AML) or Myelodysplastic Syndrome (MDS), Poster 1453, Presented at the 60th Annual Meeting of the American Society of Hematology, San Diego, CA (Dec. 1, 2018).
Wheeler, D.A. and Robers, L.R., The Cancer Genome Atlas Research Network, Comprehensive and Integrative Genomic Characterization of Hepatocellular Carcinoma, Cell, 169: 1327-1341 (2017).
Wu, F. et al., Inhibition of cancer-associated mutant isocitrate dehydrogenases by 2-thiohydantoin compounds, J. Med. Chem., 58: 6899-6908 (2015).
Xu, W. et al., Oncometabolite 2-Hydroxyglutarate is a Competitive Inhibitor of a-Ketoglutarate-Dependent Dioxygenases, Cancer Cell, 19:17-30 (2011).
Xu, X. et al., Structures of human cytosolic NADP-dependent isocitrate dehydrogenase reveal a novel self-regulatory mechanism of activity, J Biol Chem., 279(32): 33946-33957 (2004).
Yamashita, A.S. et al., Demethylation and epigenetic modification with 5-azacytidine reduces IDH1 mutant glioma growth in combination with temozolomide, Neuro-Oncology, 21(2): 189-200 (2019).
Yan, H et al., IDH1 and IDH2 Mutations in Gliomas, the New England Journal of Medicine, 360(8):765-773 (2009).
Yang, H. et al., IDH1 and IDH2 Mutations in Tumorigenesis: Mechanistic Insights and Clinical Perspectives, Clin Cancer Res, 18(20): 5562-5571 (2012).
Zhao, S. et al., Glioma-Derived Mutations in IDH1 Dominantly Inhibit IDH1 Catalytic Activity and Induce HIF-1a, Science, 324(5924): 261-265 (2009).
Zheng, B. et al., Crystallographic Investigation and Selective Inhibition of Mutant Isocitrate Dehydrogenase, ACS Medicinal Chemistry Letters, 4(6): 542-546 (2013).
Agios Pharmaceuticals, Press Release, Agios Announces Initiation of Phase 1/2 Frontline Combination Study of AG-221 or AG-120 with Vidaza® (azacitidine for injection) in Newly Diagnosed Acute Myeloid Leukemia (AML) Patients not Eligible for Intensive Chemotherapy, 4 pages (Cambridge, Mass, Mar. 30, 2016).
Agios Pharmaceuticals, Press Release, Agios Announces Phase 1 Data from Dose Expansion Cohorts of AG-120 in Patients with IDH1 Mutant Positive Glioma and Chondrosarcoma, 4 pages (Cambridge, Mass, Nov. 18, 2016).
Agios Pharmaceuticals, Press Release, Agios Pharmaceuticals to Present Clinical and Preclinical Data at the 2014 American Society of Hematology Annual Meeting, 7 pages (Cambridge, Mass., Nov. 6, 2014). URL: <http://investor.agios.com/news-releases/news-release-details/agios-pharmaceuticals-present-clinical-and-preclinical-data-2014> [Retrieved May 14, 2019].
Agios Pharmaceuticals, Press Release, Agios Presents Phase 1 Data from Dose-Escalation and Expansion Cohorts of AG-120 (Ivosidenib) in Patients with Previously Treated IDH1 Mutant Positive Cholangiocarcinoma, 4 pages (Chicago, Jun. 3, 2017).
Agios Pharmaceuticals, Press Release, Agios to Present New Data From Lead Programs at the 2015 ASH Annual Meeting, 6 pages (Cambridge, Mass., Nov. 5, 2014). URL: <http://investor.agios.com/news-releases/news-release-details/agios-present-new-data-lead-programs-2015-ash-annual-meeting> [Retrieved May 14, 2019].
Birendra, K.C. and Dinardo, C.D., Evidence for clinical differentiation and differentiation syndrome in patients with acute myeloid leukemia and IDH1 mutations treated with the targeted mutant IDH1 inhibitor, AG-120, Clin Lymphoma Myeloma Leuk , 16(8): 460-465 (2016).
Burris, H. et al., Abstract PL04-05: The first reported results of AG-120, a first-in-class, potent inhibitor of the IDH1 mutant protein, in a Phase I study of patients with advanced IDH1-mutant solid tumors, including gliomas, Mol. Cancer Ther., 14(12 Supplement 2): 5 pages (Dec. 2015).
Center for Drug Evaluation and Research, Application No. 209606Orig11000, Multi-Discipline Review, Reference ID: 4131433, 190 pages (Submission date Dec. 30, 2016).
Center for Drug Evaluation and Research, Application Number: 211192Orig1s000, Multi-Discipline Review, Reference ID: 4294809, 235 pages (Submission date Dec. 21, 2017).
De Botton, S. et al., Clinical Safety and Activity of AG-120, a First-in-Class, Potent Inhibitor of the IDH1-Mutant Protein, in a Phase 1 Study of Patients with Advanced IDH-Mutant Hematologic Malignancies. European Hematology Association Learning Center, p. 563 (2015).
Dinardo, C., Highlights in Acute Myeloid Leukemia From the 2017 American Society of Hematology Annual Meeting and Exposition, Clinical Advance in Hematology & Oncology, 16(3): Suppl 8 (Mar. 2018), a Review of Selected Presentations From the 2017 American Society of Hematology Annual Meeting and Exposition, Atlanta, Georgia, 24 pages (Mar. 8, 2018).
Dinardo, C.D. and Cortes, J.E., Mutations in AML: prognostic and therapeutic implications, Hematology, 348-355 (2016).
Dinardo, C.D. et al., Characteristics, clinical outcome, and prognostic significance of IDH mutations in AML, Am J Hematol., 90(8): 732-736 (2015).
Dinardo, C.D. et al., Durable Remissions with Ivosidenib in IDH1-Mutated Relapsed or Refractory AML, N Engl J Med, 378: 2386-2398 (2018).
Dinardo, C.D. et al., Ivosidenib (AG-120) in Mutant IDH1 AML and Advanced Hematologic Malignancies: Results of a Phase 1 Dose Escalation and Expansion Study. Presented at: ASH Annual Meeting and Exposition, Atlanta, Georgia. Abstract 725, 3 pages (Dec. 13, 2017).
Dinardo, C.D. et al., Ivosidenib (AG-120) Induced Durable Remissions and Transfusion Independence in Patients with IDH1-Mutant Relapsed or Refractory Myelodysplastic Syndrome: Results from a Phase 1 Dose Escalation and Expansion Study, 2018 ASH Annual Meeting, Blood, 132: Abstract 1812 (2018).
Dinardo, C.D. et al., Ivosidenib (AG-120) Induced Durable Remissions and Transfusion Independence in Patients with IDH1-Mutant Relapsed or Refractory Myelodysplastic Syndrome: Results from a

(56) References Cited

OTHER PUBLICATIONS

Phase 1 Dose Escalation and Expansion Study, 2018 ASH Annual Meeting, Poster, 132: Abstract 1812 (2018).
Dinardo, C.D. et al., Mutant IDH (mIDH) inhibitors, ivosidenib or enasidenib, with azacitidine (AZA) in patients with acute myeloid leukemia (AML), 2018 ASCO Annual Meeting, J Clin Oncol., 36 (Abstract 7042), 2 pages (Jun. 4, 2018). URL: https://meetinglibrary.asco.org/record/162432/abstract [Retrieved Jun. 7, 2018].
Dinardo, C.D. et al., Mutant IDH (MIDH) Inhibitors, Ivosidenib or Enasidenib, With Azacitidine (AZA) in Patients With Acute Myeloid Leukemia (AML), European Hematology Association, Abstract S1562, 2(S1): 719 (2018).
Dinardo, C.D. et al., Mutant Isocitrate Dehydrogenase (mIDH) Inhibitors, Enasidenib or Ivosidenib, in Combination with Azacitidine (AZA): Preliminary Results of a Phase 1 b/2 Study in Patients with Newly Diagnosed Acute Myeloid Leukemia (AML), ASH Annual Meeting, Blood, 130: Abstract 639 (2017).
Dinardo, C.D. et al., Mutant Isocitrate Dehydrogenase (mIDH) Inhibitors, Enasidenib or Ivosidenib, in Combination with Azacitidine (AZA): Preliminary Results of a Phase 1 b/2 Study in Patients with Newly Diagnosed Acute Myeloid Leukemia (AML), Presentation, ASH Annual Meeting, Abstract 639: 14 pages (2017).
Dinardo, C.D. et al., Serum 2-hydroxyglutarate levels predict isocitrate dehydrogenase mutations and clinical outcome in acute myeloid leukemia, Blood, 121(24): 4917-1924 (2013).
Fan, B. et al., Evaluation of the pharmacokinetic/pharmocodynamic (PK/PD) relationships of an oral, selective, first-in-class, potent IDH1 inhibitor, AG-221, from a phase 1 trial in patients with advanced IDH2 mutant positive hematologic malignancies, Blood, 124: 3737, 6 pages (2014). URL: http://www.bloodjournal.org/content/124/21/3737?sso-checked=true [Retrieved May 13, 2019].
Fan, B. et al., Evaluation of the pharmacokinetic/pharmocodynamic (PK/PD) relationships of an oral, selective, first-in-class, potent IDH1 inhibitor, AG-221, from a phase 1 trial in patients with advanced IDH2 mutant positive hematologic malignancies, Poster 3737, Presented at the 56th American Society of Hematology Annual Meeting and Exposition, San Francisco, CA, 1 page (Dec. 8, 2014).
Fan, B. et al., Longitudinal Pharmacokinetic/Pharmacodynamic Profile of AG-120, a Potent Inhibitor of the IDH1 Mutant Protein, in a Phase 1 Study of IDH1-Mutant Advanced Hematologic Malignancies, American Society of Hematology, 57th Annual Meeting & Exposition, Orlando, FL, Abstract 1310, 2 pages (Dec. 508, 2015). URL: https://ash.confex.com/ash/2015/webprogramscheduler/Paper82908.html [Retrieved Jun. 7, 2018].
Fan, B. et al., Longitudinal Pharmacokinetic/Pharmacodynamic Profile of AG-120, a Potent Inhibitor of the IDH1 Mutant Protein, in a Phase 1 Study of IDH1-Mutant Advanced Hematologic Malignancies, Blood, 126(23): 1310-1310 (2015).
Fan, B. et al., Longitudinal pharmacokinetic/pharmacodynamic profile of AG-120, a potent inhibitor of the IDH1 mutant protein, in a phase 1 study of IDH1-mutant advanced hematologic malignancies, Poster 1310, Presented at the 57th American Society of Hematology Annual Meeting and Exposition, Orlando, FL, 1 page (Dec. 5, 2015).
Fan, B. et al., Pharmacokinetic/pharmacodynamic (PK/PD) profile of AG-120 in patients with IDH1-mutant cholangiocarcinoma from a phase 1 study of advanced solid tumors, Poster 4082, Presented at the American Society of Clinical Oncology (ASCO) Annual Meeting, Chicago, IL, USA, 1 page (Jun. 3, 2017).
Fan, B. et al., Pharmacokinetic/Pharmacodynamic (PK/PD) Profile of AG-120 in Patients with IDH1-Mutant Cholangiocarcinoma from a Phase 1 Study of Advanced Solid Tumorsm, Journal of Clinical Oncology, 35(15_suppl): 4082-4082 (May 20, 2017).
Fan, B. et al., Pharmacokinetic/pharmacodynamic evaluation of AG-120, a potent inhibitor of the IDH1 mutant protein, in a phase 1 study of IDH1-mutant advanced hematologic malignancies, Poster P572, Presented at the 20th Congress of the European Hematology Association, Vienna, Austria, 1 page (Jun. 13, 2015).
Fan, B. et al., Pharmacokinetics/pharmacodynamics (PK/PD) of ivosidenib in patients with IDH1-mutant advanced solid tumors from a phase 1 study, 2018 ASCO Annual Meeting, J Clin Oncol., 36 (Abstract 2577), 1 page (Jun. 4, 2018). URL: https://meetinglibrary.asco.org/record/158587/abstract [Retrieved Jun. 7, 2018].
Ghazanchyan, T. et al., Developing a Genomics Model to Predict Failure of Isocitrate Dehydrogenase (IDH) Inhibitors for Treatment of Patients with IDH1- or IDH2-Mutated Acute Myeloid Leukemia, 2018 ASH Annual Meeting, Blood, 132: Abstract 2815 (2018).
Ishii, Y. et al., Abstract A071: AG-120 (ivosidenib), a first-in-class mutant IDH1 inhibitor, promotes morphologic changes and upregulates liver-specific genes in IDH1 mutant cholangiocarcinoma, Cellular Responses to Therapy, AACR-NCI-EORTC International Conference on Molecular Targets and Cancer Therapeutics, Oct. 26,-30, 2017, Philadelphia, PA, 3 pages (Published Jan. 2018).
Le, K. et al., Population Pharmacokinetics of Ivosidenib (AG-120) in Patients with IDH1-Mutant Advanced Hematologic Malignancies, 2018 ASH Annual Meeting, Blood, 132: Abstract 1394 (2018).
Le, K. et al., Population Pharmacokinetics of Ivosidenib (AG-120) in Patients with IDH1-Mutant Advanced Hematologic Malignancies, Poster, 2018 ASH Annual Meeting, 132: Abstract 1394 (2018).
Lowery, M.A et al., A phase 3, multicenter, randomized, double-blind study of AG-120 vs placebo in patients with an advanced cholangiocarcinoma with an IDH1 mutation, ASCO Annual Meeting 2017, J Clin Oncol, 35: suppl; Abstract TPS4142 (2017).
Lowery, M.A. et al., Phase I study of AG-120, an IDH1 mutant enzyme inhibitor: Results from the cholangiocarcinoma dose escalation and expansion cohorts, Abstract 4015, Journal of Clinical Oncology, 35 (15 Suppl): 4015-4015 (May 20, 2017). URL: http://ascopubs.org/doi/abs/10.1200/JCO.2017.35.15_suppl.4015 [Retrieved Mar. 21, 2018].
Ma, R. and Yun, C. H., Crystal structures of pan-IDH inhibitor AG-881 in complex with mutant human IDH1 and IDH2, Biochem Biophys Res Commun, 503(4): 2912-2917 (2018).
Mellinghoff, I.K. et al., Phase 1 study of AG-881, an inhibitor of mutant IDH1/IDH2, in patients with advanced IDH-mutant solid tumors, including glioma, 2018 ASCO Annual Meeting, J Clin Oncol., 36: (Abstract 2002), 2 pages (Jun. 1, 2018). URL: https://meetinglibrary.asco.org/record/162680/abstract [Retrieved Jun. 7, 2018].
Pollyea, D.A. et al., Ivosidenib (IVO; AG-120) in mutant IDH1 relapsed/refractory acute myeloid leukemia (R/R AML): Results of a phase 1 study, 2018 ASCO Annual Meeting, J Clin Oncol., 36 (Abstract 7000), 2 pages (Jun. 2, 2018). URL: https://meetinglibrary.asco.org/record/161682/abstract [Retrieved Jun. 7, 2018].
Popovici-Muller, J. et al., Discovery of AG-120 (Ivosidenib): A First-in-Class Mutant IDH1 Inhibitor for the Treatment of IDH1 Mutant Cancer, ACS Med. Chem. Lett., 9(4): 300-305 (2018).
Roboz, G.J. et al., Ivosidenib (AG-120) Induced Durable Remissions and Transfusion Independence in Patients with IDH1-Mutant Untreated AML: Results from a Phase 1 Dose Escalation and Expansion Study, ASH Annual Meeting, Blood, 132: Abstract 561 (2018).
Roboz, G.J. et al., Ivosidenib (AG-120) Induced Durable Remissions and Transfusion Independence in Patients with IDH1-Mutant Untreated Aml: Results from a Phase 1 Dose Escalation and Expansion Study, Presentation, Presented at the 60th American Society of Hematology (ASH) Annual Meeting, Dec. 1-4, 2-18, San Diego, CA, USA, 16 pages, Abstract 561 (2018).
Stein, E. et al., AGILE: A phase 3, multicenter, randomized, placebo-controlled study of ivosidenib in combination with azacitidine in adult patients with previously untreated acute myeloid leukemia with an IDH1 mutation, Journal of Clinical Oncology, 36(15 suppl): Abstract TPS7074 (2018).
Stein, E. et al., AGILE: A phase 3, multicenter, randomized, placebo-controlled study of ivosidenib in combination with azacitidine in adult patients with previously untreated acute myeloid leukemia with an IDH1 mutation, Presented at the American Society of Clinical Oncology (ASCO) Annual Meeting, Chicago, IL, USA, Abstract TPS7074, J Clin Oncol 36, 2018 (Jun. 1-5, 2018).
Stein, E.M. et al., Ivosidenib or Enasidenib Combined with Induction and Consolidation Chemotherapy in Patients with Newly Diagnosed AML with an IDH1 or IDH2 Mutation is Safe, Effective,

(56) References Cited

OTHER PUBLICATIONS and Leads to MRD-Negative Complete Remissions, Poster Presented at the 60th American Society of Hematology (ASH) Annual Meeting, Dec. 1-4, 2018, San Diego, CA, USA, 21 pages, Abstract 560 (2018).
Stein, E.M. et al., Ivosidenib or Enasidenib Combined with Standard Induction Chemotherapy is Well Tolerated and Active in Patients with Newly Diagnosed AML with an IDH1 or IDH2 Mutation: Initial Results from a Phase 1 Trial, 2017 ASH Annual Meeting, Blood, 130: Abstract 726 (2017).
Stone, R.M. et al., Genetic Profiling and Deep IDH1 Mutation Clearance to =0.04 in Ivosidenib (AG-120)-Treated Patients with Mutant IDH1 Relapsed or Refractory and Untreated AML, 2017 ASH Annual Meeting, Blood, 130: Abstract 2684 (2017).
Thompson, C.B., Metabolic Enxymes as Oncogenes or Tumor Suppressors, N Engl J Med, 360(8): 813-815 (2009).
Watanabe, T. et al., IDH1 Mutations are early events in the Development of Astrocytomas and Oligodendrogliomas, American Journal of Pathology, 174(4): 1149-1153 (2009).
Yen, K. et al., Abstract 4956: Functional characterization of the ivosidenib (AG-120) and azacitidine combination in a mutant IDH1 AML cell model, Experimental and Molecular Therapeutics, Proceedings: AACR Annual Meeting 2018; Apr. 14-18, 2018; Chicago, IL (Published Jul. 2018).
Yen, K. et al., Abstract B126: AG-881, a brain penetrant, potent, pan-mutant IDH (mIDH) inhibitor for use in mIDH solid and hematologic malignancies, AACR-NCI-EORTC International Conference: Molecular Targets and Cancer Therapeutics (Oct. 26-30, 2017; Philadelphia, PA).
Caira, M.R. et al., Crystalline polymorphism of organic compounds, Topics in Current Chemistry, 198: 163-208 (1998).
International Search Report for PCT/US2019/032742, 4 pages (dated Jul. 29, 2019).
International Search Report for PCT/US2019/032747, 5 pages (dated Aug. 1, 2019).
Lin, J. et al., Discovery and Optimization of Quinoline Derivatives as Potent, Selective, and Orally Bioavailable Mutant Isocitrate Dehydrogenase 1 Inhibitors. J. Med. Chem., 65 pages (2019).
Olutasidenib, C18H15CIN4O2, PubChem, Compound Summary, 10 pages (retrieved Jul. 24, 2019).
U.S. Appl. No. 16/893,147, filed Sep. 24, 2020, Kelly et al.
Blackburn, C. et al., Identification and characterization of aminopiperidinequinolones and quinazolinones as MCHr1 antagonists, Bio. and Med. Chem. Letters, 16(10):2621-2627 (2006).
Cortes, J.E. et al., Olutasidenib (FT-2102) Induces Rapid Remissions in Patients with IDH1-Mutant Myelodysplastic Syndrome: Results of Phase 1/2 Single Agent Treatment and Combination with Azacitidine, ASH Annual Meeting, Oral Presentation, 12 pages (Dec. 9, 2019).
De La Fuente, M. et al., A Phase 1 b/2 Study of Olutasidenib in Patients with Relapsed/Regractory IDH1 Mutant Gliomas: Safety and Clinical Activity as a Single Agent and in Combination with Azacitidine, ASCO, slides 1-13, May 2020.
De La Fuente, M.I. et al., A phase ib/II study of olutasidenib in patentis with relapsed/refractory IDH1 mutant gliomas: Safety and efficacy as single agent and in combination with azacitidine, Amer. Soc. Clin. Oncol. (2020), Abstract, <https://meetinglibrary.asco.org/record/185065/abstract>. Retrieved on May 13, 2020.
Golub, D. et al., Mutant Isocitrate Dehydrogenase Inhibitors as Targeted Cancer Therapeutics, Front. Oncol., Article 417, 1-25 (2019).
Huang, J. et al., Isocitrate Dehydrogenase Mutations in Glioma: From Basic Discovery to Therapeutics Development, Front. Oncol., Article 506, 9:1-7 (2019).
Jones, R.L. et al., A phase ib/II study of olutasidenib in patients with relapsed/refractory IDH1 mutant solid tumors: Safety and efficacy as single agent, Amer. Soc. Clin. Oncol. (2020), Abstract, <https://meetinglibrary.asco.org/record/186633/abstract>. Retrieved on May 13, 2020.

Megias-Vericat, J.E., et al., IDHI-mutated relapsed or refractory AML: current challenges and future prospects, Blood and Lymphatic Cancer: Targets and Therapy, 9:19-32 (2019).
Press Release, Forma Therapeutics Announces Clinical Data to be Presented at ASCO20 Virtual Scientific Program (2020), Forma Therapeutics, <https://www.formatherapeutics.com/press-releases/forma-therapeutics-announces-clinical-data-to-be-presented-at-asco20-virtual-scientific-program>. Retrieved Jun. 5, 2020.
Reitman, Z.J. and Yan, H, Isocitrate Dehydrogenase 1 and 2 Mutations in Cancer: Alterations at a Crossroads of Cellular Metabolism, J. Natl. Cancer Inst., 102:932-941 (2010).
Wai, J. et al., Synthesis and evaluation of 2-pyridinone derivatives as specific HIV-1 reverse transcriptase inhibitors. 3. Pyridyl and phenyl analogs of 3-aminopyridin-2(1H)-one, J. Med. Chem., 36(2):249-255 (1993).
Watts, J.M. et al., Olutasidenib (FT-2102), an IDH1m Inhibitor as a Single Agent or in Combination with Azacitidine, Induces Deep Clinical Responses with Mutation Clearance in Patients with Acute Myeloid Leukemia Treated in a Phase 1 Dose Escalation and Expansion Study, ASH Annual Meeting, Oral Presentation, 14 pages (Dec. 7, 2019).
Abbott Molecular Inc, U.S. Food and Drug Administration Approval Letter, 4 pages (2018), <https://www.accessdata.fda.gov/cdrh_docs/pdf17/P170041A.pdf> [Retrieved Jul. 28, 2020].
Abbott Molecular Inc., Summary of Safety and Effectiveness Data (SSED), 43 pages (2018), <https://www.accessdata.fda.gov/cdrh_docs/pdf17/P170041B.pdf> [Retrieved Jul. 28, 2020].
Agios Pharmaceuticals, Press Release, Celgene and Agios Announce Collaborations with Abbott for Diagnostic Identification of IDH Mutations in AML, 4 pages (Summit, N.J. and Cambridge, Mass., Oct. 12, 2016). URL: <https://investor.agios.com/news-releases/news-release-details/celgene-and-agios-announce-collaborations-abbott-diagnostic> [Retrieved Jul. 28, 2020].
Agios Pharmaceuticals, Press Release, FDA Accepts New Drug Application and Grants Priority Review for Ivosidenib in Relapsed or Refractory AML with an IDH1 Mutation, 4 pages (Summit, N.J. and Cambridge, Mass., Feb. 15, 2018). URL: <https://investor.agios.com/news-releases/news-release-details/fda-accepts-new-drug-application-and-grants-priority-review-0> [Retrieved Jul. 28, 2020].
Agios Pharmaceuticals, Press Release, FDA Grants Approval of Tibsovo®, the First Oral, Targeted Therapy for Adult Patients with Relapsed/Refractory Acute Myeloid Leukemia and an IDH1 Mutation , 9 pages (Cambridge, Mass., Jul. 20, 2018). URL: <https://investor.agios.com/news-releases/news-release-details/fda-grants-approval-tibsovor-first-oral-targeted-therapy-adult> [Retrieved Jul. 28, 2020].
Gu, X. et al., MicroRNA-129-5p inhibits human glioma cell proliferation and induces cell cycle arrest by directly targeting DNMT3A, Am. J. Transl. Res., 10(9):2834-2847 (2018).
International Search Report for PCT/US2020/033212, 6 pages (dated Jul. 20, 2020).
Lin, J. et al., Discovery and Optimization of Quinolinone Derivatives as Potent, Selective, and Orally Bioavailable Mutant Isocitrate Dehydrogenase 1 (mIDH1) Inhibitors, J. Med. Chem., 62(14):6575-6596 (2019).
Metzker, M., Sequencing technologies—the next generation, Nature Review Genetics, 11:31-46 (2010).
U.S. Appl. No. 16/414,505 Non-Final Rejection, 15 pages (dated Jul. 7, 2020).
U.S. Appl. No. 16/526,593 Non-Final Rejection, 32 pages (dated Jun. 15, 2020).
U.S. Appl. No. 16/693,585 Non-Final Rejection, 16 pages (dated Sep. 2, 2020).
Yu, J. et al., Clinical implications of recurrent gene mutations in acute myeloid leukemia, Exp. Hematol. Oncol., 9:1-11 (2020).
U.S. Appl. No. 16/414,505 Response to Non-Final Rejection, 17 pages (filed Mar. 3, 2020).
U.S. Appl. No. 16/414,505 Response to Non-Final Rejection, 17 pages (filed Nov. 25, 2019).
U.S. Appl. No. 16/526,593 Notice of Allowance, 9 pages (dated Sep. 8, 2020).
U.S. Appl. No. 16/526,593 Response to Non-Final Rejection, 13 pages (filed Aug. 26, 2020).

(56) References Cited

OTHER PUBLICATIONS

U.S. Appl. No. 16/693,585 Response to Non-Final Rejection, 16 pages (filed Sep. 23, 2020).
U.S. Appl. No. 16/526,593, filed Nov. 21, 2019, Kelly et al.
Abbott RealTime IDH1 label, Reference No. 08N90-090, 31 pages (Jul. 2018); accessed on Jul. 29, 2019 from https://www.fda.gov/medical-devices/vitro-diagnostics/list-cleared-or-approved-companion-diagnostic-devices-vitro-and-imaging-tools.
Cancer Genome Atlas Research Network, Comprehensive, Integrative Genomic Analysis of Diffuse Lower-Grade Gliomas, N Engl J Med, 372: 2481-2498 (2015).
ClinicalTrials.gov Identifier: NCT02073994, Study of Orally Administered AG-120 in Subjects With Advanced Solid Tumors, Including Glioma, With an IDH1 Mutation, First Posted Feb. 28, 2014; Last Update Posted Jun. 4, 2019. https://clinicaltrials.gov/ct2/show/NCT02073994?term=NCT02073994&rank=1.
ClinicalTrials.gov Identifier: NCT02481154, Study of Orally Administered AG-881 in Patients With Advanced Solid Tumors, Including Gliomas, With an IDH1 and/or IDH2 Mutation, First Posted Jun. 25, 2015; Last Update Posted Jun. 6, 2019. https://clinicaltrials.gov/ct2/show/NCT02481154?term=NCT02481154&rank=1.
ClinicalTrials.gov Identifier: NCT03343197, Study of AG-120 and AG-881 in Subjects With Low Grade Glioma, First Posted Nov. 17, 2017; Last Update Posted Jul. 23, 2018. https://clinicaltrials.gov/ct2/show/NCT03343197?term=NCT03343197&rank=1.
Cortes, J.E. et al., FT-2102, an IDH1m Inhibitor, Combined with Azacitidine in Patients with Acute Myeloid Leukemia (AML) or Myelodysplastic Syndrome (MDS): Results from a Phase 1 Study, Poster EHA-3328, Presented at the 24th Annual Congress of the European Hematology Association, Amsterdam, Netherlands, Jun. 14, 2019.
De Botton, S. et al., FT-2102, an IDH1m Inhibitor, Induces Mutation Clearance in Patients with Acute Myeloid Leukemia (AML) or Myelodysplastic Syndrome (MDS) Treated in Phase 1 Dose Escalation and Expansion Study, Poster EHA-3251, Presented at the 24th Annual Congress of the European Hematology Association, Amsterdam, Netherlands, Jun. 15, 2019.
Emadi, A. et al., Presence of isocitrate dehydrogenase mutations may predict clinical response to hypomethylating agents in patients with acute myeloid leukemia, Am. J. Hematol., 90: E77-E79, (2015).
Leese, C. L. and Rydon, H.N., Polyazanaphthalenes. Part I. Some derivatives of 1:4:5-triazanaphthalene and quinoxaline, PolyJournal of the Chemical Society, 303-309 (1995).
Mamedov, V. A. et al., Synthesis and Functionalization of 3-Ethylquinoxalin-2(1H)-one, Russian Journal of Organic Chemistry, 41(4): 599-606 (2005).
Mellinghoff, I. et al., 2017 SNO Annual Meeting: Presentation ACTR-46.
Mellinghoff, I. et al., Phase 1 study of AG-881, an inhibitor of mutant IDH1 and IDH2: results from the recurrent/progressive glioma population, Presentation ACTR-31, 23rd Annual Scientific Meeting and Education Day of the Society for Neuro-oncology (SNO), Nov. 15-18, 2018, New Orleans, LA, USA (2018).
Mellinghoff, I.K. et al., A phase 1, open-label perioperative study of ivosidenib (AG-120) and vorasidenib (AG-881) in recurrent, IDH1-mutant, low-grade glioma: Results from Cohort 1, Presented at the American Society of Clinical Oncology (ASCO) Annual Meeting, May 21-Jun. 3, 2019, Chicago, IL, USA.
Nicolay, B. et al., Combined use of the pan-IDH mutant inhibitor AG-881 with radiation therapy shows added benefit in an orthotopic IDH1 mutant glioma model in vivo, Poster EXTH-34, Presented at the 22nd Annual Scientific Meeting and Education Day of the Society for Neuro-oncology, Nov. 16-19, 2017, San Francisco, CA, USA (2017).
Nicolay, B. et al., The IDH1 mutant inhibitor AG-120 shows strong inhibition of 2-HG production in an orthotopic IDH1 mutant glioma model in vivo, EXTH -59, Presented at the 22nd Annual Scientific Meeting and Education Day of the Society for Neuro-oncology, Nov. 16-19, 2017, San Francisco, CA, USA (2017).

Szopa, W. et al., Diagnostic and Therapeutic Biomarkers in Glioblastoma: Current Status and Future Perspectives, BioMed Res. Inter., 1-14 (2017).
U.S. Appl. No. 16/693,585 Non-Final Rejection, 30 pages (dated Nov. 20, 2020).
U.S. Appl. No. 16/893,147 Non-Final Rejection, 41 pages (dated Nov. 30, 2020).
U.S. Appl. No. 16/712,951, filed Jul. 16, 2020, Lin et al.
Caravella, J. A. et al., Structure-based design and identification of FT-2102 (olutasidenib), a potent mutant-selective IDH1 inhibitor, J Med Chem, doi: 10.1021/acs.jmedchem.9b01423, Epub ahead of print (2020).
Cortes, J.E. et al., Olutasidenib (FT-2102) Induces Rapid Remissions in Patients with IDH1-Mutant Myelodysplastic Syndrome: Results of Phase 1/2 Single Agent Treatment and Combination with Azacitidine, ASH Annual Meeting, Oral and Poster Abstract, Abstract 674 (Dec. 9, 2019).
De La Fuente, M.I. et al., Phase 1b/2 Study of Olutasidenib (FT-2102), an Inhibitor of Mutant IDH1, in Patients with Relapsed/Refractory IDH1-Mutant Gliomas: Preliminary Safety and Clinical Activity, Presented at the Society for NeuroOncology, Phoenix, AZ, Nov. 20-24, 2019 (Presented on Nov. 21, 2019).
Ribadeneira, M. et al., SCIDOT-42. FT-2102—a Potent and Selective Brain Penetrant Inhibitor of Mutant Isocitrate Dehydrogenase, Neuro-Oncology, 21(Supplement 6): vi280 3 pages (2019).
Seltzer, M.J. et al., Inhibition of Glutaminase Preferentially Slows Growth of Glioma Cells with Mutant IDH1, Cancer Research, 70(22): 8981-8987 (2010).
U.S. Appl. No. 16/414,505 Final Rejection, 8 pages (dated Jan. 16, 2020).
U.S. Appl. No. 16/414,505 Non-Final Rejection, 11 pages (dated Aug. 26, 2019).
Watts, J.M. et al., Olutasidenib (FT-2102), an IDH1m Inhibitor as a Single Agent or in Combination with Azacitidine, Induces Deep Clinical Responses with Mutation Clearance in Patients with Acute Myeloid Leukemia Treated in a Phase 1 Dose Escalation and Expansion Study, ASH Annual Meeting, Oral and Poster Abstract, Abstract 231 (Dec. 7, 2019).
Wick, W. et al., New (alternative) temozolomide regimens for the treatment of glioma, Neuro-Oncology, 11:69-79 (2009).
Bleeker, F.E. et al., IDH1$^{R132}$ mutations occur frequently in high-grade gliomas but not in other solid tumors, Human Mutation, 30:84-91 (2009).
ClinicalTrials.gov Identifier: NCT00900224, "Studying Tissue and Blood Samples From Patients with Acute Myeloid Leukemia," (v40 dated Dec. 15, 2010; update posted Dec. 16, 2010) https://clinicaltrials.gov/ct2/history/NCT00900224?V_40=View.
Struys, E.A. et al., Mutations in the D-2-Hydroxyglutarate Dehydrogenase Gene Cause D-2-Hydroxyglutaric Aciduria, Am. J. Hum. Genet., 76:358-360 (2005).
TIBSOVO Prescription Label, 20 pages (issued Jul. 20, 2018), <https://www.accessdata.fda.gov/drugsatfda_docs/label/2018/211192s000lbl.pdf>.
U.S. Appl. No. 17/112,269, Kelly et al.
U.S. Appl. No. 17/055,278, Kelly et al.
A Study of FT-2012 in Patients with Advanced Solid Tumors and Gliomas, Spanish Clinical Studies Registry, retrieved from https://reec.aemps.es/reec/public/detail.html, 16 pages (2019).
AbbVie, AbbVie Receives EMA and FDA Orphan Drug Designation for Investigational Compound ABT-414 in the Treatment of Glioblastoma Multiforme, 4 pp. (Aug. 4, 2014). URL: https://www.prnewswire.com/news-releases/abbvie-receives-ema-and-fda-orphan-drug-designation-for-investigational-compound-abt-414-in-the-treatment-of-glioblastoma-multiforme-269807321.html.
AbbVie, AbbVie Receives U.S. FDA Rare Pediatric Disease Designation for Investigational ABT-414 for the Treatment of a Type of Pediatric Brain Tumor known as Diffuse Intrinsic Pontine Glioma (DIPG), 3 pages (Jul. 11, 2016). URL:https://news.abbvie.com/article_print.cfm?article_id=11360.
Agios Pharmaceuticals, Press Release, Agios Presents Updated Data from Phase 1 Dose-Escalation Study of AG-881 in Patients with IDH Mutant Positive Advanced Glioma, 6 pages (Nov. 16, 2018).

(56) References Cited

OTHER PUBLICATIONS

URL: https://investor.agios.com/news-releases/news-release-details/agios-presents-updated-data-phase-1-dose-escalation-study-ag-881.
Agios Pharmaceuticals, Third Quarter 2018 Financial Results, 27 pages (Nov. 1, 2018).
Agios Pharmaceuticals, TIBSOVO® (ivosidenib) FDA Approval, 17 pages (Jul. 20,2018).
Bayer, Interim Report Third Quarter of 2018, 61 pages (2018).
ClinicalTrials.gov Identifier: NCT01800695, Evaluating the Safety and Pharmacokinetics of ABT-414 for Subjects With Glioblastoma Multiforme (First Posted Feb. 28, 2013, Last Update Posted Nov. 21, 2017). URL:https://clinicaltrials.gov/ct2/show/NCT01800695.
ClinicalTrials.gov Identifier: NCT02073994, Study of Orally Administered AG-120 in Subjects With Advanced Solid Tumors, Including Glioma, With an IDH1 Mutation (First Posted Feb. 28, 2014, Last Update Posted Dec. 9, 2020). URL: https://clinicaltrials.gov/ct2/show/NCT02073994.
ClinicalTrials.gov Identifier: NCT02074839, Study of Orally Administered AG-120 in Subjects With Advanced Hematologic Malignancies With an IDH1 Mutation (First Posted Feb. 28, 2014, Last Update Posted Feb. 5, 2020). URL: https://clinicaltrials.gov/ct2/show/NCT02074839?term=NCT02074839&draw=2&rank=1.
ClinicalTrials.gov Identifier: NCT02193347, IDH1 Peptide Vaccine for Recurrent Grade II Glioma (Resist) (First Posted Jul. 17, 2014, Last Update Posted May 13, 2020). URL: https://clinicaltrials.gov/ct2/show/NCT02193347.
ClinicalTrials.gov Identifier: NCT02481154, Study of Orally Administered AG-881 in Patients With Advanced Solid Tumors, Including Gliomas, With an IDH1 and/or IDH2 Mutation (First Posted Jun. 25, 2015, Last Update Posted Dec. 17, 2020). URL: https://clinicaltrials.gov/ct2/show/NCT02481154.
ClinicalTrials.gov Identifier: NCT02492737, Study of Orally Administered AG-881 in Patients With Advanced Hematologic Malignancies With an IDH1 and/or IDH2 Mutation (First Posted Jul. 9, 2015, Last Update Posted Mar. 8, 2019). URL: https://clinicaltrials.gov/ct2/show/NCT02492737?term=NCT02492737&draw=2&rank=1.
ClinicalTrials.gov Identifier: NCT02511405, A Phase 3, Pivotal Trial of VB-111 Plus Bevacizumab vs. Bevacizumab in Patients With Recurrent Glioblastoma (Globe) (Globe) (First Posted Jul. 30, 2015, Last Update Posted Oct. 23, 2018). URL: https://clinicaltrials.gov/ct2/show/NCT02511405?term=VB-111.
ClinicalTrials.gov Identifier: NCT02573324, A Study of ABT-414 in Participants With Newly Diagnosed Glioblastoma (GBM) With Epidermal Growth Factor Receptor (EGFR) Amplification (Intellance1) (First Posted Oct. 9, 2015, Last Update Posted Dec. 21, 2020). URL: https://clinicaltrials.gov/ct2/show/NCT02573324?term=ABT-414&rank=6.
ClinicalTrials.gov Identifier: NCT02677922, A Safety and Efficacy Study of Oral AG-120 Plus Subcutaneous Azacitidine and Oral AG-221 Plus Subcutaneous Azacitidine in Subjects With Newly Diagnosed Acute Myeloid Leukemia (AML) (First Posted Feb. 9, 2016, Last Update Posted Dec. 20, 2019). URL: https://clinicaltrials.gov/ct2/show/NCT02677922.
ClinicalTrials.gov Identifier: NCT02746081, Phase I Study of BAY1436032 in IDH1-mutant Advanced Solid Tumors (First Posted Apr. 21, 2016, Last Update Posted Dec. 22, 2020). URL: https://clinicaltrials.gov/ct2/show/NCT02746081.
ClinicalTrials.gov Identifier: NCT02771301, Safety and Efficacy of IDH1R132H-DC Vaccine in Gliomas (First Posted May 13, 2016, Last Update Posted May 13, 2016). URL: https://clinicaltrials.gov/ct2/show/NCT02771301.
ClinicalTrials.gov Identifier: NCT02989857, Study of AG-120 in Previously Treated Advanced Cholangiocarcinoma With IDH1 Mutations (ClarIDHy) (ClarIDHy) (First Posted Dec. 12, 2016, Last Update Posted Dec. 1, 2020). URL: https://clinicaltrials.gov/ct2/show/NCT02989857.
ClinicalTrials.gov Identifier: NCT03030066, Study of DS-1001b in Patients With Gene IDH1-Mutated Gliomas (First Posted Jan. 24, 2017, Last Update Posted Feb. 28, 2020). URL: https://clinicaltrials.gov/ct2/show/NCT03030066.
ClinicalTrials.gov Identifier: NCT03149575, VAL-083 Phase 3 Study in Temozolomide-Avastin (Bevacizumab) Recurrent GBM (STAR-3) (First Posted May 11, 2017, Last Update Posted Nov. 14, 2019). URL: https://clinicaltrials.gov/ct2/show/NCT03149575?term=VAL-083&rank=6.
ClinicalTrials.gov Identifier: NCT03173248, Study of AG-120 (Ivosidenib) vs. Placebo in Combination With Azacitidine in Patients With Previously Untreated Acute Myeloid Leukemia With an IDH1 Mutation (Agile) (First Posted Jun. 1, 2017, Last Update Posted Dec. 24, 2020). URL: https://www.clinicaltrials.gov/ct2/show/NCT03173248.
ClinicalTrials.gov Identifier: NCT03343197, Study of AG-120 and AG-881 in Subjects With Low Grade Glioma (First Posted Nov. 17, 2017, Last Update Posted Oct. 5, 2020). URL: https://clinicaltrials.gov/ct2/show/NCT03343197.
ClinicalTrials.gov Identifier: NCT03393000, Safety and Efficacy Study of Trans Sodium Crocetinate (TSC) in Newly Diagnosed Glioblastoma (GBM) Biopsy-Only Subjects (Intact) (First Posted Jan. 8, 2018, Last Update Posted Jan. 28, 2020). URL: https://clinicaltrials.gov/ct2/show/record/NCT03393000?term=trans+sodium+crocetinate&rank=1&view=record.
ClinicalTrials.gov Identifier: NCT03398655, A Study of VB-111 With Paclitaxel vs Paclitaxel for Treatment of Recurrent Platinum-Resistant Ovarian Cancer (Oval) (Oval) (First Posted Jan. 12, 2018, Last Update Posted Jan. 1, 2021). URL: https://clinicaltrials.gov/ct2/show/NCT03398655?term=VB-111.
DelMar Pharmaceuticals, Inc., DelMar Pharmaceuticals Announces Fast Track Designation for VAL-083 in Recurrent Glioblastoma, 5 pages (Dec. 26, 2017).
Gainer, J.L. et al., Trans sodium crocetinate with temozolomide and radiation therapy for glioblastoma multiforme, J. Neurosurg, 126:460-466 (2017).
Gormley, G., Research and Development at Daichii Sankyo, Daiichi-Sankyo, 70 pages (2014). URL: https://www.daiichisankyo.com/files/news/ir/pdf/005258/R&D%20Day_eng.pdf.
Gruslove, A. et al., VB-111: a novel anti-vascular therapeutic for glioblastoma multiforme, J Neurooncol., 124(3):365-372 (2015).
Katz, A., Novel Alkylating Agent Defies Mechanisms of Resistance in GBM Tumors, OncologyLive, 18(19): (Oct. 11, 2017).
Kintara Therapeutics, DelMar Presents Clinical Update on VAL-083 From Ongoing First-and Second-Line Trials in Patients with MGMT-unmethylated GBM at the Society for NeuroOncology Annual Meeting, 5 pages (Nov. 20, 2018). URL: https://www.kintara.com/news-media/press-releases/detail/887/delmar-presents-clinical-update-on-val-083-from-ongoing.
Mellinghoff, I.K. et al., A phase 1, multicenter, randomized, open-label, perioperative study of AG-120 (ivosidenib) and AG-881 in patients with recurrent, nonenhancing, IDH1-mutant, low-grade glioma, Presented at the 23rd Annual Scientific Meeting and Education Day of the Society for Neuro-oncology (Sno), New Orleans, LA, USA, Poster RBTT-03 (Nov. 15-18, 2018).
Mellinghoff, I.K. et al., AG-120, a first-in-class mutant IDH1 inhibitor in patients with recurrent or progressive IDH1 mutant glioma: results from the phase 1 glioma expansion cohorts, Presented at the Society for Neuro-Oncology Annual Scientific Meeting, Scottsdale, AZ, ACTR-46: 19 pages (Nov. 18, 2016).
Mohamed, H. and Duffy-Warren, F., Ft-2102—mIDH1 Inhibitor, Forma Therapeutics presentation, 4th Paediatric Strategy Forum for Medicinal Product Development for Acute Myeloid Leukaemia in Children and Adolescents, Erasmus University Rotterdam, 7 pages (Apr. 11, 2019).
Reardon, D.A. et al., Efficacy and safety results of Abt-414 in combination with radiation and temozolomide in newly diagnosed glioblastoma, Neuro-Oncology, 19(7):965-975 (2016).
Ribadeneira, M.D. et al., Olutasidenib (FT-2102) A Potent and Selective Brain Penetrant Inhibitor of Mutant Isocitrate Dehydrogenase 1, Forma Therapeutics, Inc., Presented at 3rd SNO-SCIDOT Joint Conference on Therapeutic Delivery to the CNS, 9 pages (Nov. 20, 2019).

(56) References Cited

OTHER PUBLICATIONS

Shanley, M., Phase 3 Results Reveal Combination Therapy Does Not Improve Overall Survival in Glioblastoma, HCP Live, 2 pages (Mar. 8, 2018). Url: https://www.hcplive.com/view/vb-111-combination-glioblastoma-fail.

Study to evaluate FT-2012 as a single agent or in combination with Azacitidine or Cytarabine in patients with Acute Myeloid Leukemia or Myelodysplastic Syndrome, Spanish Clinical Studies Registry, retrieved from https://reec.aemps.es/reec/public/detail.html, 14 pages (2018).

The Brain Tumour Charity, Positive results from a drug treating recurrent glioblastoma, (Jun. 28, 2018) URL: https://news.abbvie.com/news/abbvie-receives-us-fda-rare-pediatric-disease-designation-for-investigational-abt-414-for-treatment-type-pediatric-brain-tumor-known-as-diffuse-intrinsic-pontine-glioma-dipg.htm.

U.S. Appl. No. 16/414,505 Response to Non-Final Rejection, 11 pages (filed Jan. 7, 2021).

U.S. Food and Drug Administration, FDA approves ivosidenib for relapsed or refractory acute myeloid leukemia, 2 pages (Content current as of Jan. 23, 2019). URL: https://www.fda.gov/drugs/resources-information-approved-drugs/fda-approves-ivosidenib-relapsed-or-refractory-acute-myeloid-leukemia.

U.S. Food and Drug Administration, ivosidenib, Treatment of acute myeloid leukemia (AML), 2 pages (Date Designated Jun. 9, 2015). URL: https://www.accessdata.fda.gov/scripts/opdlisting/oopd/detailedIndex.cfm?cfg ridkey=481515.

U.S. Food and Drug Administration, ivosidenib, Treatment of cholangiocarcinoma, 1 page (Date Designated Apr. 26, 2017). URL: https://www.accessdata.fda.gov/scripts/opdlisting/oopd/detailedIndex.cfm?cfgridkey=562216.

U.S. Food and Drug Administration, ivosidenib, Treatment of glioma, 1 pages (Date Designated. May 1, 2018). URL: https://www.accessdata.fda.gov/scripts/opdlisting/oopd/detailedIndex.cfm?cfgridkey=637718.

U.S. Food and Drug Administration, vorasidenib, Treatment of glioma, 1 page (Date Designated Sep. 10, 2018). URL: https://www.accessdata.fda.gov/scripts/opdlisting/oopd/detailedIndex.cfm?cfgridkey=649318.

VBL Therapeutics, Data Demonstrate Strengthened Overall Survival Benefit in Patients Treated With VB-111 in Combination With Bevacizumab, 4 pages (Jun. 1, 2015). URL: vblrx.com/vbl-therapeutics-reports-updated-interim-results-from-phase-2-clinical-trial-of-vb-111-in-recurrentglioblastoma-rgbm/.

VBL Therapeutics, VBL Therapeutics Announces Third Quarter 2018 Financial Results, 6 pages (Nov. 20, 2018). URL: https://www.globenewswire.com/news-release/2018/11/20/1654366/0/en/VBLTherapeutics-Announces-Third-Quarter-2018-Financial-Results.html.

U.S. Appl. No. 16/414,505 Final Rejection, 14 pages (dated Feb. 18, 2021).

U.S. Appl. No. 16/414,505 Final Rejection, 8 pages (dated Feb. 22, 2021).

\* cited by examiner

INHIBITING MUTANT ISOCITRATE DEHYDROGENASE 1 (MLDH-1)

CROSS-REFERENCE TO RELATED APPLICATIONS

This application claims the benefit of and priority to U.S. Provisional Application No. 62/701,487, filed Jul. 20, 2018; and U.S. Provisional Application No. US 62/712,160, filed Jul. 30, 2018; and
this application is a continuation-in-part of U.S. application Ser. No. 16/414,505, filed May 16, 2019, and International Application No. PCT/US19/32747, filed May 16, 2019, each of which claims the benefit of and priority to U.S. Provisional Application No. 62/672,461, filed May 16, 2018; U.S. Provisional Application No. 62/672,462, filed May 16, 2018; U.S. Provisional Application No. 62/680,566 filed Jun. 4, 2018; U.S. Provisional Application No. 62/680,571, filed Jun. 4, 2018; U.S. Provisional Application No. 62/680,560, filed Jun. 4, 2018; U.S. Provisional Application No. 62/680,562, filed Jun. 4, 2018; U.S. Provisional Application No. 62/692,598, filed Jun. 29, 2018; U.S. Provisional Application No. 62/692,601, filed Jun. 29, 2018; U.S. Provisional Application No. 62/692,604, filed Jun. 29, 2018; U.S. Provisional Application No. 62/692,605, filed Jun. 29, 2018; U.S. Provisional Application No. 62/692,591, filed Jun. 29, 2018, U.S. Provisional Application No. 62/773,562 filed Nov. 30, 2018; U.S. Provisional Application No. 62/798,677, filed Jan. 30, 2019; U.S. Provisional Application No. 62/798,681 filed Jan. 30, 2019; U.S. Provisional Application No. 62/798,684, filed Jan. 30, 2019; 62/798,687, filed Jan. 30, 2019; U.S. Provisional Application No. 62/798,690, filed Jan. 30, 2019; and U.S. Provisional Application No. 62/812,367, filed Mar. 1, 2019; and
this application is a continuation-in-part of U.S. application Ser. No. 16/414,716, filed May 16, 2019; and International Application No. PCT/US19/32742, filed May 16, 2019, each of which claims the benefit of and priority to U.S. Provisional Application No. 62/672,461, filed on May 16, 2018, U.S. Provisional Application No. 62/672,462, filed on May 16, 2018, and U.S. Provisional Application No. 62/692,591, filed on Jun. 29, 2018;
the contents of each of the applications listed above are hereby incorporated herein by reference in their entirety.

TECHNICAL FIELD

The present disclosure relates to the treatment of cancer. In particular, the present disclosure provides methods of treating patients diagnosed with a cancer harboring certain mutant IDH-1 cancer cells.

BACKGROUND

Dysregulation of metabolism is a common phenomenon in cancer cells. The NADP(+)-dependent isocitrate dehydrogenases 1 and 2 (IDH-1 and IDH-2) functionally modulate cellular metabolism in lipid synthesis, cellular defense against oxidative stress, oxidative respiration, and oxygen-sensing signal transduction. The presence of mutations in IDH-1 imparts a neomorphic activity to the enzyme, resulting in the production of (R)-2-hydroxyglutarate (2-HG), the downstream effects of which cause epigenetic changes that consequently block the proper differentiation of progenitor cells and lead to cancer. IDH-1 mutations have been reported in hematological malignancies, as well as many solid tumors types. By far the most frequent IDH-1 mutations occur at amino acid position R132, and include R132H, R132C, R132S, R132G, and R132L mutations.

Therapeutic compounds can be useful for inhibition of mutant IDH-1 and/or mutant IDH-2 cancer cells (mIDH-1 and mIDH-2) are being developed for the treatment of certain cancers. These therapies may also reduce elevated 2-HG levels in these cancer patients. Many different small molecule inhibitors of mutant isocitrate dehydrogenase (mIDH) proteins with neomorphic activity are disclosed in publications (e.g., WO2016/044789, WO2016/044787, WO2016/044782, WO2016/171755, and WO2016/171756), including testing of these compounds in IDH-1 R132H and IDH-1 R132C enzymatic assays, and cellular 2-HG assay using HCT116 mutant IDH-1 cells.

There remains a need for identifying therapeutic compounds that selectively inhibit the production of 2-HG from mIDH-1 cancer cells harboring R132 mutations including R132S, R132G and R132L. In addition, there remains a need for therapeutic compounds that selectively inhibit production of 2-HG from cancer cells harboring a variety of R132 IDH-1 mutations with clinically relevant comparative potencies, while remaining inactive at wild type IDH-1 cells. Preferably, a targeted, selective small molecule inhibitor of 2-HG production from mIDH-1 cancer cells is also inactive in mIDH-2 cancer cells that produce 2-HG. In addition, there is a need for inhibitors of the production of 2-HG from mIDH-1 cancer cells having a R132 mutation selected from the group consisting of: R132L, R132G, and R132S mutation in IDH-1.

SUMMARY

The present disclosure provides methods for treating cancer. In particular, patients diagnosed with cancer harboring a mutant IDH-1 cancer cell, e.g., having a IDH-1 R132 mutation selected from the group consisting of: R132L, R132G, and R132S (in addition to R132H and R132C IDH-1 mutations), can be treated with a therapeutically effective amount of Compound 1. In some examples, patients treated with Compound 1 can have a mutant IDH-1 cancer that does not have a mIDH-2 mutation detected with a FDA approved mIDH-2 diagnostic (e.g., as provided at www.fda.gov/CompanionDiagnostics).

The patient can be diagnosed with a cancer (e.g., a hematologic malignancy such as MDS or AML) characterized by the presence of a mutant allele of IDH1 (e.g., a mIDH1 selected from the group consisting of: R132L, R132G, and R132S) and a concurrent mutation selected from the group consisting of FLT3, NPM1, CEBPA and TP53. Preferably, the cancer is not characterized by an IDH2 mutation. The patient can be treated with a therapeutically effective amount of Compound 1 (preferably, 150 mg of Compound 1 administered twice per day, each day) throughout a course of treatment (preferably, at least 6 months) as a single agent or in combination with another agent for treating the cancer (e.g., azacitidine).

Compound 1 is a small molecule inhibitor of mutated forms of isocitrate dehydrogenase 1 (IDH-1) enzyme. Compound 1 targets the mutant IDH-1 variants R132L, R132G, and R132S at lower concentrations than the wild-type IDH-1 enzyme or mutant IDH-2 enzymes tested in vitro as disclosed herein. Compound 1 is useful for the treatment of adult patients diagnosed with cancer having an IDH-1 mutation as detected by an FDA-approved test. Compound 1 can be administered to patients in need thereof in a therapeutically effective amount (e.g., 150 mg orally twice daily until disease progression or unacceptable toxicity).

Patients for the treatment of cancer with Compound 1 can be selected based on the presence of IDH-1 mutations in the blood or bone marrow. In one embodiment, the recommended starting dose of Compound 1 is 150 mg taken orally twice daily with or without food until disease progression or unacceptable toxicity. For patients without disease progression or unacceptable toxicity, the patient can receive the therapeutically effective amount of Compound 1 for a minimum of 6 months to allow time for clinical response.

The invention is based in part on the discovery that Compound 1 selectively inhibits the production of 2-HG from mIDH-1 cancer cells harboring R132 mutations including R132S, R132G and R132L with clinically relevant comparative potencies, while remaining inactive at wild type IDH-1 cells. In addition, Applicants have discovered that Compound 1 is a targeted, selective small molecule inhibitor of 2-HG production from mIDH-1 cancer cells and is also inactive in mIDH-2 cancer cells that produce 2-HG (e.g., Compound 1 selectively inhibits the production of 2-HG from mIDH-1 cancer.

DEFINITIONS

Figure 1:
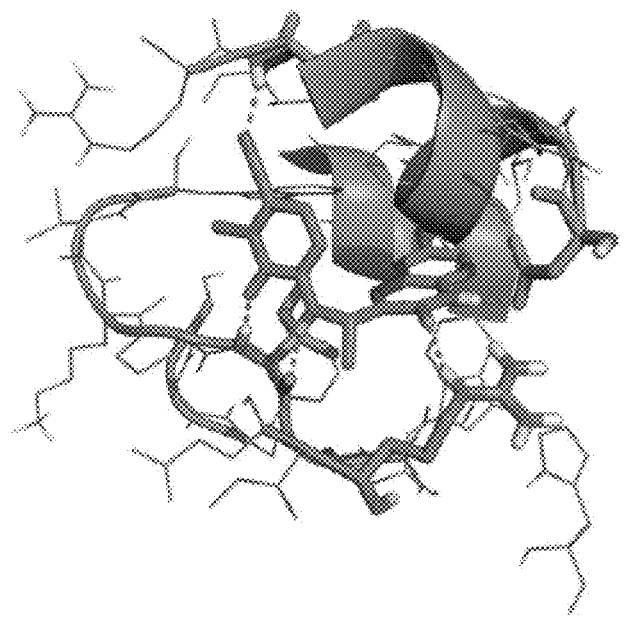
FIG. 1 illustrates Compound 1 binding with mIDH.

As used herein, the term "Course of Treatment" refers to the time period in which a patient is being administered an agent, including any administration holidays or recovery periods. A course of treatment can include a single treatment cycle or multiple treatment cycles. Additionally, a course of treatment can include a partial treatment cycle. The Course of Treatment can include the total time period during which a patient is on a treatment protocol for a disease, e.g. AML or MDS, with a therapy comprising the administration of a mIDH-1 inhibitor compound.

"Next-generation sequencing or NGS or NG sequencing" as used herein, refers to any sequencing method that determines the nucleotide sequence of either individual nucleic acid molecules (e.g., in single molecule sequencing) or clonally expanded proxies for individual nucleic acid molecules in a high-throughput fashion (e.g., greater than 103 or more molecules are sequenced simultaneously). Various next generation sequencing methods are known. In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) Nature Biotechnology Reviews 11:31-46, incorporated herein by reference. Next generation sequencing can detect a variant present in less than 5% of the nucleic acids in a sample. As shown in Example 7, for the purposes of Variant Allele Frequency analysis, digital droplet PCR (ddPCR) can also be used. ddPCR methods are known in the art, and are described in, e.g., Hindson B. J., et al. (2011). High-throughput droplet digital PCR system for absolute quantitation of DNA copy number. *Anal. Chem.* 83(22): 8604-8610, and Volegstein, B., et al. (1999) Digital PCR. *Proc. Natl. Acad. Sci. USA* 90: 9236-9241, incorporated herein by reference.

As used herein, the term "R132X mIDH-1 mutation(s)" refers to a mutation at the IDH-1 arginine 132 that results in inhibitory activity of Compound 1 against the mutated IDH-1 form harboring the R132 mutation. Preferably, the R132X mutations have a 2-HG IC50 value of less than 500 nM (most preferably less than 250 nM or less than 150 nM) using the in vitro assay of Example 1. Accordingly, preferred R132X mutations include R132H and R132C, as well as R132L, R132G, and R132S (or other R132X mutations having therapeutically relevant 2-HG IC50 values obtained using the in vitro assay of Example 1). Patients having R132X mIDH-1 mutation(s) can be identified using a suitable diagnostic, such as a diagnostic analyzing patient tissue with next generation sequencing technology that identified the presence of the R132X mIDH-1 mutation in the patient tissue sample.

As used herein, the term "R132X mIDH-1 Selective Inhibitor Therapy" refers to a therapy administered to a patient to inhibit the activity of R132X mIDH-1 in the patient, where the therapy is known to have selective inhibitory activity against R132X mIDH-1 over wild type IDH-1. An R132X mIDH-a selective inhibitor therapy can be administration of Compound 1 as disclosed herein.

As used herein, "sequencing" can be Next Generation Sequencing (NGS), a high-throughput sequencing technology that performs thousands or millions of sequencing reactions in parallel. Although the different NGS platforms use varying assay chemistries, they preferably generate sequence data from a large number of sequencing reactions run simultaneously on a large number of templates. The sequence data can be collected using a scanner, and then assembled and analyzed bioinformatically. Thus, the sequencing reactions are performed, read, assembled, and analyzed in parallel.

The terms "subject" and "patient" are used interchangeably in the present disclosure.

Susceptible IDH1 mutations are defined as those leading to increased levels of 2-hydroxyglutarate (2-HG) in the specified mIDH1 cancer cells (e.g., mIDH1 leukemia cells or mIDH1 glioma cells) and where efficacy is predicted by 1) clinically meaningful remissions with the recommended dose of Compound 1 and/or 2) inhibition of mutant IDH1 enzymatic activity at concentrations of Compound 1 sustainable at the recommended dosage according to validated methods. Susceptible mutations include R132H and R132C mIDH1 substitution mutations. In some methods, the susceptible IDH1 mutation leads to increased levels of 2-hydroxyglutarate (2-HG) in the leukemia cells. In some methods, efficacy of Compound 1 is predicted by a) clinically meaningful remissions with the recommended dose of Compound 1 and/or b) inhibition of mutant IDH1 enzymatic activity at concentrations of Compound 1 sustainable at the recommended dosage according to validated methods.

DETAILED DESCRIPTION

Compound 1 is a small molecule mIDH-1 inhibitor useful for the treatment of patients harboring IDH-1 mutations, in both hematologic and solid tumors.

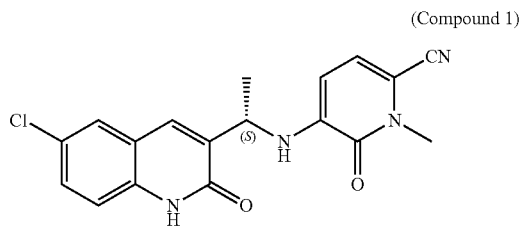

(Compound 1)

Compound 1 has potent and equivalent biochemical activity against a number of IDH-1 arginine 132 (R132) mutated forms, of which R132H and R132C are the most prevalent observed for human IDH-1. Compound 1 is a small molecule mIDH-1 (mutated isocitrate dehydrogenase 1) inhibitor. It is a permeable, orally bioavailable compound, with an excellent preclinical profile in both in vitro and in vivo models.

Isocitrate dehydrogenase (IDH) is a class of enzymes that catalyze the oxidative decarboxylation of isocitrate to α-keto-glutarate (α-KG). There are three isoforms in human cells. IDH-1 resides in the cytosol and peroxisomes, whereas IDH-2 and IDH-3 are mitochondrial enzymes. IDH-1 is dimeric and uses NADP+ as an electron acceptor. IDH-3 is a tetrameric enzyme and, in contrast, uses NAD+ as an electron acceptor. IDH-3 is the primary IDH enzyme participating in the Krebs cycle. The presence of the IDH-1 mutations imparts a neomorphic activity to the enzyme, resulting in the production of (R)-2-hydroxyglutarate (2-HG) which has been termed an "oncometabolite", and has pleotropic roles in tumorgenesis.

Studies in genetically engineered mouse models and models derived from cancer patient samples both support the discovery that mIDH produces 2-HG, the downstream effects of which cause epigenetic changes that consequently block the proper differentiation of progenitor cells and lead to cancer. In particular, IDH-1 mutations can lead to the loss of wild type enzymatic activity (conversion of isocitrate to alpha-KG (α-KG)). Instead, the mutated enzymes acquire the neomorphic activity of converting α-KG to 2-HG. In mIDH-1 harboring cancer cells, wild type and mutant IDH-1 form a heterodimeric complex that can produce very high 2-HG levels. All IDH-1 mutations result in the formation of the (R)-enantiomer of 2-HG, which is contrast to the accumulation of (S)-enantiomer found in L2-HG aciduria patients, who harbor homozygous loss-of-function mutations in 2-HG dehydrogenase. Given the structural similarity between 2-HG and α-KG, 2-HG has been shown to be a competitive inhibitor of a number of α-KG dependent histone and DNA demethylases. 2-HG inhibits several KDM family histone demethylases in vitro, including H3K9/H3K36 demethylases KDM4A and KDM4C, and H3K36 demethylase KDM2A. Furthermore, elevated methylation levels of H3K4, H3K9, H3K27, and H3K79 have been observed in mIDH-1 containing patient-derived samples, as well as in cells expressing IDH mutations or treated with a cell-permeable ester of 2-HG. 2-HG also inhibits the TET family of DNA demethylases, which in turn results in the hypermethylation of DNA CpG islands. Mutations in IDH-½ and TET2 are thus far mutually exclusive, which supports the notion that 2-HG produced by mIDH inhibits TET2 and impairs hematopoietic cell differentiation. In addition, 2-HG has also been shown to block PHD activity, which is critical for regulation of hypoxia inducible factors and collagen hydroxylation and maturation. Hydroxylated collagen is important for the regulation of proliferation and proper differentiation of hematopoietic cells in bone marrow. Mutated IDH is also reported to block proper hepatocyte differentiation and promote cholangiocarcinoma. Since IDH-1 mutations are only found in tumor tissue, the present invention is based in part on the discovery of that the selective mIDH-1 inhibitor of Compound 1 can be developed as a targeted therapy for cancer. The patient selection biomarker for the use of Compound 1 can be the existence of IDH-1 mutation in a patient diagnosed with a cancer harboring mIDH-1.

Using in vitro cellular mechanistic assays monitoring levels of the errantly overproduced, tumorigenic metabolic byproduct 2-hydroxy glutarate (2-HG), inhibition of mIDH-1 results in a >90% reduction in levels of measured 2-HG, an effect that has also been shown to translate into similar levels of 2-HG suppression in in vivo PK-PD studies in HCT116 (IDH-1 R132H) and HCT116 (IDH-1 R132C) xenograft bearing mice. In both models, the free concentration of Compound 1 was comparable in plasma and xenograft tumors, and exposures were dose dependent. At the highest dose tested in these studies (50 mg/kg), Compound 1 inhibited 2-HG levels in tumor by >90% for up to 24 hours after the last dose in the HCT116 (IDH-1 R132H) xenograft model, and to similar levels for at least 12 hours in the HCT116 (IDH-1 R132C) model.

Accordingly, Compound 1 is useful in methods of treating patients diagnosed with a cancer harboring an IDH-1 mutation. The neomorphic enzymatic activity acquired as a result of IDH-1 mutation is believed to lead to the conversion of α-ketoglutarate (alpha-KG) to 2-hydroxyglutarate (2-HG). In consequence, patients bearing IDH-1 mutations have elevated levels of 2-HG. Most IDH-1 mutations result in a single amino acid change at the R132 residue, whereas most IDH-2 mutations occur at either Arginine 140 (R140) or Arginine 172 (R172). The IDH mutation spectrum varies among different tumor types (Table 1).

TABLE 1

| Tumor Types | Total Mutation Frequency | IDH Mutation Identities |
|---|---|---|
| Glioma | 70-90% | $IDH1^{R132H}$, $IDH1^{R132C}$, $IDH1^{R132S}$, $IDH2^{R172K}$ |
| AML | 10-30% | $IDH2^{R140Q}$, $IDH1^{R132H}$, $IDH1^{R132C}$, $IDH2^{R172K}$, $IDH1^{R132G}$, $IDH1^{R132S}$ |
| Chondrosarcoma | 75% | $IDH1^{R132C}$, $IDH1^{R132H}$ |
| Intrahepatic Cholangiocarcinoma | 10-25% | $IDH1^{R132C}$, $IDH1^{R132L}$, $IDH1^{R132G}$, $IDH1^{R132H}$, $IDH2^{R172W}$ |

For example, IDH-1 R132 mutations represent more than 90% of the IDH mutations present in low grade glioma and secondary GBM patients. IDH-1 mutations have been reported in hematological malignancies such as acute myeloid leukemia (AML) and myelodysplastic syndrome (MDS), as well as many solid tumors types, including low grade glioma, secondary glioblastoma, intrahepatic cholangiocarcinoma (IHCC), chondrosarcoma, and melanoma. By far the most frequent IDH-1 mutations occur at amino acid position R132, and include R132H, R132C, R132S, R132G, and R132L mutations. Given that Compound 1 is a potent inhibitor of a spectrum of different IDH-1 R132 mutations, but is inactive against either wild type IDH-1 or mutated IDH-2, patients will be selected based on the occurrence of an IDH-1 mutation at the R132 residue.

The patient can be diagnosed as having an IDH-1 R132 mutation disclosed herein using sequencing methods, such as next-generation sequencing methods. The diagnostic patient selection method can be a next-generation sequencing (NGS)-based tumor genotyping assay analyzing a patient tissue sample such as a bone marrow sample. Useful techniques and technologies for diagnosing a patient as having a IDH-1 R132 mutation may include, without limitation, sequencing machines and/or strategies well known in the art, such as those developed by Illumina/Solexa (the Genome Analyzer; Bennett et al. (2005) Pharmacogenomics, 6:373-20 382), by Applied Biosystems, Inc. (the SOLiD Sequencer; solid.appliedbiosystems.com), by Roche (e.g., the 454 GS FLX sequencer; Margulies et al. (2005) Nature, 437:376-380), and by others.

In some methods, a therapeutically effective amount of Compound 1 can be administered to a patient having a mIDH1 mutation at R-132 and a concurrent mutation at FLT3. The FMS-like tyrosine kinase 3 (FLT3) gene encodes a membrane bound receptor tyrosine kinase that affects hematopoiesis leading to hematological disorders and malignancies. FLT3 is one of the frequently mutated genes in hematological malignancies, such as adult acute myeloid leukemias (AML). The presence of a FLT3 internal tandem duplication has been detected in patients with acute myeloid leukemia (AML) and patients diagnosed with intermediate and high risk myelodysplastic syndrome (MDS). The heightened frequency of constitutively activated mutant FLT3 in adult AML has made the FLT3 gene a highly attractive drug target in this tumor type. A method for treating a FLT3 mutated mIDH1 proliferative disorder can comprise identifying a mIDH1 R132 mutation in a patient and measuring expression of a mutated FLT3 or a constitutively active FLT3 mutant, and one or more genetic abnormalities in a sample obtained from a tumor sample obtained from the patient; and administering to the patient a therapeutically effective amount of Compound 1 or a pharmaceutically acceptable salt thereof (e.g., 150 mg Compound 1 BID) for 6 months or more. Useful techniques and technologies for diagnosing a patient as having a IDH-1 R132 mutation may include, without limitation, sequencing machines and/or strategies well known in the art, such as those developed by Novartis (e.g. LeukoStrat® CDx FLT3 (https://www.accessdata.fda.gov/cdrh_docs/pdf16/p160040c.pdf)).

A method of treating a patient with acute myeloid leukemia (AML), can comprise: (a) analyzing a genetic sample isolated from the patient for the presence of cytogenetic abnormalities and a mutation in at least one of FLT3, NPM1, CEBPA, IDH1, and TP53 genes; and (b) treating the patient by administering a therapeutically effective amount of Compound 1 to the patient (e.g., a total of 150 mg of Compound 1 BID each day) if the mutation is present in R132 mIDH1 and at least one of FLT3, NPM1, CEBPA and TP53 genes.

Compound 1 can be administered as a single agent as the R132X mIDH-1 Selective Inhibitor Therapy, or in combination with other therapeutic agents that are not mIDH-1 inhibitors as a combination for the R132X mIDH-1 Selective Inhibitor Therapy. As used herein, the term "R132X mIDH-1 mutation(s)" refers to a mutation at the IDH-1 arginine 132 that results in inhibitory activity of Compound 1 against the mutated IDH-1 form harboring the R132 mutation.

In some methods, Compound 1 is administered to a patient diagnosed as having a R132 IDH1 mutation either as a single agent or in combination with azacitidine. In some examples, patients have been treated with or are already being treated with azacitidine. In some embodiments, a combination therapy of Compound 1 and azacitidine can be administered for the treatment of patients with a cancer harboring aIDH-1 mutation (e.g., mIDH1 forms of AML). For example, patients can be administered Compound 1 daily (BID) in continuous 28-day cycles, in combination with azacitidine (administered at the dose of 75 mg/m$^2$ for 7 days IV/SC per every 28-day cycle).

Figure 4:
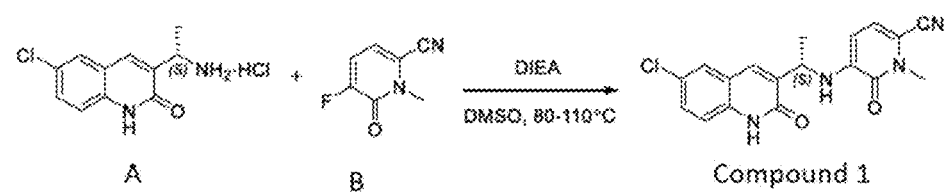
FIG. 4 is a synthetic reaction scheme for the preparation of Compound 1.
Figure 4:
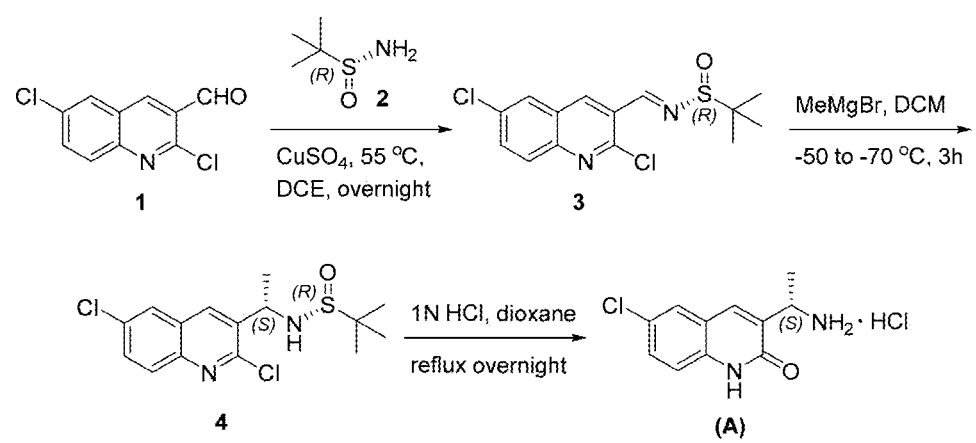
Figure 4:
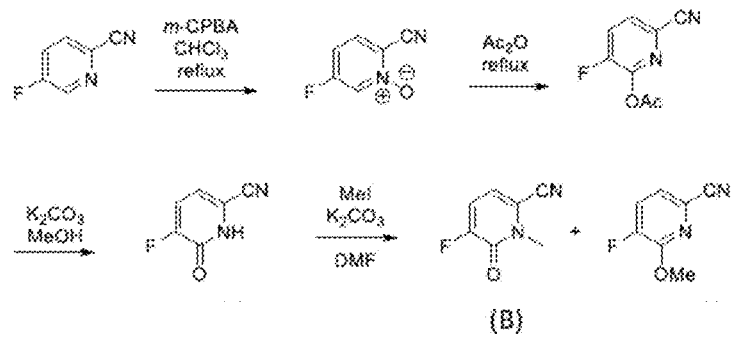
Figure 5A:
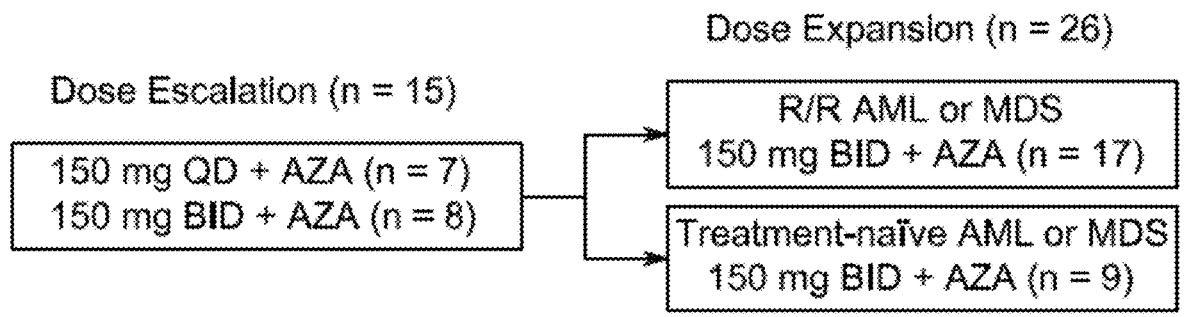
FIG. 5A illustrates the summary of cohorts from a phase 1 study in mIDH1 AML.
Figure 5B:
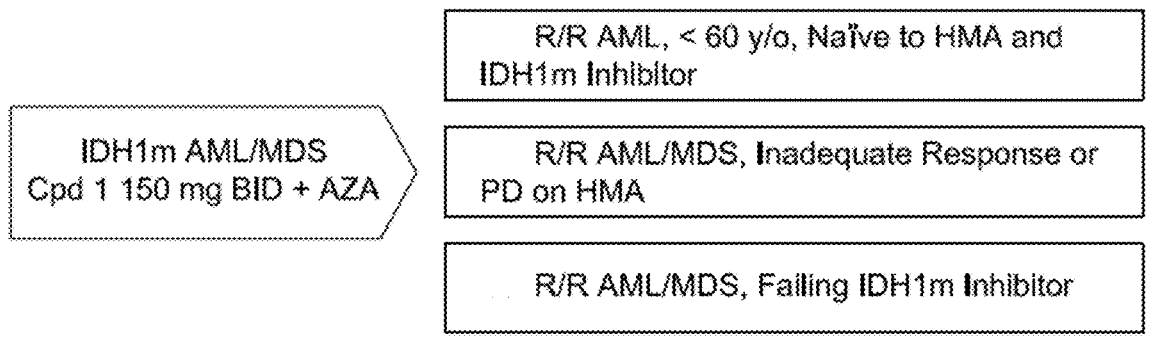
FIG. 5B illustrates use of Compound 1 in a phase 2 study in mIDH1 AML and MDS.

Referring to FIG. 4, Compound 1 can be prepared in a convergent synthesis from Intermediate A and Intermediate B as shown in FIG. 4 via the nucleophilic displacement reaction under basic conditions of (S)-3-(1-aminoethyl)-6-chloroquinolin-2(1H)-one (Intermediate A) and the fluoropyridone (Intermediate B). 1H, 13C NMR and mass spectral data are consistent with the assigned structure. The asymmetric synthesis of Intermediate A started with the condensation of the commercially available quinoline aldehyde (1) with (R)-tert-butanesulfinamide (2) to form the chiral (R)—N-tert-butanesulfinimine (3), followed by addition of methyl magnesium bromide in dichloromethane to yield the desired product (4) as the major diastereoisomer (dr: 98:2). Cleavage of the chiral auxiliary and simultaneous hydrolysis of 2-chloroquinoline moiety under mildly acidic conditions using 1N HCl in dioxane gave Intermediate A in quantitative yield. The structure of Intermediate A was confirmed by NMR and mass spectroscopy, and the enantiomeric purity was determined by chiral SFC analysis. The (S)-stereochemistry was confirmed by X-ray co-crystal structures of several inhibitor analogs prepared from the same chiral amine intermediate bound to mIDH-1 R132H. Intermediate (B) was prepared from commercially available 5-fluoropicolinonitrile in four steps. N-oxidation of 5-fluoropicolinonitrile followed by reflux of the N-oxide in acetic anhydride gave acetate, following work-up and purification. Solvolysis of the acetate group followed by N-methylation under standard conditions gave a mixture of N-methylated and O-methylated products (4:1). The minor O-methylated product was removed by column chromatography. NMR and mass spectral data are consistent with the structure of Intermediate Compound (B). Compound 1 (5-{[(1S)-1-(6-chloro-2-oxo-1,2-dihydroquinolin-3-yl)ethyl]amino}-1-methyl-6-oxo-1,6-dihydropyridine-2-carbonitrile) has a molecular weight of 355 with a melting point onset temperature of 251.3 C (DSC) and peak maximum 254.1° C.

The present disclosure also contemplates, among other things, the following numbered embodiments:

1. A method of treating a patient diagnosed with a cancer harboring a cancer cell with an IDH-1 R132 mutation selected from the group consisting of: R132L, R132G, and R132S, the method comprising administering to the patient in need thereof a therapeutically effective amount of Compound 1.
2. The method of embodiment 1, wherein the cancer does not harbor a IDH-2 mutation.
3. The method of embodiment 1, wherein the cancer does not harbor a IDH-2 mutation selected from the group consisting of: IDH-2 R172K and IDH-2 R140Q.
4. The method of embodiment 1, wherein the patient is diagnosed as having a R132 mutation based on a patient diagnostic.
5. The method of embodiment 4, wherein the patient diagnostic comprises detecting the R132 mutation in a tissue sample obtained from the patient.
6. The method of embodiment 5, wherein the tissue sample is obtained from the bone marrow of the patient.
7. The method of any one of embodiments 4-6, wherein the R132 mutation is detected using next generation sequencing (NGS) without the use of PCR.
8. A method of treatment comprising the steps of:
    a. selecting a patient for treatment based on the presence of one or more IDH-1 mutations selected from the group consisting of: R132L, R132G, and R132S;
    b. administering Compound 1 to the selected patient from step (a) at a starting dose of 150 mg taken orally twice daily until disease progression or unacceptable toxicity.
9. The method of embodiment 8, where the IDH-1 mutation is detected in cancer cells obtained from the blood or bone marrow of the patient.
10. The method of embodiment 9, wherein the IDH-1 mutation is detected prior to administering Compound 1 to the patient.
11. The method of any one of embodiments 1-10, comprising the step of detecting the IDH-1 mutation in a cell from the patient using a next-generation sequencing (NGS)-based tumor genotyping assay.
12. The method of any one of embodiments 1-11, wherein administration of Compound 1 to the patient results in a decreased 2-hydroxyglutarate (2-HG) levels in the blood of the patient within the first 15 consecutive days of treatment of the patient with Compound 1.
13. The method of any one of embodiments 1-12, wherein the method comprises administering 150 mg of Compound 1 to the patient in the solid form obtained from the method of Example 5.
14. The method of any one of embodiments 1-12, wherein the method comprises administering 150 mg of Compound 1 to the patient twice daily throughout a course of treatment.
15. The method of embodiment 14, wherein the course of treatment is at least 15 consecutive days.
16. The method of any one of embodiments 1-15, wherein Compound 1 is administered to the patient once every 12 hours on consecutive days throughout a course of treatment.
17. The method of any one of embodiments 1-16, wherein Compound 1 is administered to the patient throughout a course of treatment of at least 6 months.
18. A method of inhibiting the production of 2-HG from a cell harboring a IHD-1 mutation selected from the group consisting of: R132L, R132G and R132S, the method comprising contacting the cell with Compound 1 in an amount, under conditions, and for a time sufficient to inhibit the production of 2-HG from the cell.
19. A method of treating a patient diagnosed with a cancer harboring a cancer cell with an IDH-1 R132 mutation, the method comprising administering to the patient in need thereof a therapeutically effective amount of Compound 1.
20. The method of embodiment 19, wherein the patient is diagnosed with a cancer harboring an IDH-1 R132 mutation in a cell obtained from the patient, prior to the administration of Compound 1.
21. A method of treating a patient diagnosed with a cancer harboring a cancer cell with an IDH-1 R132 mutation, the method comprising administering to the patient in need thereof a therapeutically effective amount of Compound 1.
22. The method of embodiment 21, wherein the patient is diagnosed with a cancer harboring an IDH-1 R132 mutation in a cell obtained from the patient, prior to the administration of Compound 1.
23. A method of treating a patient diagnosed with a cancer, the method comprising
    a. diagnosing the patient as having a mutant IDH-1 mutation in a cell obtained from the patient; and
    b. administering a therapeutically effective amount of a pharmaceutical composition comprising Compound 1 to the patient in need of an inhibitor of the mutant IDH-1 enzyme that targets the mutant IDH-1 variants R132C at no greater than about 5 times the level of R132H; and
    c. continuing to administer the pharmaceutical composition to the patient throughout a course of treatment of at least 6 months.
24. The method of embodiment 23, wherein the patient is in need of an inhibitor of mIDH-1 variants selected from the group consisting of R132L, R132G, and R132S;
25. The method of any one of embodiments 23-24, wherein the relative targeting of R132C and R132H variants of mIDH-1 is measured by the ratio of $IC_{50}$ values obtained using the assay of Example 3.
26. The method of any one of embodiments 23-25, wherein the patient is diagnosed as having an IDH-1 mutation in a cell from the patient using a next-generation sequencing (NGS)-based tumor genotyping assay.
27. The method of any one of embodiments 23-26, wherein the pharmaceutical composition is administered to the patient twice per day.
28. The method of any one of embodiments 23-27, wherein the pharmaceutical composition is administered to the patient in a dose of 150 mg BID on consecutive days throughout the course of treatment.
29. The method of any one of embodiments 23-28, wherein Compound 1 in the pharmaceutical composition has the solid form obtained from Example 5.
30. A method of inhibiting the production of inhibiting the production of 2-HG in a R132C mutated IDH-1 enzyme at no more than about 5 times the inhibition of 2-HG production in a R132H mutated IDH-1 enzyme, the method comprising contacting an IDH-1 enzyme not having arginine at position 132 with a composition comprising Compound 1 under conditions and for a time effective to inhibit 2-HG production in either an IDH-1 R132C or an IDH-1 R132H mutation in the mIDH-1 enzyme.

31. A method of treating a cancer in an adult patient, the cancer having a known mIDH-1 frequency of about 10-90%, the method comprising administering to a patient diagnosed with an IDH-1 mutation comprising an IDH-1 mutation selected from the group consisting of R132C, R132H, R132L, R132G, and R132S, the method comprising administering to the patient in need thereof a pharmaceutical composition comprising a total of 150 mg of a pharmaceutically acceptable solid form of 5-{[(1S)-1-(6-chloro-2-oxo-1,2-dihydroquinolin-3-yl)ethyl]amino}-1-methyl-6-oxo-1,6-dihydropyridine-2-carbonitrile, twice per day on consecutive days for a course of treatment comprising 6 months.

32. The method of embodiment 31, wherein the patient is diagnosed as having an IDH-1 mutation in a cell from the patient using a next-generation sequencing (NGS)-based tumor genotyping assay.

33. The method of any one of embodiments 31-32, wherein the pharmaceutical composition is administered to the patient every 12 hours.

34. The method of any one of embodiments 31-33, wherein Compound 1 in the pharmaceutical composition has the solid form obtained from Example 5.

35. A method of treating a chondrosarcoma cancer having an IDH-1 mutation in an adult patient, the method comprising administering to the patient in need thereof a pharmaceutical composition comprising a total of 150 mg of a pharmaceutically acceptable solid form of 5-{[(1S)-1-(6-chloro-2-oxo-1,2-dihydroquinolin-3-yl)ethyl]amino}-1-methyl-6-oxo-1,6-dihydropyridine-2-carbonitrile, twice per day on consecutive days for a course of treatment comprising 6 months.

36. The method of embodiment 35, wherein the patient is diagnosed as having an IDH-1 mutation in a cell from the patient using a next-generation sequencing (NGS)-based tumor genotyping assay.

37. The method of any one of embodiments 35-36, wherein the pharmaceutical composition is administered to the patient every 12 hours.

EXAMPLES

Figure 2A:
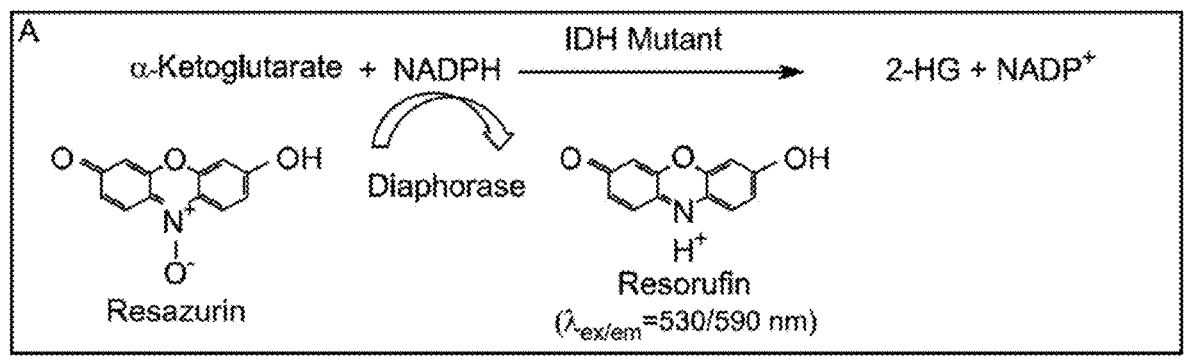
FIG. 2A and FIG. 2B are each a schematic of diaphorase-coupled assays used in Example 1, which measure activity by the determination of the level of remaining co-substrate NADPH after the enzymatic reaction is quenched.
Figure 2B:
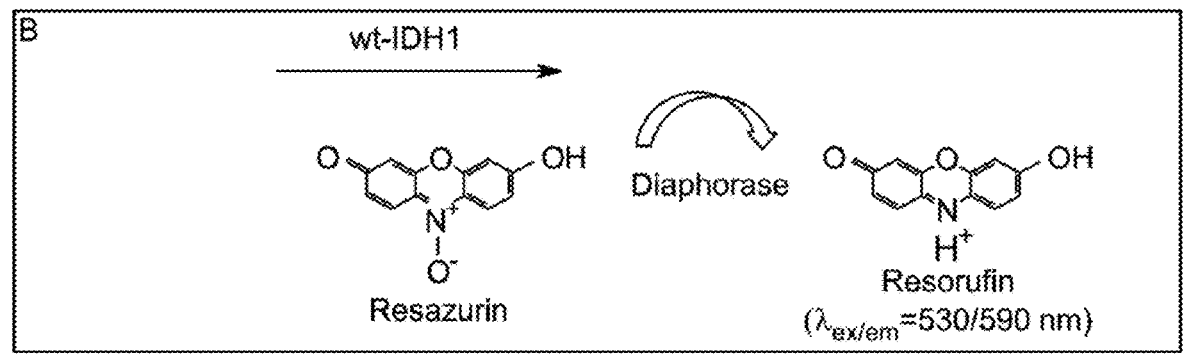

Example 1: Compound 1 Potently and Selectively Inhibited 2-HG Production in IDH-1 R132H and IDH-1 R132C Mutant Enzymes in Biochemical Assays, Compared to Wild Type IDH-1 Enzyme and Mutant IDH-2 Enzymes The biochemical potencies of Compound 1 against IDH-1 R132H and IDH-1 R132C mutants were determined in diaphorase-coupled assays, which measure activity by the determination of the level of remaining co-substrate NADPH after the enzymatic reaction is quenched (FIG. 1). FIG. 2A and FIG. 2B are schematics illustrating the working principle of the diaphorase-coupled assay for measuring potency and selectivity of Compound 1 for IDH-1 and IDH-2 enzymes. Recombinant homodimeric IDH-1 R132H or IDH-1 R132C mutant enzymes were used in these assays. Results are shown in Table 2, relative to the $IC_{50}$ value obtained for R132H IDH-1 mutated enzyme. Referring to data in Table 2, Compound 1 was found to selectively inhibit the enzymatic activity of the IDH-1 R132H and IDH-1 R132C mutations with an $IC_{50}$ value within a factor of about 5 (i.e., the $IC_{50}$ value measured for IDH-1 R132C mutant enzyme was about 5 times higher than the $IC_{50}$ measured in the IDH-1 R132H mutated enzyme). The selectivity of Compound 1 against other IDH isozymes was also tested utilizing diaphorase coupled assays employing either wild-type IDH-1 or one of 2 alternate mutated forms of IDH-2, namely IDH-2 R172K and IDH-2 R140.

TABLE 2

| Target | Relative Enzymatic $IC_{50}$ (Average +/− SEM, nM) |
|---|---|
| IDH-1 R132H | 1.0(±6.6%) |
| IDH-1 R132C | 5.1 (±6.1%) |
| Wild Type IDH-1 | 922 |
| IDH-2 R172K | >1,000 |
| IDH-2 R140Q | >4,000 (no activity measured) |

Compound 1 had comparatively very weak activity against wild type IDH-1 ($IC_{50}$ value of about 922 times greater than the $IC_{50}$ value measured for IDH-1 R132H). Compound 1 also demonstrated very weak activity against IDH-2 R172K that was more than 1,000 greater than the $IC_{50}$ value measured for IDH-1 R132H. Compound 1 did not show any inhibition of IDH-2 R140Q up to a concentration of 100 μM. These selectivity data indicate that Compound 1 is a potent and selective inhibitor of IDH-1 R132 mutations.

Figure 3A:
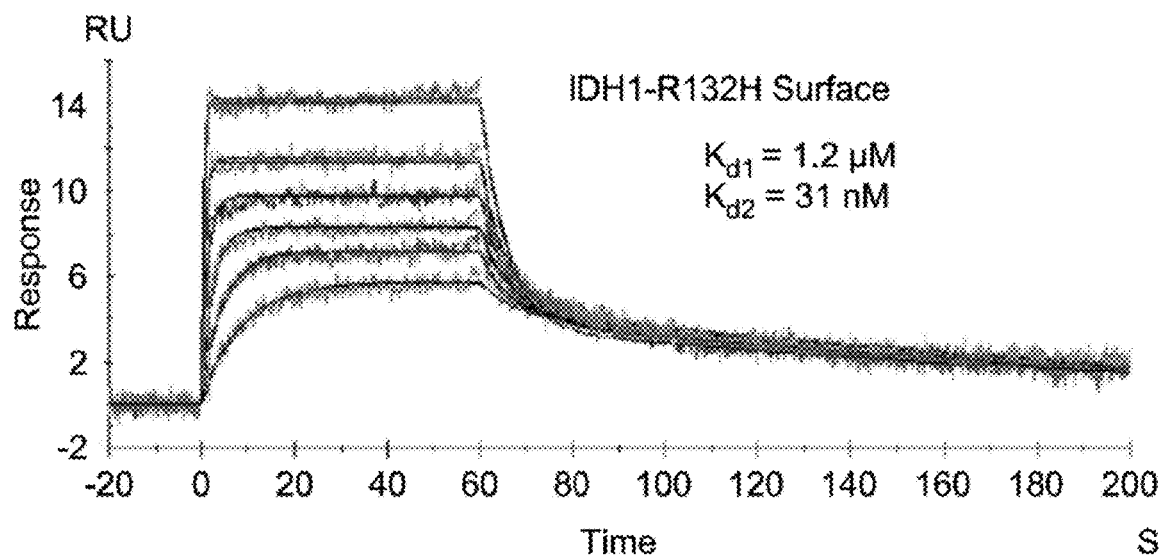
FIG. 3A is a graph showing the results from a surface plasmon resonance (SPR) biophysical characterization of the molecular interaction between mIDH-1 inhibitor Compound 1 and recombinant IDH-1-R132H protein.
Figure 3B:
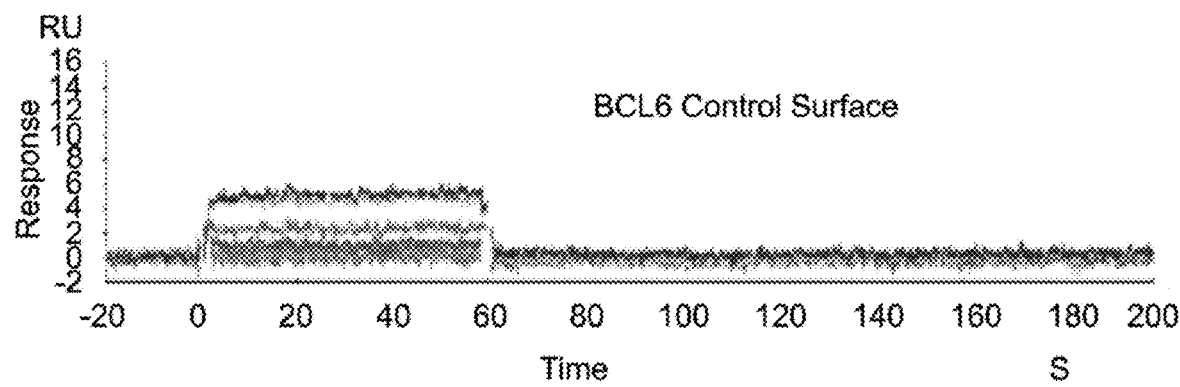
FIG. 3B is a comparator graph showing the SPR characterization of Compound 1 at a BCL6 control surface.

Example 2: Compound 1 Exhibited Specific Binding to a Surface Containing Immobilized IDH-1 R132 Mutant Protein (Compared to a Comparator Surface with Immobilized BCL6), with Two Binding Sites Having Different Kd Values Detected by Surface Plasmon Resonance Analysis The biophysical interaction between Compound 1 and IDH-1 R132H was further characterized using Surface Plasmon Resonance (SPR) technology. Compound 1 was shown to exhibit specific binding to the surface containing immobilized IDH-1 R132H mutant protein compared to a control surface on which the unrelated protein BCL6 was immobilized, where no binding was observed (FIG. 3A and FIG. 3B, respectively). Analysis of the SPR data revealed two binding sites between Compound 1 and IDH-1 R132H, with Kd values of 31 nM (with kon1=2.04±0.03×105 M-1s-1 and koff1=0.0063±0.0001 s-1) and 1200 nM (with kon2=1.56±0.03×105 M-1s-1 and koff1=0.187±0.001 s-1), respectively. It is likely that the apparent low affinity binding site is an artifact of the immobilization of the protein on the surface of the chip, and as the Kd value for the high affinity binding site is close to the enzymatic $IC_{50}$ of Compound 1 for IDH-1 R132H, this was used to confirm specific binding of Compound 1 to IDH-1 R132H.

Example 3: Compound 1 Potently Inhibited 2-HG Production in IDH-1 R132G, IDH-1 R132L, and IDH-1 R132S Mutant Cell Lines in Cell Based Assays, with $IC_{50}$ Values Greater than IDH-1 R132C Mutant Cell Lines The cellular potency of Compound 1 in suppressing intracellular 2-HG levels was determined in cell lines expressing five different mutated IDH-1 proteins found in human cancers (R132H, R132C, R132G, R132L, R132S). The human fibrosarcoma cell line HT-1080 harbors a naturally occurring heterozygous IDH-1 R132C mutation. The human colorectal carcinoma cell line HCT 116 is wild type for IDH-1, but heterozygous mutations coding for IDH-1 R132H or R132C were introduced by knock-in into the endogenous IDH-1 gene locus. Finally, the human astrocytoma cell line U-87 MG is also wild type for IDH-1, but expression of five different mutated IDH-1 proteins was achieved by stable transfection.

The parental HCT116 line (colon) line does not produce high levels of 2-HG, but the variants used herein (X-MAN HCT-116 lines obtained from Horizon Discovery Ltd.) are engineered to knock-in a heterozygous mutation of either IDH-1 R132H or IDH-1 R132C. This recapitulates the cellular context in mIDH-1 cancer cells where there are both wild type and mutant IDH-1 subunits that together form a heterodimer that is responsible for the production of elevated levels of 2-HG. These modified lines can be used as models of IDH-1 mutant disease.

Each of these cell lines was treated with Compound 1 for 24 hr, and intracellular 2-HG levels were determined by mass spectroscopy. As shown in the Table 3, Compound 1 suppressed 2-HG production in each cell line, with $IC_{50}$ values ranging from less than 10 nM to less than 150 nM. Compound 1 is therefore a potent inhibitor of a variety of clinically relevant IDH-1 mutations in a cellular context. Table 3 shows the $IC_{50}$ values measured relative to the $IC_{50}$ value obtained for U-87 MG/IDH-1 R132G.

TABLE 3

| Cell Line | Relative 2-HG $IC_{50}$ (nM)* |
| --- | --- |
| U-87 MG/IDH-1 R132G | 1.0 (±30%) |
| U-87 MG/IDH-1 R132S | 1.17 (±21%) |
| U-87 MG/IDH-1 R132H | 1.29 (±17%) |
| U-87 MG/IDH-1 R132L | 5.39 (±22%) |
| U-87 MG/IDH-1 R132C | 7.00 (±30%) |
| HCT116(IDH-1 R132H/+) | 3.36 (±19%) |
| HT-1080(IDH-1 R132C/+) | 9.66 (18%) |
| HCT116(IDH-1 R132C/+) | 13.96 (±18%) |

*Mean +/− SEM where applicable

Example 4: Testing Compound 1 in Mouse Xenograft Models Using HCT 116 Cells with R132 C and R132H Mutations In order to optimize the dosing schedule of Compound 1 to achieve sustained >90% 2-HG inhibition in mIDH-1 in vivo, HCT116 (IDH-1 R132H) and HCT116 (IDH-1 R132C) xenograft-bearing mice were treated with Compound 1 at 25 and 50 mg/kg BID (3 doses). The free drug concentration of Compound 1 at 12 hour post final dose is above the in vivo $IC_{90}$ for all doses, and a greater than 90% reduction of 2-HG levels in tumor were achieved in each case. The free drug concentration decreased to 3-10× the in vivo $IC_{50}$ at 24 hour post final dose, and Compound 1 showed 80-90% inhibition. There was less than 20 nM free drug concentration in tumor at 48 and 72 hours after final dose, and at that point there was less than 50% 2-HG inhibition in tumor samples, consistent with the reduced level of Compound 1.

Example 5: Pharmaceutical Compositions in an Oral Dosage Form of Compound 1

A therapeutically effective amount of Compound 1 can be orally administered (e.g., an amount providing a steady state blood concentration greater than the $IC_{90}$ for 2-HG production for cancer cells having the IDH-1 R132 mutation disclosed herein, and less than an amount of about 7,200 ng/mL). For example, a therapeutically effective amount of Compound 1 can provide a steady state blood concentration of about 2,000 ng/mL to 7,200 ng/mL throughout the course of treatment. The therapeutically effective amount can be up to about 150 mg of Compound 1 in the solid form obtained by the method of Example 5, administered to the patient BID on consecutive days throughout a course of treatment of at least about 6 months.

Step 1: Compound 1 can be obtained using the chemical synthesis disclosed in PCT patent application publication WO2016/044789A1 (published Mar. 24, 2016; filed Sep. 18, 2015). Examples 1, 21 and 25 from WO2016/044789A1 are incorporated herein by reference, along with associated analytical methods disclosed in the publication WO2016/044789A1. Briefly, Compound 1 can be obtained using the method of Example 25 (pages 92-93), based on the reaction of Intermediate II-1 (obtainable using the method of Example 1 on pages 26-27) and Intermediate III-1 (obtainable using the method of Example 21 on pages 79-82). Using this method, Compound 1 was obtained as a white solid (790 mg). m.p. 262-264° C. 1H NMR (300 MHz, DMSO-$d_6$) δ: 12.07 (s, 1H), 7.75 (s, 1H), 7.73 (d, J=2.2 Hz, 1H), 7.51 (dd, J=8.6, 2.3 Hz, 1H), 7.31 (d, J=8.8 Hz, 1H), 6.97 (d, J=8.0 Hz, 1H), 6.93 (d, J=7.7 Hz, 1H), 5.95 (d, J=8.0 Hz, 1H), 4.68 (m, 1H), 3.58 (s, 3H), 1.50 (d, J=6.6 Hz, 3H). LCMS (Method 3): 100% pure @ 254 nm, Rt 10.78 min, m z 355, 357 [M+H]+. The filtrate and the colored fractions (TLC pure) from the second ISCO were combined and treated with activated charcoal and filtered (until the filtrate is colorless). The filtrate was then concentrated under reduced pressure on rotavap to remove dichloromethane until a lot of white solid precipitated out. The white solid was collected by filtration and washed with cold MeOH. It was then mixed with MeCN/$H_2O$ (10 mL/25 mL) and lyophilized to afford the title compound 1-13 as a white solid (970 mg). m.p. 262-264° C. 1H NMR (300 MHz, DMSO-d6) δ: 12.06 (s, 1H), 7.75 (s, 1H), 7.73 (d, J=2.5 Hz, 1H), 7.51 (dd, J=8.6, 2.3 Hz, 1H), 7.31 (d, J=8.8 Hz, 1H), 6.97 (d, J=8.0 Hz, 1H), 6.92 (d, J=8.0 Hz, 1H), 5.95 (d, J=8.0 Hz, 1H), 4.68 (m, 1H), 3.58 (s, 3H), 1.50 (d, J=6.9 Hz, 3H). LCMS (Method 3): 100% pure @ 254 nm, m/z 355, 357 [M+H]$^+$. The total yield for combined two batches is >67%.

Step 2: Next, a solid form of Compound 1 can be obtained that is useful in an oral dosage form. Unless otherwise indicated, the studies in Examples 1-4, 6 and 7 were performed using a pharmaceutically acceptable solid form in an oral dosage form of Compound 1 that can be obtained by the method of Step 2 of Example 5. All volumes are with respect to the quantity of Compound 1 (v/w). Compound 1 obtained from Step 1 above is dissolved in 18 volumes of dichloromethane. The resulting solution is then concentrated under reduced pressure to approximately 5 volumes. To the mixture is added 5 volumes of ethyl acetate. The mixture is concentrated under reduced pressure to 5 volumes. To the mixture is added an additional 5 volumes of ethyl acetate, and the mixture again concentrated under reduced pressure to 5 volumes. The mixture is diluted to 10 volumes with ethyl acetate, and the mixture stirred at room temperature for 18 hours and then cooled to 0° C. The mixture is stirred at 0° C. for 3 hours and then filtered. The solids are rinsed with ethyl acetate and dried under vacuum (counterbalanced by nitrogen) at ambient temperature.

Step 3: The oral dosage form of Compound 1 is a pharmaceutically acceptable solid form of Compound 1, can be obtained using the method of Example 5 Step 2. The oral dosage form does not contain associated solvent or a counter ion. In particular, the oral dosage form of Compound 1 can be a capsule comprising drug substance (Compound 1) blended with excipients to improve powder flow and encapsulated in a Coni-Snap® hard gelatin capsule suitable for oral dosage in humans.

A pharmaceutically acceptable solid form of Compound 1 can be identified using reflection X-ray powder diffraction (XRPD) pattern of Compound 1. High resolution X-ray Powder Diffraction experiments can be performed with Panalytical X' Pert3 Powder XRPD on a Si zero-background holder. The 2 theta position can be calibrated against Panalytical 640 Si powder standard. Details of the XRPD method are listed below in Table 4, with XRPD peaks reported as diffraction angles at 2 theta, with d-spacing measured in angstroms.

TABLE 4

| Parameters for Reflection Mode | |
|---|---|
| X-Ray Wavelength | Cu, kα, Kα1, (Å): 1.540598, Kα2 (Å): 1.544426 Kα2/Kα1 intensity ration: 0.50 |
| X-Ray tube setting | 45 kV, 40 mA |
| Divergence slit | Automatic |
| Scan mode | Continuous |
| Scan range (°2TH) | 3°-40° |
| Step size (°2TH) | 0.0131 |
| Scan speed (°/s) | 0.033 |

An example of a pharmaceutically acceptable solid form of Compound 1 is a solid form characterized by a reflection X-ray powder diffraction (XRPD) pattern comprising characteristic peaks at 6.3, 12.8, 13.8, 23.6, and 27.8 degrees±0.2° 2θ. A pharmaceutically acceptable solid form of Compound 1 is a solid form characterized by characterized by an X-ray Powder Diffraction (XRPD), having diffractions at angles (2 theta±0.2) of 6.3, 12.8, 13.8, 23.6, and 27.8, corresponding to d-spacing (angstroms±0.2) of 14.0, 6.9, 6.4, 3.8, and 3.2, respectively. In some embodiments, a pharmaceutically acceptable solid form of Compound 1 can be identified by X-ray Powder Diffraction (XRPD), having characteristic diffractions at angles (2 theta±0.2) of 5.7, 6.3, 8.5, 10.6, 12.8, 13.8, 17.3, 22.0, 22.8, 23.6, and 27.8. In some embodiments, a pharmaceutically acceptable solid form of Compound 1 can be identified by X-ray Powder Diffraction (XRPD), having characteristic diffractions at angles (2 theta±0.2) of 5.7, 6.3, 8.5, 10.6, 12.8, 13.8, 17.3, 22.0, 22.8, 23.6, and 27.8, corresponding to d-spacing (angstroms±0.2) of 15.4, 14.0, 8.4, 6.9, 6.4, 5.1, 4.0, 3.9, 3.8, and 3.2, respectively.

Example 6: Comparative Compounds Demonstrated Greater Disparity Between 2-HG Inhibition in R132C and R132H IDH-1 Cells, Compared to Compound 1

The comparative activity of each of a series of mIDH-1 inhibitor compounds including Compound 1 were measured using the cell based assay in Example 3. The ratio of the $IC_{50}$ values obtained from IDH-1 R132C HCT116 mutant cells ($IC_{50}$ uM g mean)/$IC_{50}$ values obtained from IDH-1 R132H HCT116 mutant cells ($IC_{50}$ uM g mean) is provided in Table 5. Compound 1 had the lowest ratio among the tested compounds, indicating near equipotent activity of Compound 1 as measured with the R132C and R132H IDH-1 mutant cell assay of Example 3 (using the HCT 116 cells described in Example 3). Compound 1 showed comparative activity inhibiting 2-HG production from mIDH-1 R132C and R132H cell lines (using the assay of Example 3) that was within 5-fold, compared to more disparate differences in activity ranging from about 8-fold to over 200 fold (240) in comparative compound A-H in Table 5.

TABLE 5

| Compound | Structure | Ratio of $IC_{50}$ measured for [$IC_{50}$ for R132C]/[$IC_{50}$ for R132H] |
|---|---|---|
| 1 | [structure] | 4.5 |
| A | [structure] | 8.0 |

TABLE 5-continued

| Compound | Structure | Ratio of IC$_{50}$ measured for [IC$_{50}$ for R132C]/ [IC$_{50}$ for R132H] |
|---|---|---|
| B | 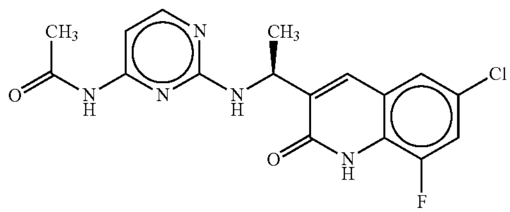 | 8.0 |
| C | 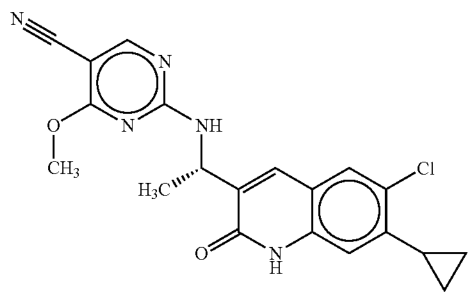 | 8.5 |
| D | 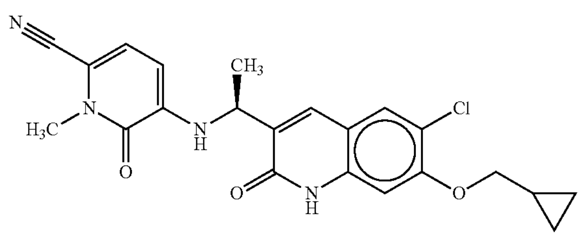 | 9.0 |
| E | 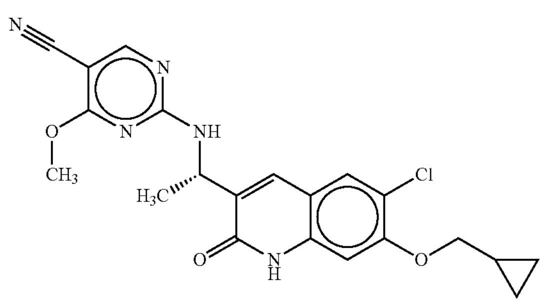 | 11.0 |
| F | 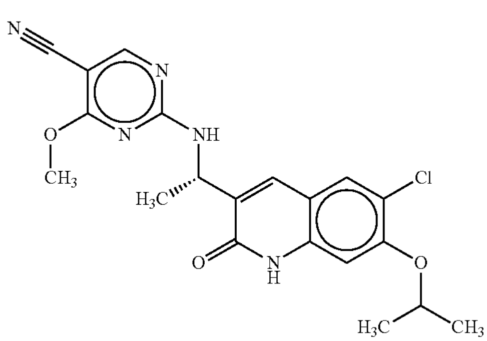 | 26 |

TABLE 5-continued

| Compound | Structure | Ratio of $IC_{50}$ measured for [$IC_{50}$ for R132C]/ [$IC_{50}$ for R132H] |
|---|---|---|
| G | (structure) | 30 |
| H | (structure) | 240 |

Example 7: Compound 1 Induces Mutation Clearance in Patients with Acute Myeloid Leukemia (AML) or Myelodysplastic Syndrome (MDS) Treated in Phase 1 Dose Escalation and Expansion Study Isocitrate dehydrogenase 1 mutations (mIDH-1) occur in 7-14% of AML patients ("pts.") and 3% of MDS pts. Compound 1 is a highly potent, selective small molecule inhibitor of mIDH-1 without anticipated CYP or QTc liabilities at the recommended phase 2 dose.

This study evaluated the safety, pharmacokinetics (PK), pharmacodynamics (PD) and clinical activity of the novel anticancer drug Compound 1, administered to patients with relapsed or refractory acute myeloid leukemia (AML) or myelodysplastic syndrome (MDS). Compound 1 is a potent, selective, orally bioavailable, small-molecule inhibitor of mutated isocitrate dehydrogenase 1 (IDH1) and is intended for the treatment of patients harboring IDH1 mutations, in both hematologic and solid tumors.

The presence of mutations at codon 132 in IDH1 imparts a neomorphic activity to the enzyme, resulting in the production of the "oncometabolite" (R)-2-hydroxyglutarate (2-HG), which has pleotropic roles in tumorigenesis. Studies in genetically engineered mouse models and models derived from cancer patient samples support the hypothesis that mutated IDH1 produces 2-HG, the downstream effects of which cause epigenetic changes that consequently block the proper differentiation of progenitor cells and lead to cancer. These data support the therapeutic rationale that inhibition of mutated IDH1 will lower (R)-2-hydroxyglutarate (2-HG) levels and restore normal cellular differentiation.

Inclusion Criteria

To be considered eligible to participate in this study, a patient met the inclusion criteria listed below:
1. Pathologically proven AML (except acute promyelocytic leukemia with the t(15;17) translocation) or intermediate risk, high risk or very high risk MDS as defined by the World Health Organization (WHO) criteria or Revised International Prognostic Scoring System (IPSS-R) harboring IDH1-R132 mutations, and one of the following based on enrollment stage or treatment cohort:
  a. Single Agent Phase 1 Cohorts including Dose-Escalation/Dose-Expansion: AML/MDS either R/R to standard therapy, or for whom standard treatments are contraindicated
  b. Combination (Compound 1+azacitidine) Phase 1 Dose-Escalation/Dose-Expansion (patients must meet one of the following):
    i. Patients with AML that is either R/R to standard therapy, or for whom standard treatments are contraindicated
    ii. Patients with MDS that is either R/R to standard therapy, or are treatment naïve, who are eligible for azacitidine therapy
  c. Combination (Compound 1+cytarabine) Phase 1 Dose-Escalation/Dose-Expansion Cohort: Patients ≥60 years with treatment-naïve AML for whom standard treatments are contraindicated
  d. Phase 2 Cohort 1 (Single Agent) only: AML R/R to standard therapy
  e. Phase 2 Cohort 2 (Single Agent) only: AML in morphologic CR/CRi after prior therapy (+/−HSCT) with residual IDH1-R132 mutation 0.01%) detected in the bone marrow
  f. Phase 2 Cohort 3 (Single Agent) only: R/R AML/ MDS that have been previously treated with IDH1 inhibitor therapy AND for whom standard treatments are contraindicated
  g. Phase 2 Cohort 4 (Compound 1+Azacitidine) only: Patients <60 years old with R/R AML/MDS with no prior hypomethylating agent therapy AND no prior IDH1 inhibitor therapy
  h. Phase 2 Cohort 5 (Compound 1+Azacitidine) only: R/R AML/MDS that have inadequately responded to or have progressed on prior treatment with a hypomethylating agent i. Phase 2 Cohort 6 (Compound 1+Azacitidine) only: R/R AML/MDS that have been previously treated with a single agent IDH1 inhibitor as their last therapy prior to study enrollment
j. Phase 2 Cohort 7 (Single Agent) only: Treatment naïve AML patients for whom standard treatments are contraindicated
k. Phase 2 Cohort 8 (Compound 1+Azacitidine) only: Treatment naïve AML patients who are candidates for azacitidine as a first line treatment
   (Note for Phase 2 Cohort 7 and Phase 2 Cohort 8: Treatment naïve is defined as no prior treatment for AML. Patients may have received a prior treatment for another hematologic malignancy.)
2. Patients must have documented IDH1-R132 gene-mutated disease as evaluated by the site
3. Patients ≥18 years old
4. Eastern Cooperative Oncology Group (ECOG) performance status of 0 to 2
5. Signed informed consent prior to beginning study and undergoing procedures
6. No prior solid organ allograft
7. Acceptable liver function:
   a. Bilirubin ≤2 times upper limit of normal (ULN) (≤3 times ULN in patients with Gilbert Syndrome)
   b. Aspartate transaminase (AST, also referred to as SGOT), alanine transaminase (ALT, also referred to as SGPT) and alkaline phosphatase (ALP) 3 times ULN
8. Acceptable renal function:
   a. Serum creatinine ≤1.5 times ULN or calculated creatinine clearance ≥50 mL/min (Cockcroft and Gault 1976)
9. Recovery from the non-hematologic toxic effects of prior treatment to Grade ≤1, or baseline value according to NCI CTCAE classification (excluding infertility, alopecia, or Grade 1 neuropathy)
10. Baseline QTcF≤450 msec (average of the QTcF values of screening triplicate ECGs) Note: This criterion does not apply to patients with a bundle branch block (BBB); for patients with BBB, a cardiology consult is recommended to ensure that QTcF is not prolonged.
11. Negative serum pregnancy test if female of childbearing potential
12. For fertile men and women, agreement to use highly effective contraceptive methods for the duration of study participation and 90 days after the last dose of study medication
13. Agreement for male patients not to donate sperm and for female patients of childbearing potential not to donate ova during the study and for 90 days after the final dose of study drug
14. Phase 2 Cohorts 1-8 (SA and combination) only: Pre-treatment peripheral blood and bone marrow aspirate available for retrospective central confirmation of IDH1-R132 mutation is required. Note: Central confirmation of IDH1-R132 mutation is not required for study enrollment.

Exclusion Criteria

To be eligible for entry into the study, the patient did not meet any of the exclusion criteria listed below:
1. Phase 1 Single Agent Dose-escalation/Dose-expansion Cohorts and Phase 2 Cohorts 1, 4, 5, 7 and 8 only: Patients who have been treated with an IDH1 targeted therapy are excluded
2. Phase 2 Single Agent Cohorts 1-3 and 7 only: Patients with IDH2 mutation detection at baseline or history of IDH2m inhibitor treatment are excluded
3. History of prior malignancy unless disease-free for 12 months or considered surgically cured; patients with nonmelanoma skin cancers or with carcinomas in situ are eligible regardless of the time from diagnosis (including concomitant diagnoses)
4. Patients with symptomatic central nervous system (CNS) metastases or other tumor location (such as spinal cord compression, other compressive mass, uncontrolled painful lesion, bone fracture, etc.) necessitating an urgent therapeutic intervention, palliative care, surgery or radiation therapy
5. Patients with previous allogeneic HSCT, if they meet any of the following criteria: <100 days from time of HSCT; active acute or chronic graft vs. host disease (GvHD); or receiving immunosuppressive therapy as treatment or prophylaxis against GvHD Note: Doses <20 mg methylprednisolone (or its equivalent) daily are not an exclusion criterion.
6. Treatment with radiation therapy, major surgery (requiring general anesthesia) within one month prior to study drug dosing
7. Treatment with chemotherapy or small molecule anticancer therapeutic within five half-lives of the agent or within 21 days if the half-life is unknown. Patients reenrolling in Cohort 6 after relapse/progression on Cohort 1 are exempt from this washout requirement (i.e. can continue Compound 1 treatment until re-enrollment) 8. Treatment with an anticancer therapeutic antibody less than four weeks before first dose of study drug
9. Treatment with other experimental therapies or participation in another clinical trial within a period of time that is less than the cycle length or within 21 days prior to starting study drug, whichever is shorter
10. Patients unable to swallow oral medications, or patients with gastrointestinal conditions (e.g., malabsorption, resection, etc.) deemed by the Investigator to jeopardize intestinal absorption
11. Congestive heart failure (New York Heart Association Class III or IV) or unstable angina pectoris; previous history of myocardial infarction within one year prior to study entry, uncontrolled hypertension, or uncontrolled arrhythmias
12. Patients with a family history of QT prolongation
13. Concomitant medication(s) known to cause Torsades de Pointes (TdP) initiated less than the duration required to reach steady-state plasma concentration (approximately five half-lives) before first dose of study drug (medications used as needed [PRN] (e.g. Zofran) are exempt)
14. Concurrent treatment with chronic corticosteroids except if chronic treatment with <20 mg of methylprednisolone daily or equivalent (pulse steroids for treatment or prophylaxis are allowed [e.g., for transfusion or medication reactions])
15. Known HIV positivity
16. Active, uncontrolled bacterial, viral, or fungal infections, requiring systemic therapy (prophylactic systemic antimicrobials permitted)
17. Uncontrolled disease-related metabolic disorder (e.g., hypercalcemia)
18. Pregnant or nursing women or women of childbearing potential not using highly effective contraception; male patients not using highly effective contraception. Note:

Women of childbearing potential and men must agree to use highly effective contraception prior to study entry and for the duration of study participation and 90 days after. Should a woman become pregnant or suspect she is pregnant while participating in this study, she should inform her treating physician immediately.
19. Serious nonmalignant disease (e.g., hydronephrosis, liver failure, or other conditions) that could compromise protocol objectives in the opinion of the Investigator and/or the Sponsor
20. Unwillingness or inability to comply with procedures either required in this protocol or considered standard of care
21. Medical, uncontrolled disease-related metabolic disorder, psychiatric, cognitive, or other conditions that may compromise the patient's ability to understand the patient information, give informed consent, comply with the study protocol, or complete the study
22. History of severe allergic reaction to azacitidine (if patient enrolling into azacitidine combination cohort) or low-dose cytarabine (if patient enrolling into cytarabine combination cohort)
23. Prisoners or patients who are involuntarily incarcerated or are compulsorily detained for treatment of either a psychiatric or physical (e.g. infectious disease) illness. Note: Under certain specific circumstances, a person who has been imprisoned may be included or permitted to continue as a patient, if local regulations permit. Strict conditions apply and FORMA's approval is required.

Primary Outcome Measures

The outcome of the study can be evaluated using the following criteria:
1. Maximum Tolerated Doses (MTDs) or Maximum Evaluated Doses (MEDs) [Phase 1]. Time Frame: Within first 4 weeks of treatment.
2. Number of Participants with a Dose Limiting Toxicity (DLT) [Phase 1]. Time Frame: Within first 4 weeks of treatment. DLT Criteria can include:
   ≥Gr 3 non-hematologic toxicity or laboratory finding
   Gr 4 hematologic toxicity by Day 42 in absence of disease
   Inability to tolerate at least 75% of Cycle 1 treatment
3. Doses recommended for future studies [Phase 1]. Time Frame: Within first 4 weeks of treatment.
4. Complete Response (CR, CRi, MLFS, Marrow CR) Rate of Compound 1 as a single-agent or in combination with Azacitidine in patients with AML/MDS [Phase 2]. Time Frame: As per IWG Response Assessment Guidelines for AML and MDS based on investigator's assessment through study completion, e.g. modified IWG AML 2003/MDS 2006.

Secondary Outcome Measures

The outcome of the study can also be evaluated using the following criteria:
1. Area under the plasma concentration versus time curve (AUC) [Phase 1 and Phase 2]. Time Frame: Blood samples for PK analysis collected at multiple visits during the first 60 days of treatment and on day 1 of all cycles following the first 30 days.
2. Peak Plasma Concentration (Cmax) [Phase 1 and Phase 2]. Time Frame: Blood samples for PK analysis collected at multiple visits during the first 60 days of treatment and on day 1 of all cycles following the first 30 days.
3. Time of peak plasma concentration (Tmax) [Phase 1 and Phase 2]. Time Frame: Blood samples for PK analysis collected at multiple visits during the first 60 days of treatment and on day 1 of all cycles following the first 30 days.
4. Time for half of the drug to be absent in blood stream following dose (T ½) [Phase 1 and Phase 2]. Time Frame: Blood samples for PK analysis collected at multiple visits during the first 60 days of treatment and on day 1 of all cycles following the first 30 days.
5. Rate at which drug is removed from blood stream (CL/F) [Phase 1 and Phase 2]. Time Frame: Blood samples for PK analysis collected at multiple visits during the first 60 days of treatment and on day 1 of all cycles following the first 30 days.
6. Rate of drug distribution within the blood stream (Vd/F) [Phase 1 and Phase 2]. Time Frame: Blood samples for PK analysis collected at multiple visits during the first 60 days of treatment and on day 1 of all cycles following the first 30 days.
7. Reduction of 2-HG levels in plasma [Phase 1 and Phase 2]. Time Frame: Blood samples for PK/PD analysis collected at multiple visits during the first 60 days of treatment and on day 1 of all cycles following the first 30 days.
8. Evidence of antileukemic or antimyelodysplastic activity of Compound 1 as determined by complete response (CR), CRi (complete remission with incomplete hematologic recovery), morphologic leukemia-free state (MLFS), Marrow CR, partial remission (PR), and stable disease (SD) as a single-agent or in combination with azacitidine or cytarabine [Phase 1]. Time Frame: As per IWG Response Assessment Guidelines for AML and MDS based on investigator's assessment through study completion.
9. Incidence and severity of adverse events, clinical laboratory abnormalities, and changes in ECG parameters as assessed by CTCAE v4.0 as a single-agent or in combination with azacitidine [Phase 2]. Time Frame: Safety will be assessed from time of first dose through 28 days post last dose.
10. Additional measures of antileukemic or antimyelodysplastic activity as determined by CRh, Overall Response (OR), and Stable Disease of Compound 1 alone or in combination with azacitidine [Phase 2]. Time Frame: As per IWG Response Assessment Guidelines for AML and MDS based on investigator's assessment through study completion.
11. Time to Response (TTR) [Phase 2]. Time Frame: From first dose of study drug through time of first response by blood recovery count.
12. Duration of Response (DOR) [Phase 2]. Time Frame: From time of first response by blood recovery count through relapse.
13. Event-Free Survival (EFS) [Phase 2]. Time Frame: From time of entry on study through progression.
14. Overall Survival (OS) [Phase 2]. Time Frame: From time of entry on study through death or date last known alive at end of follow-up.

Disease History and Baseline Characteristics of Participants

A summary the disease history and participant demographics is provided below:

TABLE 6

Demographics and Disease History

| Characteristic | Compound 1 (n = 32)* | Compound 1 + AZA (n = 46) |
|---|---|---|
| Age, median (range), years | 72 (35-87) | 67 (31-88) |
| Female, % | 50 | 52 |
| ECOG PS-0/1/2,% | 28/50/22 | 28/57/15 |
| AML, n | 26 | 39 |
| Relapsed | 14 | 11 |
| >12 mo | 4 | 1 |
| ≤12 mo | 10 | 10 |
| Refractory | 8 | 15 |
| Treatment-naïve | 4 | 13 |
| Prior regimens, median (range)** | 2 (0-9) | 3 (0-6) |
| HMA (azacitidine/decitabine) | 12 | 9 |
| IDHm inhibitor | 1 | 4 |
| Investigational | 2 | 2 |
| HSTC | 2 | 3 |
| MDS, n | 6 | 7 |
| Relapsed/Refractory | 4 | 2 |
| Treatment-naïve | 2 | 5 |
| Prior regimens, median (range) | 1 (0-4) | 0 (0-4) |
| HMA (azacitidine/decitabine) | 4 | 2 |

*Including 3 pts treated with 100 mg QD with food.
**Not inclusive of all types; pt could have received more than one type A summary of the baseline disease characteristics is shown below:

TABLE 7

Baseline Disease Characteristics

| All SA and CO | R/R AML (n = 48) | TN AML (n = 17) | MDS** (n = 13) | All AML + MDS (n = 78) |
|---|---|---|---|---|
| IDH1 mutation type*, n | | | | |
| R132C | 23 | 10 | 5 | 38 |
| R132H | 13 | 3 | 6 | 22 |
| R132S | 6 | 2 | 0 | 8 |
| R132G | 5 | 2 | 1 | 8 |
| R132L | 1 | 0 | 0 | 1 |
| Concurrent mutations*, n | | | | |
| FLT3 | 12 | 0 | 1 | 13 |
| NPM1 | 12 | 1 | 1 | 14 |
| CEBPA | 1 | 0 | 1 | 2 |
| TP53 | 3 | 0 | 1 | 4 |
| IDH2 | 1 | 1 | 0 | 2 |

*As reported by investigator per local tests
**One pt with R100 mutation

A summary of the Investigator-Assessed Response is shown below:

TABLE 8

Investigator-Assessed Response

| | Compound 1 SA | | Compound 1 + AZA | |
|---|---|---|---|---|
| Response | R/R AML (n = 22) | All Pts (n = 32) | R/R AML (n = 26) | All Pts* (n = 45) |
| ORR, n (%)** | 9 (41) | 12 (38) | 12 (46) | 26 (58) |
| [95% CI] | [21, 64] | [21, 56] | [27, 67] | [42, 72] |
| CR/CRm, n (%) | 4 (18) | 5 (16) | 3 (12) | 14 (31) |
| CRh, n (%) | 3 (14) | 3 (9) | 1 (4) | 1 (2) |
| Cri, n (%) | 2 (9) | 3 (9) | 6 (23) | 9 (20) |
| MLFS, n (%) | 0 | 0 | 2 (8) | 2 (4) |
| Marrow CR, n (%) | N/A | 1 (3) | N/A | 0 |
| SD, n (%) | 5 (23) | 9 (28) | 11 (42) | 14 (31) |
| PD, n (%) | 2 (9) | 3 (9) | 1 (4) | 1 (2) |
| NE, n (%) | 6 (27) | 8 (25) | 2 (8) | 4 (9) |

*one pt excluded from efficacy analysis due to the lack of a R132X mutation; pt continued on treatment and achieved a marrow CR
** ORR = overall response rate (CR/CRm + CRh + Cri + MLFS + Marrow CR)

Variant Allele Frequency (VAF) Analysis 229 samples (213 from white blood cells (PaxGene and EDTA) and 16 from bone marrow analysis) were obtained from 59 AML patients treated with either Compound 1 as a single agent or Compound 1 in combination with azacitidine in the Phase 1 study. Next generation sequencing was carried out through target enrichment using HaloPlex® Target followed by Illumina® sequencing; coverage >100X across 75 genes. Digitial droplet PCR (ddPCR) was carried out through an input of 20 ng on a Stilla 3-channel system; VAF data based on >20,000 droplets.

Figure 6:
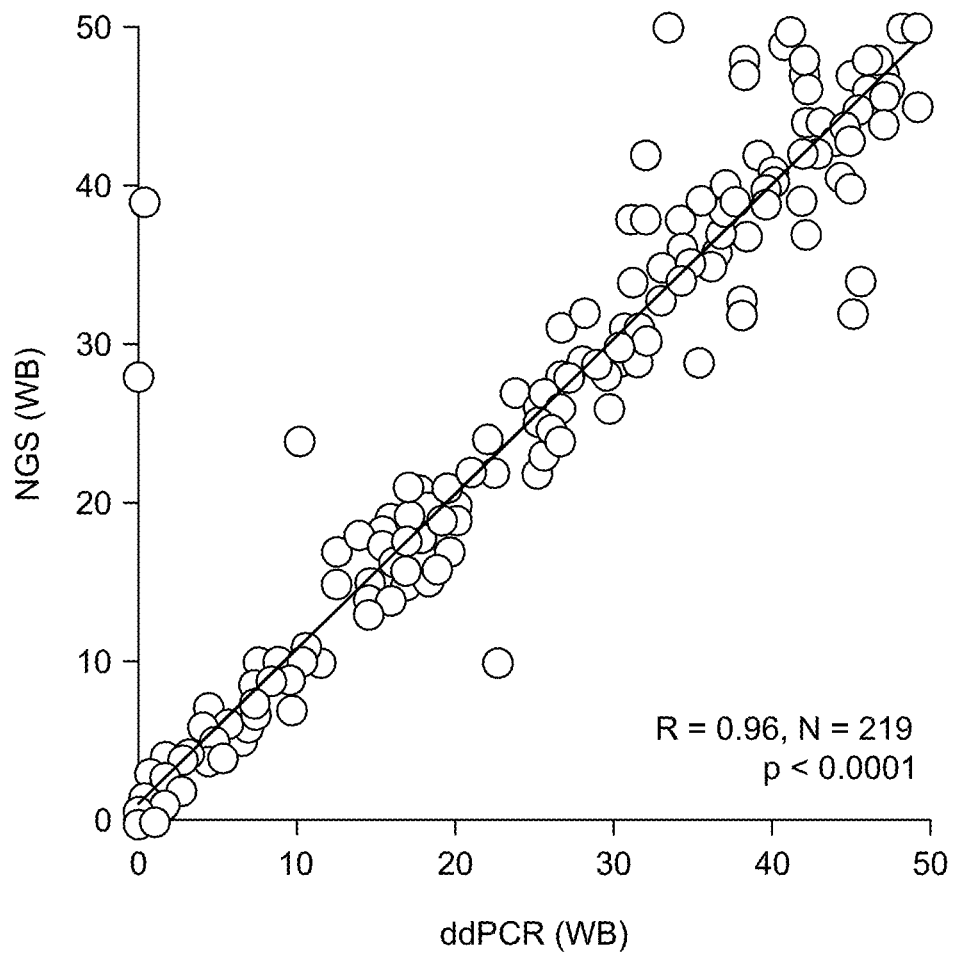
FIG. 6 is a graph showing strong correlation between ddPCR and NGS in AML patients from Example 7.
Figure 7:
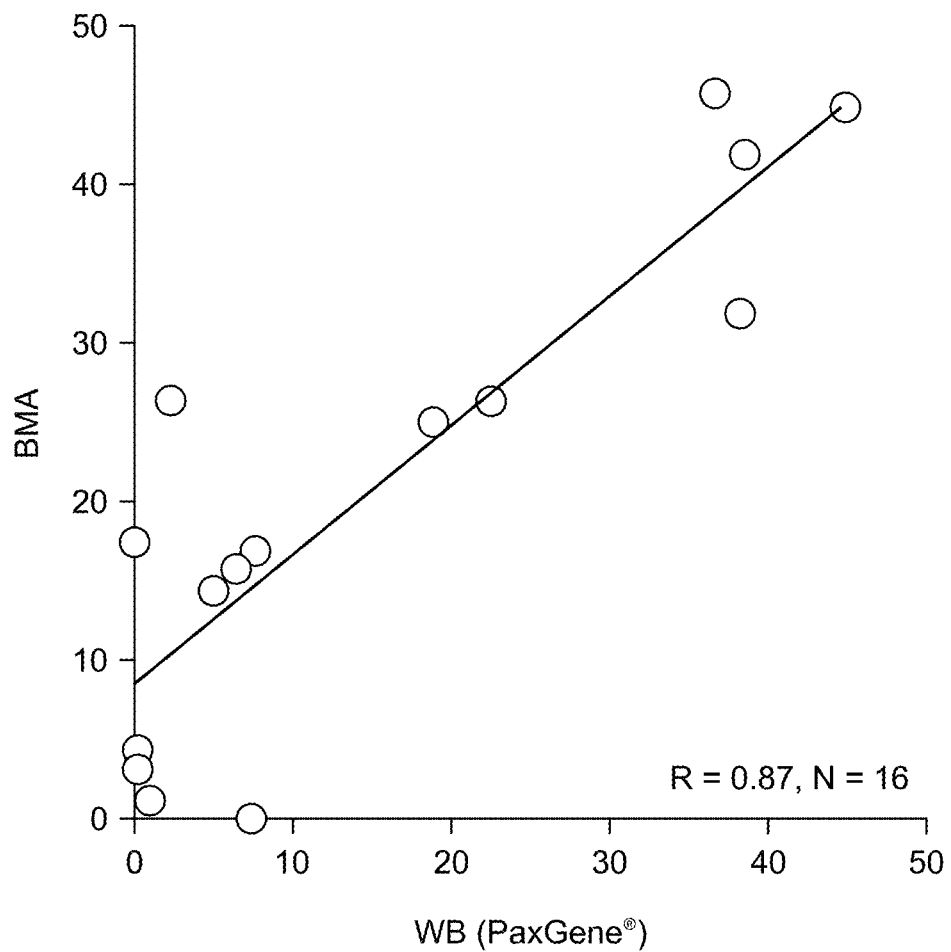
FIG. 7 is a graph showing good concordance in VAF between bone marrow analysis (BMA) and white blood cells (WB) in AML patients from Example 7.
Figure 8:
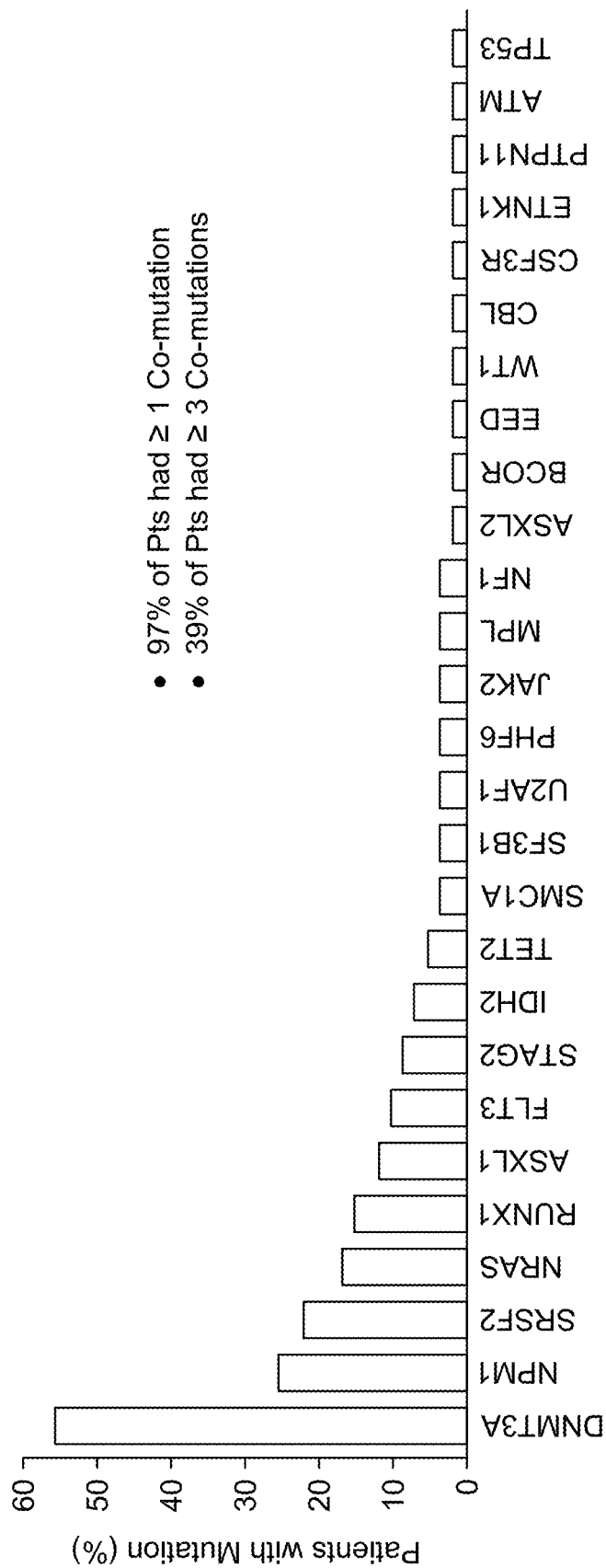
FIG. 8 illustrates frequency of baseline co-mutations in AML patients from Example 7.

As shown in FIG. 6, good correlation between ddPCR and NGS was observed, which justifies using ddPCR for on-treatment assessment of IDH1 VAF. As shown in FIG. 7, detection of IDH1 from BMA can be useful in patients with low IDH1 VAF in WB.

Of the 59 pts with local and central IDH1m results (all sample types included), 53/59 (90%) central testing confirmed presence of IDH1m at study entry.

Clinical Activity

Figure 9A:
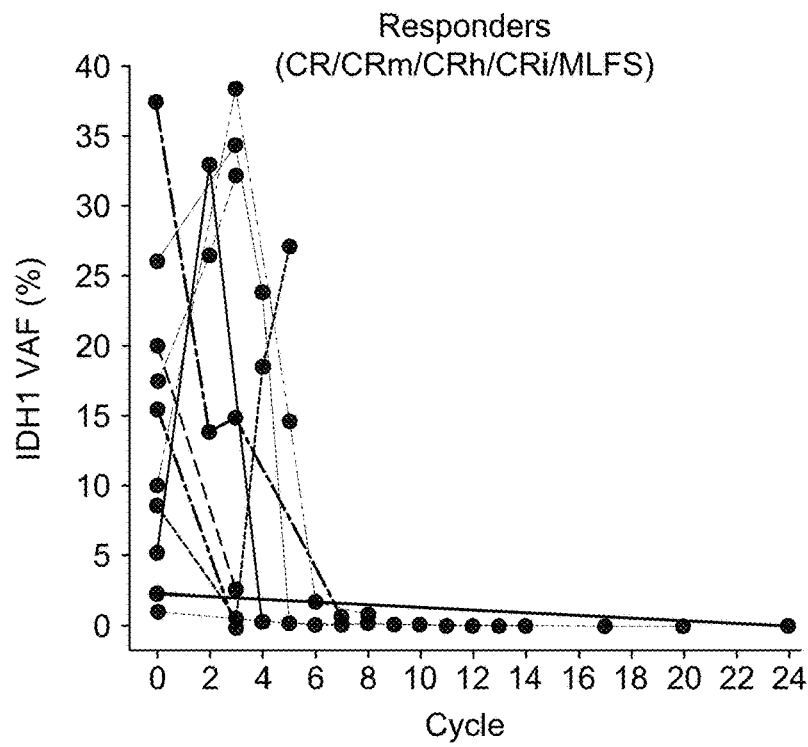
FIG. 9A and FIG. 9B illustrate change in IDH1 VAF across categories.
Figure 9B:
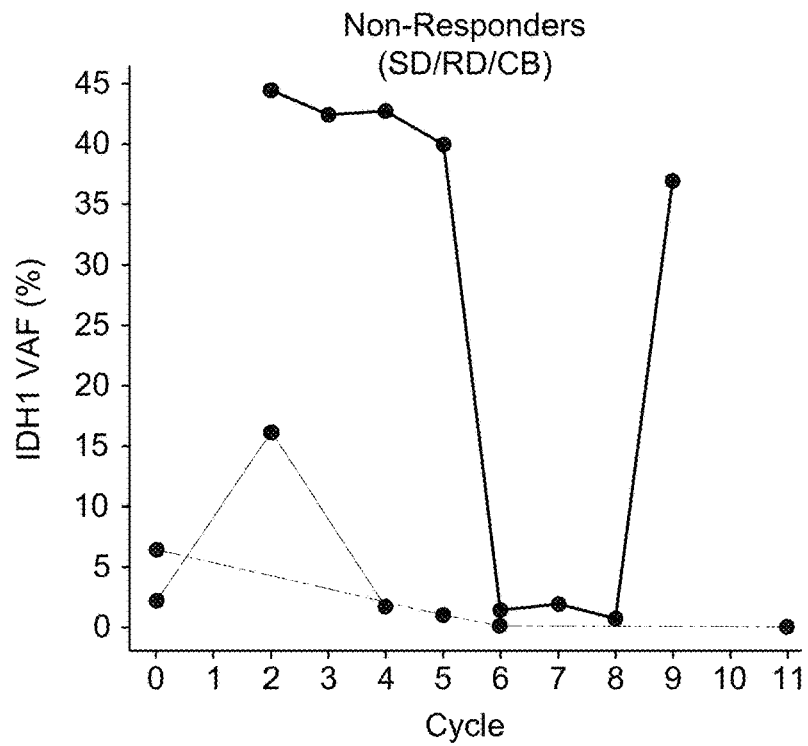
Figure 10:
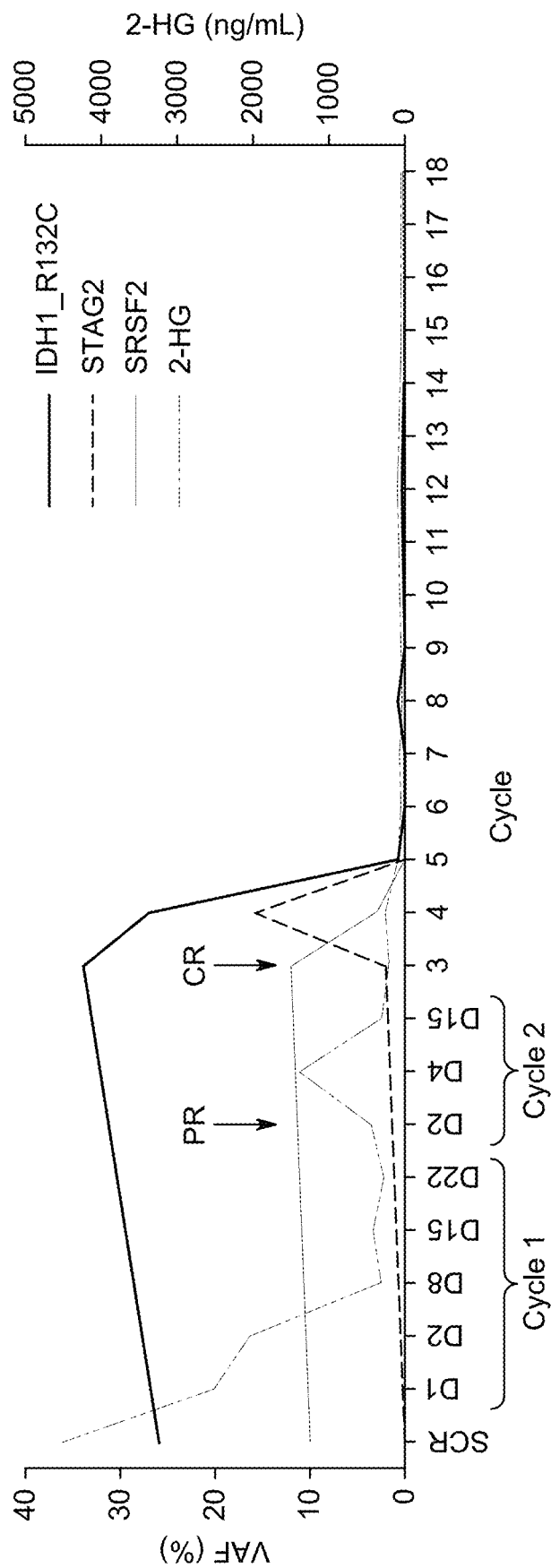
FIG. 10 is a graph showing that clinical response in a treatment naïve (TN) AML patient treated with Compound 1 in combination with azacitidine is associated with decrease in 2-HG and clearance of the IDH1m clone.
Figure 11:
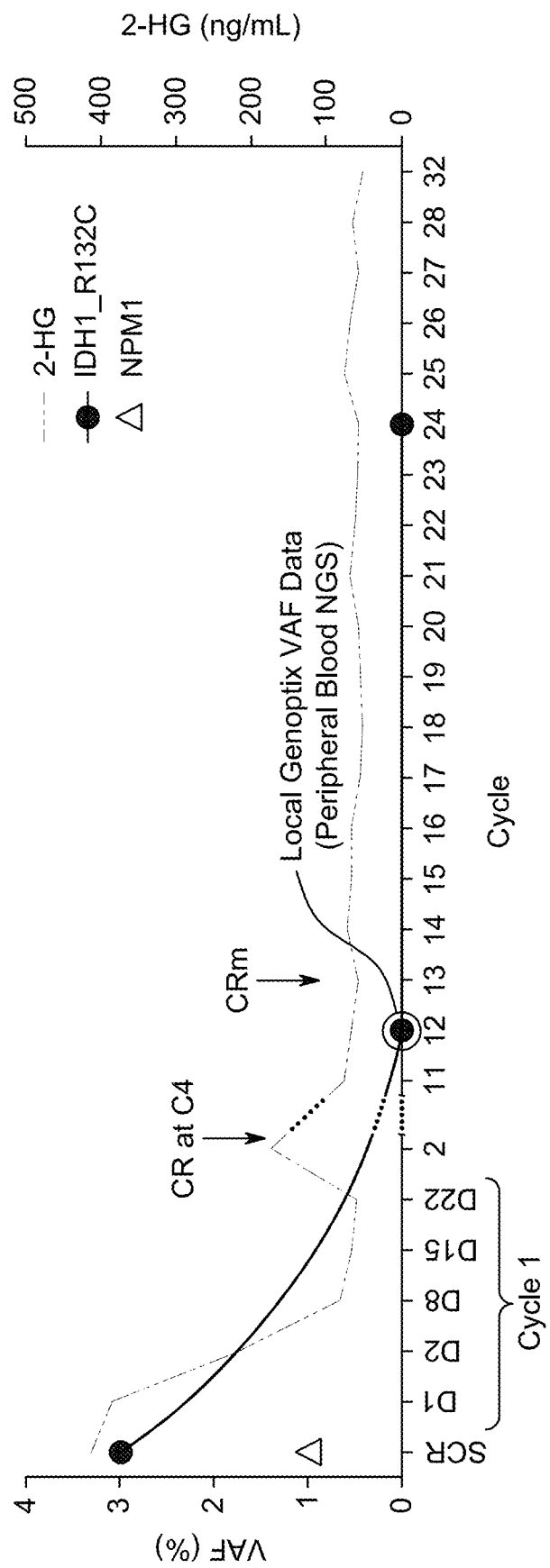
FIG. 11 is a graph showing that clinical response in a R/R AML patient treated with Compound 1 as a single agent is associated with decrease in 2-HG and clearance of the IDH1m clone.

As shown in FIGS. 9A-12, upon treatment with Compound 1, significant reduction in IDH1 VAF across categories was observed. 25 patients achieved an objective response and 6 patients with SD had available longitudinal samples for analysis (VAF at ≥C3). IDH1 mutation clearance/significant reduction is observed in 10/25 (40%) patients with an IWG response to Compound 1 (FIG. 9A). In patients with stable disease, 3/6 (50%) had clearance/significant reduction of the IDH1m VAF (FIG. 9B). FIGS. 10 and 11 show that clinical response is associated with a decrease in 2-HG and clearance of the IDH1m clone.

Mechanism Resistance/Escape

The following details two case studies of individual patients.

Case Study 1: IDH2-Mediated Resistance

Figure 12:
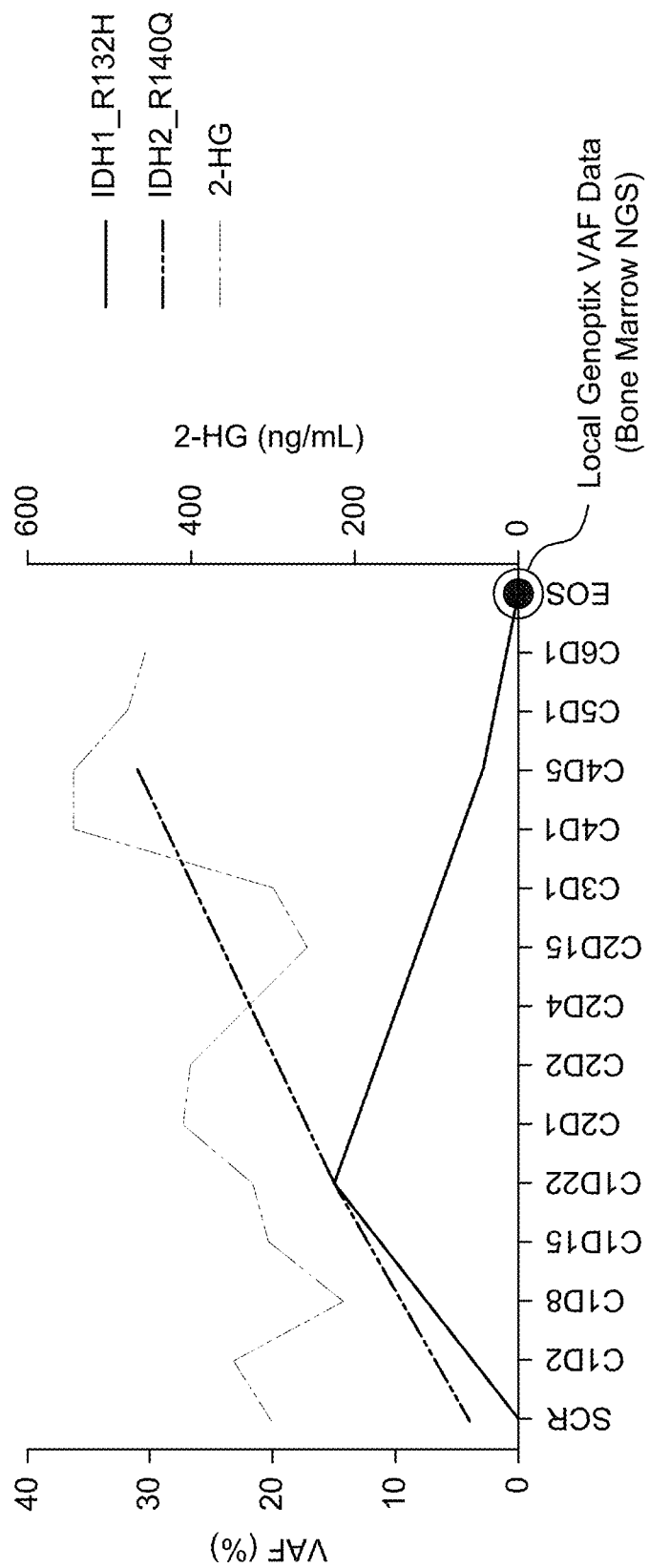
FIG. 12 is a graph showing IDH2-mediated resistance.

As shown in FIG. 12, an R/R AML patient with known IDH2m at baseline was treated with Compound 1 in combination with azacitidine. The patient remained in stable disease for 6 cycles then progressed. Compound 1 induced clearance of the IDH1m clone, however azacitidine was not effective in controlling the IDH2m clone that eventually drove the clinical progression.

Case Study 2: Presence of Additional Non-IDH1m Clones Drive Resistance

Figure 13:
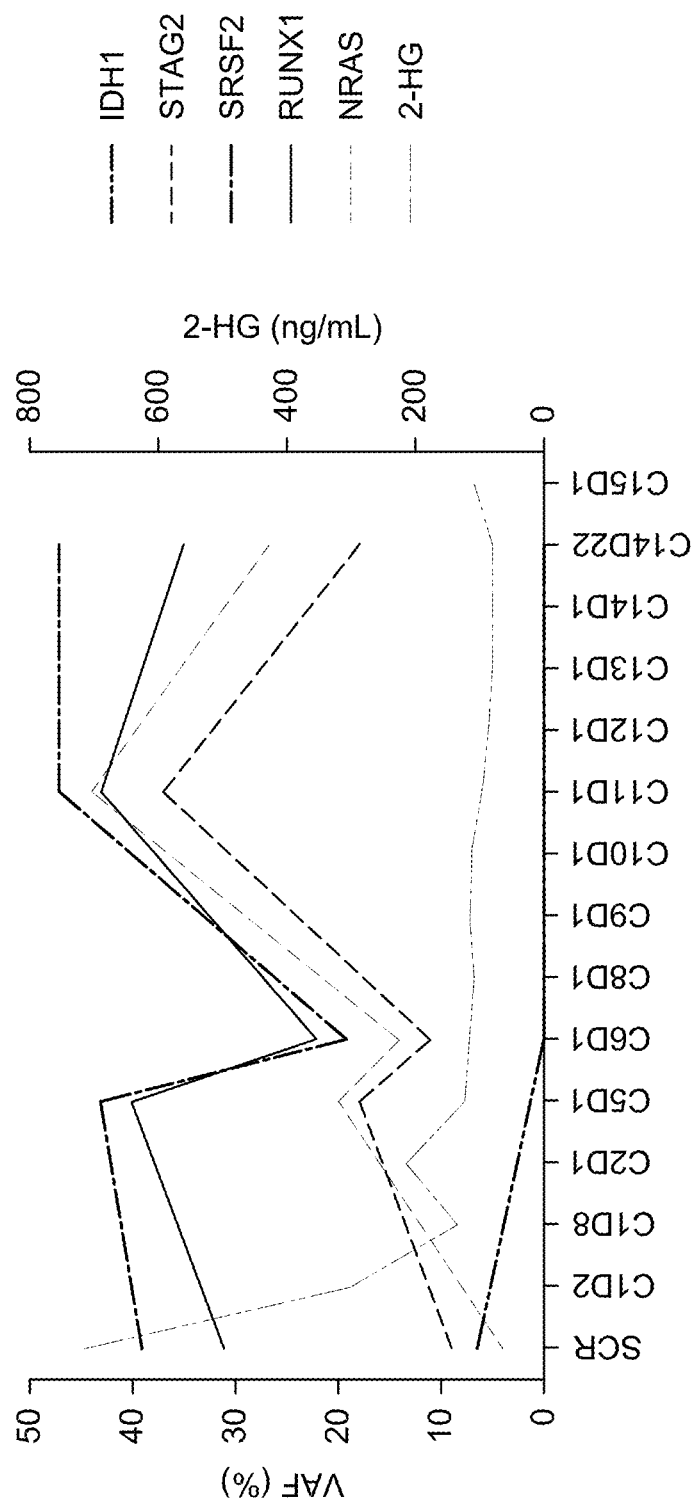
FIG. 13 is a graph showing that presence of additional non-IDH1m clones drive resistance.

A treat naïve AML secondary to MDS patient treated with Compound 1 as a single agent. As shown in FIG. 13, this patient remained stable for 15 cycles with no achievement of an IWG response, however IDH1 mutation clearance and normalization of 2-HG were observed.

Conclusion

Compound 1 demonstrates clinical activity as a single agent and in combination with azacitidine in a high-risk Phase 1 population of AML/MDS patients with IDH1 mutation. In R/R AML, 41% and 46% pts achieve ORR with Compound 1 as a single agent and Compound 1 in combination with azacitidine treatment, respectively. 90% of pts enrolled with a history of IDH1m determined locally had a IDH1m confirmed centrally. Baseline co-mutation analyses demonstrated no correlation with clinical response (likely due to the small number of patients). Compound 1 induces IDH1 mutation clearance or significant reduction in treatment naïve and R/R AML patients regardless of IWG response. Of the 25 patient that achieved an objective response and with available samples (VAF at C3), 10 (40%) had clearance or significant VAF reduction to <1%. Six stable disease patients had samples available and three (50%) had clearance or significant VAF reduction. Initial analysis of patients who relapse/progress on Compound 1 suggests non-IDHm-driven mechanism of escape.

Example 8: Diagnostic for Identifying AML Patients Having a Susceptible mIDH1 Mutation Abbott REALTIME IDH1 is a commercially available, FDA-Approved in vitro polymerase chain reaction (PCR) assay for the qualitative detection of single nucleotide variants (SNVs) coding five IDH1 R132 mutations (R132C, R132H, R132G, R132S, and R132L) in DNA extracted from human blood (EDTA) or bone marrow (EDTA). Abbott RealTime IDH1 is for use with the Abbott m2000rt System.

The Abbott RealTime IDH1 is indicated as an aid in identifying acute myeloid leukemia (AML) patients with an isocitrate dehydrogenase-1 (IDH1) mutation for treatment with an FDA-Approved mIDH1 inhibitor. This test is for prescription use only. The Abbott RealTime IDH1 detects single nucleotide variants (SNVs) coding five IDH1 mutations (R132C, R132H, R132G, R132S, and R132L) by using PCR technology with homogeneous real-time fluorescence detection. The assay uses human blood or bone marrow aspirate specimens and reports a qualitative result. The table below lists the IDH1 mutations detected by the Abbott RealTime IDH1 assay.

TABLE 9

| Codon | IDH1 Mutation | SNV |
| --- | --- | --- |
| R132 | R132C | TGT |
|  | R132H | CAT |
|  | R132G | GGT |
|  | R132S | AGT |
|  | R132L | CTT |

I claim:

1. A method of treating a patient diagnosed with a form of cancer characterized by an IDH1 mutation selected from the group consisting of R132G, R132S and R132L, the method comprising orally administering 150 mg BID of Compound 1, or pharmaceutically acceptable salt thereof, to the patient in need thereof:

(Compound 1)

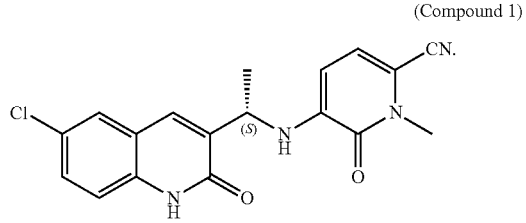

2. The method of claim 1, wherein the patient is diagnosed with a cancer characterized by a concurrent mutation selected from the group consisting of FLT3, NPM1, CEBPA and TP53.

3. The method of claim 1, wherein the patient is diagnosed with a cancer that is not characterized by an IDH2 mutation.

4. The method of claim 1, wherein the patient is diagnosed with acute myeloid leukemia (AML) or myelodysplastic syndrome (MDS) characterized by the IDH1 mutation prior to the administration of Compound 1.

5. The method of claim 4, wherein the patient is diagnosed with MDS or AML further characterized by a concurrent mutation selected from the group consisting of FLT3, NPM1, CEBPA and TP53.

6. The method of claim 1, wherein the patient is diagnosed with a cancer characterized by a concurrent mutation selected from the group consisting of DNMT3A, NPM1, SRSF2, NRAS, RUNX1, ASXL1, FLT3, STAG2, TET2, SMC1A, SF3B1, U2AF1, PHF6, JAK2, MPL, NF1, ASXL2, BCOR, EED, WT1, CBL, CSF3R, ETNK1, PTPN11, ATM and TP53.

7. A method of treating a patient diagnosed with a hematological malignancy characterized by an IDH1 mutation selected from the group consisting of R132C, R132H, R132G, R132S and R132L and a concurrent FLT3 mutation, the method comprising orally administering 150 mg of Compound 1, or pharmaceutically acceptable salt thereof, BID to the patient in need thereof:

(Compound 1)

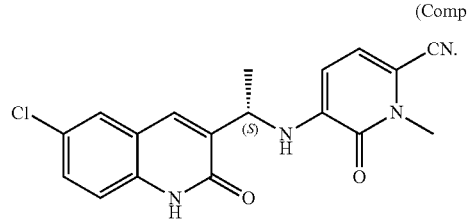

8. The method of claim 7, wherein the patient is diagnosed with a hematological malignancy characterized by a co-mutation selected from the group consisting of DNMT3A, NPM1, SRSF2, NRAS, RUNX1, ASXL1, STAG2, TET2, SMC1A, SF3B1, U2AF1, PHF6, JAK2, MPL, NF1, ASXL2, BCOR, EED, WT1, CBL, CSF3R, ETNK1, PTPN11, ATM and TP53.

9. The method of claim 7, comprising administering Compound 1 to the patient every day for at least 6 months.

10. The method of claim 7, wherein Compound 1 is administered to the patient as a single agent for the treatment of AML.

11. The method of claim 7, wherein the patient does not have an IDH-2 mutation.

12. A method of treating a patient diagnosed with a form of cancer characterized by an IDH1 mutation selected from the group consisting of R132G, R132S and R132L, the method comprising orally administering 150 mg of Compound 1 BID to the patient in need thereof:

(Compound 1)

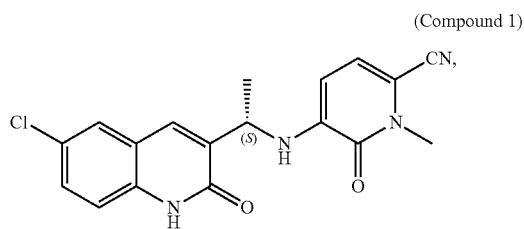

or pharmaceutically acceptable salt thereof, each day for a total of at least 6 months.

13. The method of claim 12, wherein the patient is diagnosed with a cancer characterized by a FLT3 mutation prior to the administration of Compound 1.

14. The method of claim 12, wherein the patient is diagnosed with a cancer characterized by a NPM1 mutation prior to the administration of Compound 1.

15. The method of claim 12, wherein the patient is diagnosed with a cancer characterized by a CEBPA mutation prior to the administration of Compound 1.

16. The method of claim 12, wherein the patient is diagnosed with a cancer characterized by a TP53 mutation prior to the administration of Compound 1.

17. The method of claim 12, wherein the patient is diagnosed with a cancer further characterized by both the mIDH1 mutation and a co-mutation selected from the group consisting of DNMT3A, NPM1, SRSF2, NRAS, RUNX1, ASXL1, STAG2, TET2, SMC1A, SF3B1, U2AF1, PHF6, JAK2, MPL, NF1, ASXL2, BCOR, EED, WT1, CBL, CSF3R, ETNK1, PTPN11, ATM and TP53.

18. The method of claim 12, wherein Compound 1 is administered in a R132X mIDH-1 Selective Inhibitor Therapy consisting of Compound 1 as a single agent.

19. A method of treating patients diagnosed with a cancer harboring an IDH-1 mutation, the method comprising orally administering 150 mg BID of Compound 1, or pharmaceutically acceptable salt thereof, to the patient in need thereof:

(Compound 1)

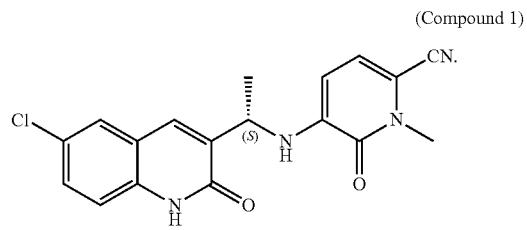

20. The method of claim 19, wherein the patient is diagnosed with acute myeloid leukemia (AML) and Compound 1 is administered to the patient in combination with azacitidine.

21. The method of claim 20, wherein the patient is treated for one or more 28-day treatment cycles, wherein:
a. the azacitidine is administered to the patient at the dose of 75 mg/m$^2$ for 7 days IV/SC per every 28-day cycle; and
b. 150 mg of Compound 1 is administered BID to the patient every day throughout the one or more 28-day treatment cycles.

* * * * *